(12) United States Patent
Wu et al.

(10) Patent No.: US 8,049,069 B2
(45) Date of Patent: Nov. 1, 2011

(54) GENES INVOLVED IN PLANT FIBRE DEVELOPMENT

(75) Inventors: Yingru Wu, Kaleen (AU); Danny James Llewellyn, O'Connor (AU); Adriane Cristine Machado, Nicholls (AU); Elizabeth Salisbury Dennis, Yarralumia (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 952 days.

(21) Appl. No.: 10/594,785

(22) PCT Filed: Mar. 31, 2005

(86) PCT No.: PCT/AU2005/000467
§ 371 (c)(1),
(2), (4) Date: Sep. 17, 2007

(87) PCT Pub. No.: WO2005/095614
PCT Pub. Date: Oct. 13, 2005

(65) Prior Publication Data
US 2008/0196120 A1    Aug. 14, 2008

Related U.S. Application Data

(60) Provisional application No. 60/558,480, filed on Mar. 31, 2004.

(30) Foreign Application Priority Data

Mar. 31, 2004    (AU) .................................. 2004901749

(51) Int. Cl.
| *C12N 15/29* | (2006.01) |
| *C12N 15/82* | (2006.01) |
| *C12N 5/04* | (2006.01) |
| *A01H 5/00* | (2006.01) |
| *A01H 5/10* | (2006.01) |

(52) U.S. Cl. ........ 800/298; 800/278; 800/290; 800/285; 530/300; 536/23.6; 435/320.1; 435/419

(58) Field of Classification Search ........................ None
See application file for complete search history.

(56) References Cited

U.S. PATENT DOCUMENTS

| 4,945,050 A | 7/1990 | Sanford et al. |
| 5,004,863 A | 4/1991 | Umbeck |
| 5,104,310 A | 4/1992 | Saltin |
| 5,141,131 A | 8/1992 | Miller, Jr. et al. |
| 5,159,135 A | 10/1992 | Umbeck |
| 5,177,010 A | 1/1993 | Goldman et al. |
| 5,384,253 A | 1/1995 | Krzyzek et al. |
| 5,472,869 A | 12/1995 | Krzyzek et al. |
| 5,495,070 A | 2/1996 | John |
| 5,602,321 A | 2/1997 | John |
| 5,608,148 A | 3/1997 | John |
| 5,925,517 A | 7/1999 | Tyagi et al. |
| 5,932,713 A | 8/1999 | Kasukabe et al. |
| 6,297,429 B1 * | 10/2001 | Takatsuji et al. .............. 800/290 |
| 2004/0123338 A1 * | 6/2004 | Fincher ......................... 800/278 |

FOREIGN PATENT DOCUMENTS

| EP | 0465572 | 6/1995 |
| EP | 1033405 A2 | 9/2000 |
| WO | WO 87/06614 | 11/1987 |
| WO | WO 92/09696 | 6/1992 |
| WO | WO 93/21335 | 10/1993 |
| WO | WO 96/06932 | 3/1996 |
| WO | WO 97/20936 | 6/1997 |
| WO | WO 99/49029 | 9/1999 |
| WO | WO 99/53050 | 10/1999 |
| WO | WO 01/34815 | 5/2001 |
| WO | WO 03/076619 | 9/2003 |

OTHER PUBLICATIONS

Cedroni et al (2003, Plant Molecular Biology 51:313-325).*
Bowie et al, Science 247:1306-1310, 1990.*
McConnell et al, Nature 411 (6838):709-713, 2001.*
Machado et al (2009, The Plant Journal 59(1):52-62).*
Examiner's First Report issued on Oct. 7, 2009 in connection with Australian Application No. 504881.
Suo, J. et al., (2003) "Identification of *GhMYB109* Encoding a R2R3 MYB Transcription Factor That Expressed Specifically in Fiber Initials and Elongating Fibers of Cotton (*Gossypium hirsutum* L.)," *Biochimica et Biophysica Acta*, 1630: 25-34.
Ji, S-J. et al., (2003) "Isolation and Analyses of Genes Preferentially Expressed During Early Cotton Fiber Development by Subtractive PCR and cDNA Array," *Nucleic Acids Research*, 31(10): 2534-2543.
Ali, S. et al.,(2000) "Normalisation of Cereal Endosperm EST Libraries for Structural and Functional Genomic Analysis," *Plant Molecular Biology Reporter*, 18(2): 123-13.
Beasley, C.A. and I.P. Ting, (1973) "The Effects of Plant Growth Substances on in Vitro Fiber Development From Fertilized Cotton Ovules," *American Journal of Botany* 60(2): 130-139.
Bourque, J., (1995) "Antisense Strategies for Genetic Manipulations in Plants," *Plant Science*, 105(2): 125-149.
Cousins, Y.L., et al., (1991) "Transformation of an Australian Cotton Cultivar: Prospects for Cotton Improvement Through Genetic Engineering," *Australian Journal of Plant Physiology*, 18(5): 481-494.
Craig, S., and C.D. Beaton, (1996) "A Simple Cryo-SEM Method for Delicate Plant Tissues," *Journal of Microscopy*, 182(2): 102-105.
Di Cristina, M., et al., (1996) "The *Arabidopsis* Athb-10 (GLABRA2) Is an HD-Zip Protein Required for Regulation of Root Hair Development," *The Plant Journal*, 10(3): 393-402.

(Continued)

Primary Examiner — Stuart F. Baum
(74) *Attorney, Agent, or Firm* — John P. White; Cooper & Dunham LLP

(57) ABSTRACT

The present invention provides polypeptides, and polynucleotides encoding therefore, involved in the regulation of fibre initiation and/or elongation in fibre producing plants. In particular, the present invention provides methods of altering fibre initiation in cotton making use of transcription factors, regulatory proteins or cell cycle proteins produced at or around anthesis. The invention also relates to the use of these as markers of fibre production in plants including cotton.

14 Claims, 5 Drawing Sheets

OTHER PUBLICATIONS

Figure 1A:
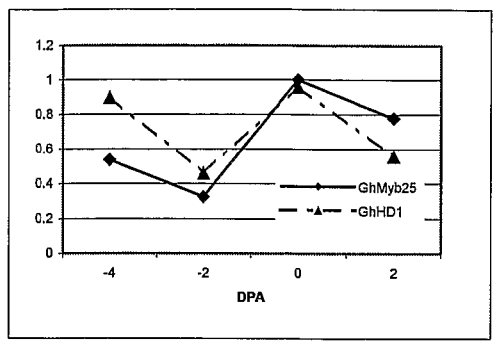
Figure 1A:
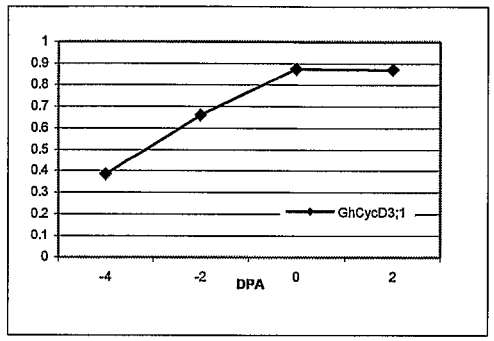
Figure 1A:
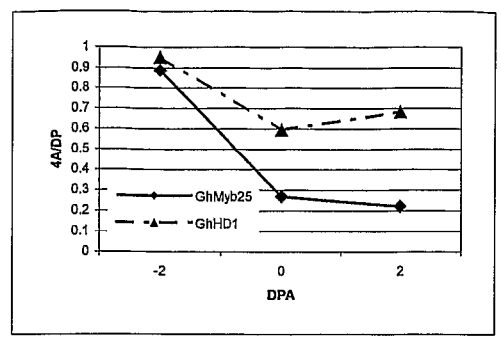
Figure 1A:
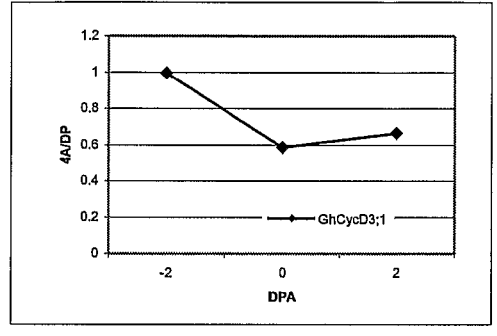
Figure 1B:
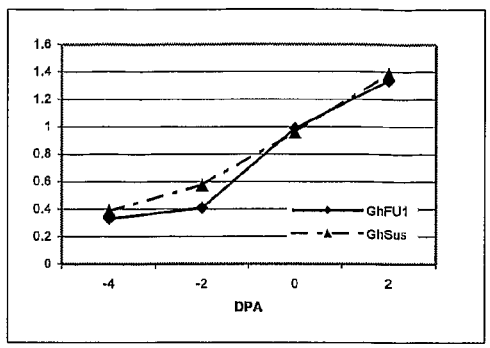
Figure 1B:
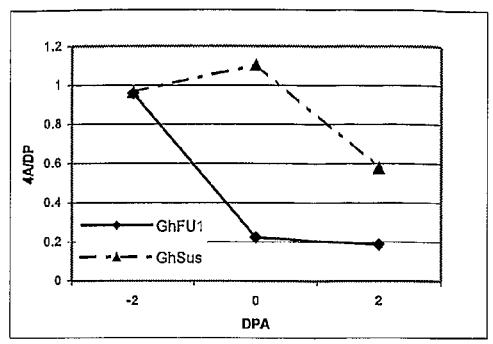
Figure 1B:
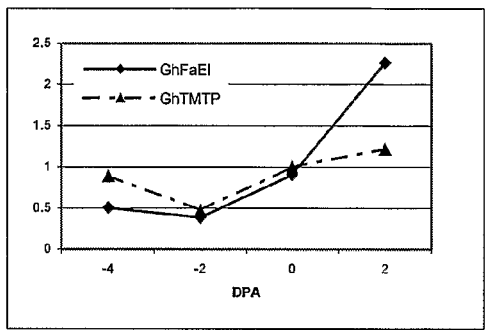
Figure 1B:
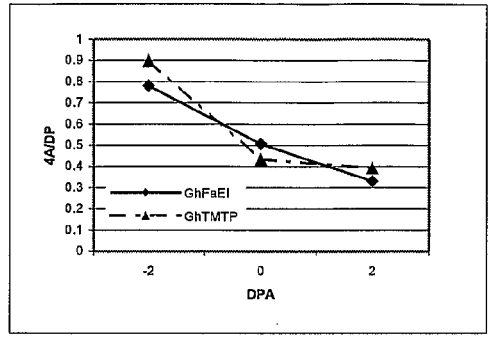
Figure 1B:
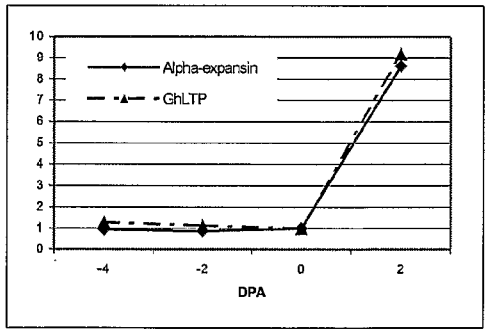
Figure 1B:
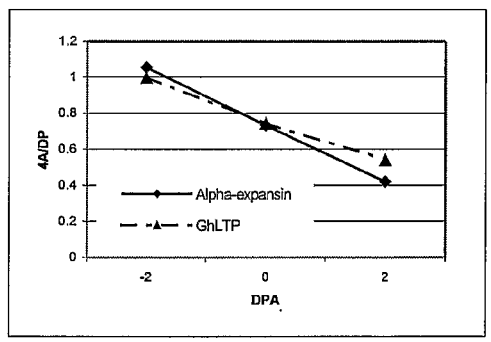
Figure 1B:
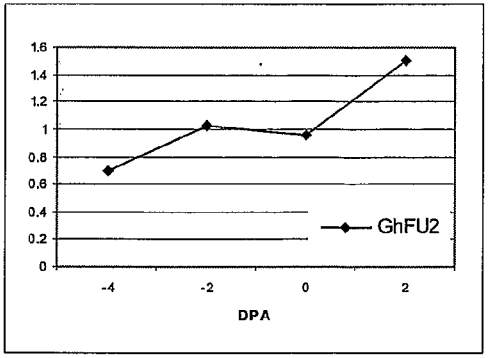
Figure 1B:
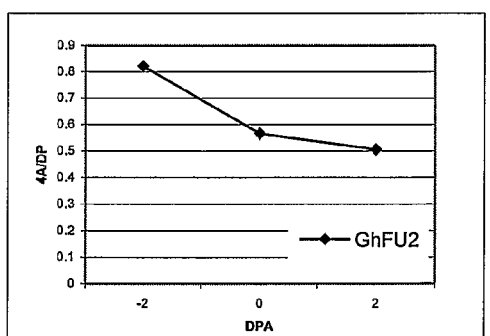

Dowd, C., et al., (2004) "Gene Expression Profile Changes in Cotton Root and Hypocotyl Tissues in Response to infection with *Fusarium oxysporum* f. sp. *Vasinfectum*," *Molecular Plant-Microbe Interactions*, 17(6): 654-667.

Fatima Bonaldo, M., et al., (2007) "Normalization and Subtraction: Two Approaches to Facilitate Gene Discovery," *Genome Research*, 6(9): 791-806.

Glover, B.J., et al., (1998) "Development of Several Epidermal Cell Types Can Be Specified by the Same MYB-related Plant Transcription Factor," *Development*, 125(17): 3497-3508.

Harmer, S.E., et al., (2002) "Characterisation of six α-expansin genes in *Gossypium hirsutum* (upland cotton)," *Mol Genet Genomics*, 268(1): 1-9.

Haseloff, J. and W.L. Gerlach, (1988) "Simple RNA Enzymes With New and Highly Specific Endoribonuclease Activities," *Nature*, 334(6183): 585-591.

Hasenfratz, M., et al., (1995) "Expression of Two Related Vacuolar H+-ATPase 16-Kilodalton Proteolipid Genes Is Differentially Regulated in a Tissue-Specific Manner," Plant Physiology, 108(4): 1395-1404.

Horsch, R.B., et al.,(1985) "A Simple and General Method for Transferring Genes Into Plants," Science, 227(4691): 1229-1231.

Ji, Sheng-Jian, et al., (2003) "Isolation and analyses of genes preferentially expressed during early cotton fiber development by subtractive PCR and cDNA array," Nucleic Acids Research, 31(10): 2534-2543.

Joubés, J. and Chevalier C., (2000) "Endoreduplication in higher plants," Plant Molecular Biology, 43(5-6): 735-745.

Joubés, J., et al., (2000) "Molecular characterization of the expression of distinct classes of cyclins during the early development of tomato fruit," Planta, 211(3): 430-439.

Li, Chun-Hong, et al., (2002) "Isolation of genes preferentially expressed in cotton fiber by cDNA filter arrays and RT-PCR," Plant Science, 163(6): 1113-1120.

Li, Xue-Bao, et al., (2002) Molecular Characterisation of Cotton GhTUB1 Gene That Is Preferentially Expressed in Fiber, Plant Physiology, 130(10.1104): 666-674.

Loguercio, L.L., et al., (1999) "Differential Regulation of Six Novel MYB-Domain Genes Defines Two Distinct Expression Patterns in Cotton (*Gossypium hirsutem* L.)," Molecular and General Genetics, 261(4-5): 660-671.

Lu, P., et al., (1996) "Identification of a Meristem L1 Layer-Specific Gene in *Arabidopsis* That Is Expressed During Embryonic Pattern Formation and Defines a New Class of Homeobox Genes," The Plant Cell, 8(12): 2155-2168.

Ma, D., et al., (1995) "Differential Expression of a Lipid Transfer Protein Gene in Cotton Fiber," Biochimica et Biophysica Acta, 1257(1): 81-84.

Ma, D., et al., (1997) "Cloning and Characterization of a Cotton Lipid Transfer Protein Gene Specifically Expressed in Fiber Cells," *Biochimica et Biophysica Acta*, 1344(2): 111-114.

Masucci, J., et al., (1996) "The Homeobox Gene GLABRA 2 Is Required for Position-Dependent Cell Differentiation in the Root Epidermis of *Arabidopsis thaliana*," *Development*, 122(4): 1253-1260.

Meijer, M. and Murray, J.A.H., (2000) "The role and regulation of D-type cyclins in the plant cell cycle," *Plant Molecular Biology*, 43(5-6): 621-633.

Murray, F., et al., (1999) "Expression of the *Talaromyces flavus* Glucose Oxidase Gene in Cotton and Tobacco Reduces Fungal Infection, But Is Also Phytotoxic," *Molecular Breeding*, 5(3): 219-232.

Nakazono, M., et al., (2003) "Laser-Capture Microdissection, a Tool for Global Analysis of Gene Expression in Specific Plant Cell Types: Identification of Genes Expressed Differently in Epidermal Cells or Vascular Tissues of Maize," *The Plant Cell*, 15(3): 583-596.

Noda, K., et al., (1994) "Flower Colour Intensity Depends on Specialized Cell Shape Controlled by a Myb-Related Transcription Factor," *Nature*, 369(6482): 661-664.

Ohashi, Y., et al., (2002) "Entopically additive expression of GLABRA2 alters the frequency and spacing of trichome initiation," *The Plant Journal*, 29(3): 359-369.

Orford, S.J. and J.N. Timmis,(1998) "Specific Expression of an Expansin Gene During Elongation of Cotton Fibres," 1389(3): 342-346.

Payne, T., et al., (1999) "Heterologous MYB Genes Distinct From GL1 Enhance Trichome Production When Overexpressed in *Nicotiana Tabacum*," *Development*, 126(4): 671-682.

Rerie, W.G. , et al., (2007) "The GLABRA2 gene encodes a homeo domain protein required for normal trichome development in *Arabidopsis*," Genes & Development, 8(12): 1388-1399.

Riou-Khamlichi, C., et al., (1999) "Cytokinin Activation of *Arabidopsis* Cell Division Through a D-Type Cyclin," Science, 283(5407): 1541-1544.

Ruan, Y. and P.S. Chourey, (1998) "A Fiberless Seed Mutation in Cotton Is Associated With Lack of Fiber Cell Initiation in Ovule Epidermis and Alterations in Sucrose Synthase Expression and Carbon Partitioning in Developing Seeds," Plant Physiology, 118(2): 399-406.

Schellmann, S., et al., (2002) "TRIPTYCHON and CAPRICE mediate lateral inhibition during trichome and root hair patterning in *Arabidopsis*," The EMBO Journal, 21(19): 5036-5046.

Schenk, P. M., et al., (2000) "Coordinated plant defnse response in *Arabidopsis* revealed by microarray analysis," PNAS, 97(21): 11655-11660.

Schnittger, A., et al., (2002) "Ectopic D-type cyclin expression induces not only DNA replication but also cell division in *Arabidopsis* trichomes," PNAS, 99(9):6410-6415.

Schünmann, P.H.D., et al., (2003) "A suite of novel promoters and terminators for plant biotechnology," Functional Plant Biology, 30(4): 443-452.

Smith, N. A., et al., (2000) "Total silencing by intron-spliced hairpin RNAs," Nature, 407(6802): 319-320.

Solano, R., et al., (1995) "Dual DNA Binding Specificity of a Petal Epidermis-specific MYB Transcription Factor (MYB.Ph3) From Petunia Hybrida," The EMBO Journal, 14(8): 1773-1784.

Sorrell, D.A., et al.,(1999) "Distinct Cyclin D Genes Show Mitotic Accumulation or Constant Levels of Transcripts in Tobacco Bright Yellow-2 Cells," Plant Physiology, 119(1): 343-351.

Stracke, R., et al., (2001) "The R2R3-MYB gene family in *Arabidopsis thaliana*," Current Opinion in Plant Biology, 4(5): 447-456.

Szymanski, D. and M.D. Marks, (1998) "GLABROUS1 Overexpession and TRIPTYCHON Alter the Cell Cycle and Trichome Cell Fate in *Arabidopsis*," The Plant Cell, 10(12): 2047-2062.

Szymanski, D.B., et al., (2000) "Progress in the molecular genetic analysis of trichome initiation and morphogenesis in *Arabidopsis*," Trends in Plant Science, 5(5):214-219.

Van'T Hof, J., (1999) "Increased Nuclear DNA Content in Developing Cotton Fiber Cells," American Journal of Botany, 86(6): 776-779.

Walker, A.R., et al., (1999) "The Transparent Testa GLABRA1 Locus, Which Regulates Trichome Differentiation and Anthocyanin Biosynthesis in *Arabidopsis*, Encodes a WD40 Repeat Protein," The Plant Cell, 11(7): 1337-1349.

Waterhouse, P.M., et al., (1998) "Virus Resistance and Gene Silencing in Plants Can Be Induced by Simultaneous Expression of Sense and Antisense RNA," Proceedings of the National Academy of Sciences, 95(23): 13959-13964.

Wesley, S. V., et al., (2001) "Construct design for efficient, effective and high-throughput gene silencing in plants," The Plant Journal, 27(6): 581-590.

Wilson, D.L., et al., (2003) "New normalization methods for cDNA microarray data," Bioinformatics, 19(11):1325-1332.

Wu, Y., et al., (2002) "A Quick and Easy Method for Isolating Good-Quality RNA From Cotton (*Gossypium hirsutum* L.) Tissues," Plant Molecular Biology Reporter, 20(3): 213-218.

Zimmet, J.M., et al., (1997) "A Role for Cyclin D3 in the Endomitotic Cell Cycle," *Molecular and Cellular Biology*, 17(12):7248-7259.

International Preliminary Report on Patentability issued by the International Bureau of WIPO dated Oct. 4, 2006 in connection with International Application No. PCT/AU2005/000467.

* cited by examiner

Class I

A

B

Class II

A  B

GENES INVOLVED IN PLANT FIBRE DEVELOPMENT

This application is a §371 national stage of PCT International Application No. PCT/AU2005/000467, filed Mar. 31, 2005, and claims priority of Australian Patent Application No. 2004901749, filed Mar. 31, 2004, and claims the benefit of U.S. Provisional Application No. 60/558,480, filed Mar. 31, 2004, the contents of all of which are hereby incorporated by reference into this application.

FIELD OF THE INVENTION

The present invention relates to polypeptides, and polynucleotides encoding therefor, involved in the regulation of fibre initiation and/or elongation in fibre producing plants. In particular, the present invention provides methods of altering fibre initiation in cotton and products thereof. The invention also relates to the use of these polypeptides and polynucleotides as markers of fibre production in plants including cotton.

BACKGROUND OF THE INVENTION

Cotton (*Gossypium hirsutum*, and to a lesser extent *Gossypium barbadense* together with other *Gossypium* species) provides about 55% of the fibre used in textile manufacturing globally and is an important contributor to world economies. The cotton fibre is probably the most elongated cell in the plant kingdom. The molecular mechanisms that control the differentiation of this elongated plant cell are still largely unknown. Although commonly called fibres, these cells are not part of the vascular tissue and arise, instead, from the ovule epidermis. Fibres of cotton are extremely long single elongated epidermal cells that develop on the outer surface of cotton ovules, reaching upwards of 5 centimeters in some species. Fibre initiation starts between a day before and up to a day after anthesis and the fibre initials begin to elongate immediately after fertilisation, ballooning out from the surface of the seed coat epidermis. After a period of elongation, secondary cell wall thickening fills the fibre with cellulose and the fibre dies and collapses to form the mature fibre that is harvested from the seeds.

In contrast to the discovery of numerous genes responsible for fibre elongation and secondary cell wall synthesis, few genes have been identified that are associated with fibre initiation. Early cytological studies showed structural changes in fibre initials occur up to three days before anthesis: including enlarged nucleoli and nuclei, as well as an increased number of Golgi complexes (Berlin, 1986). It has been proposed that the *Arabidopsis* leaf trichomes, which require at least twenty genes for normal development (Hülskamp et al., 1994), could serve as a model for elucidating the genetic mechanisms controlling cotton fibre initiation and differentiation.

One of the first genes to be characterised in controlling leaf trichomes, GLABROUS1 (GL1), encodes a member of the Myb family of transcription factors (Oppenheimer et al., 1991). An exhaustive search of a cotton ovule cDNA library recovered six novel Myb-domain genes, but none of them encoded a GL1 homolog (Loguercio et al., 1999). *Arabidopsis* trichome initiation is proposed to be controlled by a trichome promoting complex comprised of GL1, TRANSPARENT TESTA GLABRA1 (TTG1, a WD40 protein), and GLABRA3 (GL3, a basic Helix-Loop-Helix protein). GLABRA2 (GL2, a Homeodomain protein) regulates trichome morphology and spacing and TRIPTYCHON (TRY, a Myb-like protein) mediates lateral inhibition of trichome development in cells adjacent to each trichome (Rerie et al., 1994; Walker et al., 1999; Szymanski et al., 2000; Schellmann et al., 2002; Ohashi et al., 2002). However, genes with similar functions in cotton have yet to be identified, and hence it remains speculative whether these two single celled epidermal hair systems share any common features.

There is a need for the identification and characterization of genes involved in fibre initiation in fibre producing plants such as cotton. This will enable markers to be used to screen plants for desirable fibre traits, as well as allow for the production of transgenic plants with altered fibre production.

SUMMARY OF THE INVENTION

To identify genes that may be specific to fibre initiation, the present inventors have used mRNA from early stage fertilised ovules of wild type and 5 lintless mutants of cotton (that produce little if any fibres) to probe a cotton ovule cDNA microarray containing 10,000 cDNAs expressed around the time of fibre cell differentiation. Since pollination may already have occurred and zygote development initiated at this stage, the inventors used a separate microarray comparison between the mRNAs of the outer integument and those of the inner ovule tissues of the wild type cotton to filter out those genes that are not expressed specifically in the seed coat outer integument where the fibres are initiated. Using this strategy genes have been identified that are differentially expressed in the lintless mutants, and hence play a role in fibre initiation.

In one aspect, the present invention provides a method of altering fibre initiation and/or elongation in a fibre producing plant comprising manipulating said plant such that the production of a polypeptide is modified when compared to a wild-type plant, wherein the polypeptide is a transcription factor, regulatory protein, or a cell cycle protein, produced in said wild type plant at, or around, anthesis.

Preferably, the polypeptide comprises a sequence selected from the group consisting of:

i) an amino acid sequence provided as any one of SEQ ID NO's:1 to 3 or 12; or ii) an amino acid sequence which is at least 50% identical to any one of SEQ ID NO's:1 to 3 or 12.

In another aspect the present invention provides a method of altering fibre initiation and/or elongation in a fibre producing plant comprising manipulating said plant such that the production of a polypeptide is modified when compared to a wild-type plant, wherein the polypeptide comprises a sequence selected from the group consisting of:

i) an amino acid sequence provided as any one of SEQ ID NO's:1 to 16; or ii) an amino acid sequence which is at least 50% identical to any one of SEQ ID NO's:1 to 16.

Preferably, the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to any one of SEQ ID NO's: 1 to 16.

In one embodiment, the polypeptide comprises a sequence selected from the group consisting of:
  i) an amino acid sequence provided as SEQ ID NO:1; or
  ii) an amino acid sequence which is at least 80% identical to SEQ ID NO:1.

In another embodiment, the polypeptide comprises a sequence selected from the group consisting of:
  i) an amino acid sequence provided as SEQ ID NO:2; or
  ii) an amino acid sequence which is at least 80% identical to SEQ ID NO:2.

In a further embodiment, the polypeptide comprises a sequence selected from the group consisting of:
  i) an amino acid sequence provided as SEQ ID NO:3; or
  ii) an amino acid sequence which is at least 80% identical to SEQ ID NO:3.

In another embodiment, the method comprises recombinantly expressing the polypeptide in said plant.

In an alternate embodiment, the method comprises reducing the level of the polypeptide endogenously produced by the plant. This can be achieved by any means known in the art. One example is by exposing the plant to an antisense polynucleotide or a catalytic polynucleotide which hybridizes to an mRNA molecule encoding the polypeptide. Another example is by exposing the plant to a dsRNA molecule that specifically down-regulates mRNA levels in a cell of an mRNA molecule encoding the polypeptide.

In a further embodiment, the plant is a horticultural plant.

In a particularly preferred embodiment, the plant is a species of the Genus *Gossypium*.

In a further aspect, the present invention provides a method of assessing the potential of a fibre producing plant to produce fibre, the method comprising analysing the plant for a genetic variation in a polynucleotide associated with fibre initiation and/or elongation, wherein the polynucleotide encodes a transcription factor, regulatory protein, or a cell cycle protein, produced in a wild type plant at, or around, anthesis.

Preferably, the polynucleotide comprises a sequence selected from the group consisting of:
  i) a nucleotide sequence provided as any one of SEQ ID NO's:17 to 22, or 38; or
  ii) a nucleotide sequence which is at least 50% identical to any one of SEQ ID NO's:17 to 22, or 38.

In another aspect, the present invention provides a method of assessing the potential of a fibre producing plant to produce fibre, the method comprising analysing the plant for a genetic variation in a polynucleotide associated with fibre initiation and/or elongation, wherein the polynucleotide comprises a sequence selected from the group consisting of:
  i) a nucleotide sequence provided as any one of SEQ ID NO's:17 to 45; or
  ii) a nucleotide sequence which is at least 50% identical to any one of SEQ ID NO's:17 to 45.

Preferably, the polynucleotide comprises a nucleotide sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to any one of SEQ ID NO's: 17 to 45.

As the skilled addressee would be aware, the genetic variation associated with fibre initiation and/or elongation may be in the coding portion of a polynucleotide of the invention, or may be genetically linked to be useful as a marker for fibre initiation and/or elongation.

In one embodiment, the method comprises performing an amplification reaction on nucleic acids obtained from said plant, or nucleic acids synthesized using nucleic acids from said plant as a template, wherein the production of an amplicon in said amplification reaction indicates an association with fibre producing potential.

In another embodiment, the method comprises performing an amplification reaction on nucleic acids obtained from said plant, or nucleic acids synthesized using nucleic acids from said plant as a template, wherein the lack of production of an amplicon in said amplification reaction indicates an association with fibre producing potential.

In a further embodiment, the method comprises performing a hybridization reaction on nucleic acids obtained from said plant, or nucleic acids synthesized using nucleic acids from said plant as a template, wherein a detectable signal produced by the hybridization reaction indicates reduced fibre producing potential.

In yet another embodiment, the method comprises performing a hybridization reaction on nucleic acids obtained from said plant, or nucleic acids synthesized using nucleic acids from said plant as a template, wherein the lack of a detectable signal by the hybridization reaction indicates reduced fibre producing potential.

In an alternate embodiment, the polynucleotide is mRNA and the method comprises determining the levels of mRNA of the polynucleotide in the plant ovule at, or around, anthesis.

In a further aspect, the present invention provides a method of assessing the potential of a fibre producing plant to produce fibre, the method comprising analysing the plant for a polypeptide involved in fibre initiation and/or elongation, wherein the polypeptide is a transcription factor, regulatory protein, or a cell cycle protein, produced in a wild type plant at, or around, anthesis.

In a further aspect, the present invention provides a method of assessing the potential of a fibre producing plant to produce fibre, the method comprising analysing the plant for polypeptide involved in fibre initiation and/or elongation, wherein the polypeptide comprises a sequence selected from the group consisting of:
  i) an amino acid sequence provided as any one of SEQ ID NO's:1 to 16; or
  ii) an amino acid sequence which is at least 50% identical to any one of SEQ ID NO's:1 to 16.

Preferably, the method comprises determining the levels of the polypeptide in the plant ovule at, or around, anthesis.

In another aspect, the present invention provides a substantially purified polypeptide selected from the group consisting of:
  i) a polypeptide comprising an amino acid sequence as provided in SEQ ID NO:1,
  ii) a polypeptide comprising an amino acid sequence which is at least 87% identical to SEQ ID NO:1, and
  iii) a biologically active fragment of i) or ii),
wherein the polypeptide regulates fibre initiation and/or elongation.

Preferably, the polypeptide comprises an amino acid sequence which is at least 95% identical to SEQ ID NO:1.

In a further aspect, the present invention provides a substantially purified polypeptide selected from the group consisting of:
   i) a polypeptide comprising an amino acid sequence as provided in SEQ ID NO:2, and
   ii) a biologically active fragment of i),
wherein the polypeptide regulates fibre initiation and/or elongation.

In yet another aspect, the present invention provides a substantially purified polypeptide selected from the group consisting of:
   i) a polypeptide comprising an amino acid sequence as provided in SEQ ID NO:3,
   ii) a polypeptide comprising an amino acid sequence which is at least 54% identical to SEQ ID NO:3, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:4,
   ii) a polypeptide comprising an amino acid sequence which is at least 55% identical to SEQ ID NO:4, and
   iii) a biologically active fragment of i) or ii),
wherein the polypeptide regulates fibre initiation and/or elongation.

In another aspect, the present invention provides substantially purified polypeptide selected from the group consisting of:
   i) a polypeptide comprising an amino acid sequence as provided in SEQ ID NO:5,
   ii) a polypeptide comprising an amino acid sequence which is at least 50% identical to SEQ ID NO:5, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:6,
   ii) a polypeptide comprising an amino acid sequence which is at least 50% identical to SEQ ID NO:6, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:7,
   ii) a polypeptide comprising an amino acid sequence which is at least 79% identical to SEQ ID NO:7, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:8,
   ii) a polypeptide comprising an amino acid sequence which is at least 66% identical to SEQ ID NO:8, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:9,
   ii) a polypeptide comprising an amino acid sequence which is at least 95% identical to SEQ ID NO:9, and
   iii) a biologically active fragment of i) or ii),
wherein the polypeptide regulates fibre initiation and/or elongation.

In another aspect, the present invention provides s substantially purified polypeptide selected from the group consisting of:
   i) a polypeptide comprising an amino acid sequence as provided in SEQ ID NO:10,
   ii) a polypeptide comprising an amino acid sequence which is at least 67% identical to SEQ ID NO:10, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:11,
   ii) a polypeptide comprising an amino acid sequence which is at least 55% identical to SEQ ID NO:11, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:12,
   ii) a polypeptide comprising an amino acid sequence which is at least 59% identical to SEQ ID NO:12, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:13,
   ii) a polypeptide comprising an amino acid sequence which is at least 77% identical to SEQ ID NO:13, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:14,
   ii) a polypeptide comprising an amino acid sequence which is at least 50% identical to SEQ ID NO:14, and
   iii) a biologically active fragment of i) or ii),
wherein the polypeptide regulates fibre initiation and/or elongation.

In another aspect, the present invention provides a substantially purified polypeptide selected from the group consisting of:
   i) a polypeptide comprising an amino acid sequence as provided in SEQ ID NO:15, ii) a polypeptide comprising an amino acid sequence which is at least 64% identical to SEQ ID NO:15, and iii) a biologically active fragment of i) or ii), wherein the polypeptide regulates fibre initiation and/or elongation.

In another aspect, the present invention provides a substantially purified polypeptide selected from the group consisting of:

i) a polypeptide comprising an amino acid sequence as provided in SEQ ID NO:16, ii) a polypeptide comprising an amino acid sequence which is at least 50% identical to SEQ ID NO:16, and iii) a biologically active fragment of i) or ii), wherein the polypeptide regulates fibre initiation and/or elongation.

With regard to the polypeptide aspects, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Preferably, the polypeptide can be purified from a species of the Genus *Gossypium*.

Preferably, the polypeptide is a fusion protein further comprising at least one other polypeptide sequence.

In a preferred embodiment, the at least one other polypeptide is selected from the group consisting of: a polypeptide that enhances the stability of a polypeptide of the present invention, a polypeptide that assists in the purification of the fusion protein, and a polypeptide which assists in the polypeptide of the invention being secreted from a cell (particularly a plant cell).

In another aspect, the present invention provides an isolated polynucleotide comprising a sequence of nucleotides selected from the group consisting of:

i) a sequence of nucleotides as provided in SEQ ID NO:17;

ii) a sequence of nucleotides as provided in SEQ ID NO:18;

iii) a sequence encoding a polypeptide of the invention;

iv) a sequence of nucleotides which is at least 87% identical to SEQ ID NO:17 or SEQ ID NO:18; and v) a sequence which hybridizes to any one of i) to iv) under high stringency conditions, wherein the polynucleotide does not comprise a sequence of nucleotides as provided in SEQ ID NO:46.

In another aspect, the present invention provides an isolated polynucleotide comprising a sequence of nucleotides selected from the group consisting of:

i) a sequence of nucleotides as provided in SEQ ID NO: 19;

ii) a sequence of nucleotides as provided in SEQ ID NO:20;

iii) a sequence encoding a polypeptide of the invention, and iv) a sequence complementary to any one of i) to iii).

In another aspect, the present invention provides an isolated polynucleotide comprising a sequence of nucleotides selected from the group consisting of:

i) a sequence of nucleotides as provided in SEQ ID NO:21;

ii) a sequence of nucleotides as provided in SEQ ID NO:22;

iii) a sequence encoding a polypeptide of the invention;

iv) a sequence of nucleotides which is at least 54% identical to SEQ ID NO:21 or SEQ ID NO:22; and v) a sequence which hybridizes to any one of i) to iv) under high stringency conditions, wherein the polynucleotide does not comprise a sequence of nucleotides as provided in SEQ ID NO:47.

In another aspect, the present invention provides an isolated polynucleotide comprising a sequence of nucleotides selected from the group consisting of:

i) a sequence of nucleotides as provided in SEQ ID NO:23;

ii) a sequence encoding a polypeptide of the invention;

iii) a sequence of nucleotides which is at least 55% identical to SEQ ID NO:23; and iv) a sequence which hybridizes to any one of i) to iii) under high stringency conditions, wherein the polynucleotide does not comprise a sequence of nucleotides as provided in SEQ ID NO:48.

In another aspect, the present invention provides an isolated polynucleotide comprising a sequence of nucleotides selected from the group consisting of:

i) a sequence of nucleotides as provided in SEQ ID NO:24;

ii) a sequence of nucleotides as provided in SEQ ID NO:25;

iii) a sequence encoding a polypeptide of the invention;

iv) a sequence of nucleotides which is at least 50% identical to SEQ ID NO:24 or SEQ ID NO:25; and v) a sequence which hybridizes to any one of i) to iv) under high stringency conditions, wherein the polynucleotide does not comprise a sequence of nucleotides as provided in SEQ ID NO:49.

In another aspect, the present invention provides an isolated polynucleotide comprising a sequence of nucleotides selected from the group consisting of:

i) a sequence of nucleotides as provided in SEQ ID NO:26;

ii) a sequence of nucleotides as provided in SEQ ID NO:27;

iii) a sequence encoding a polypeptide of the invention;

iv) a sequence of nucleotides which is at least 50% identical to SEQ ID NO:26 or SEQ ID NO:27; and v) a sequence which hybridizes to any one of i) to iv) under high stringency conditions, wherein the polynucleotide does not comprise a sequence of nucleotides as provided in SEQ ID NO:50.

In another aspect, the present invention provides an isolated polynucleotide comprising a sequence of nucleotides selected from the group consisting of:

i) a sequence of nucleotides as provided in SEQ ID NO:28, ii) a sequence of nucleotides as provided in SEQ ID NO:29, iii) a sequence encoding a polypeptide of the invention, iv) a sequence complementary to any one of i) to iii).

In another aspect, the present invention provides an isolated polynucleotide comprising a sequence of nucleotides selected from the group consisting of:

i) a sequence of nucleotides as provided in SEQ ID NO:30;

ii) a sequence of nucleotides as provided in SEQ ID NO:31;

iii) a sequence encoding a polypeptide of the invention;

iv) a sequence of nucleotides which is at least 65% identical to SEQ ID NO:30 or SEQ ID NO:31; and v) a sequence which hybridizes to any one of i) to iv) under high stringency conditions, wherein the polynucleotide does not comprise a sequence of nucleotides as provided in SEQ ID NO:51.

In another aspect, the present invention provides an isolated polynucleotide comprising a sequence of nucleotides selected from the group consisting of:
i) a sequence of nucleotides as provided in SEQ ID NO:32,
ii) a sequence of nucleotides as provided in SEQ ID NO:33,
iii) a sequence encoding a polypeptide of the invention,
iv) a sequence complementary to any one of i) to iii).

In another aspect, the present invention provides an isolated polynucleotide comprising a sequence of nucleotides selected from the group consisting of:
i) a sequence of nucleotides as provided in SEQ ID NO:34;
ii) a sequence of nucleotides as provided in SEQ ID NO:35;
iii) a sequence encoding a polypeptide of the invention;
iv) a sequence of nucleotides which is at least 70% identical to SEQ ID NO:34 or SEQ ID NO:35; and
v) a sequence which hybridizes to any one of i) to iv) under high stringency conditions,
wherein the polynucleotide does not comprise a sequence of nucleotides as provided in SEQ ID NO:52.

In another aspect, the present invention provides an isolated polynucleotide comprising a sequence of nucleotides selected from the group consisting of:
i) a sequence of nucleotides as provided in SEQ ID NO:36;
ii) a sequence of nucleotides as provided in SEQ ID NO:37;
iii) a sequence encoding a polypeptide of the invention;
iv) a sequence of nucleotides which is at least 55% identical to SEQ ID NO:36 or SEQ ID NO:37; and
v) a sequence which hybridizes to any one of i) to iv) under high stringency conditions,
wherein the polynucleotide does not comprise a sequence of nucleotides as provided in SEQ ID NO:53.

In another aspect, the present invention provides an isolated polynucleotide comprising a sequence of nucleotides selected from the group consisting of:
i) a sequence of nucleotides as provided in SEQ ID NO:38;
ii) a sequence encoding a polypeptide of the invention,
iii) a sequence of nucleotides which is at least 65% identical to SEQ ID NO:38; and
iv) a sequence which hybridizes to any one of i) to iii) under high stringency conditions.

In another aspect, the present invention provides an isolated polynucleotide comprising a sequence of nucleotides selected from the group consisting of:
i) a sequence of nucleotides as provided in SEQ ID NO:39;
ii) a sequence of nucleotides as provided in SEQ ID NO:40;
iii) a sequence encoding a polypeptide of the invention;
iv) a sequence of nucleotides which is at least 95% identical to SEQ ID NO:39 or SEQ ID NO:40; and
v) a sequence which hybridizes to any one of i) to iv) under high stringency conditions,
wherein the polynucleotide does not comprise a sequence of nucleotides as provided in SEQ ID NO:54.

In another aspect, the present invention provides an isolated polynucleotide comprising a sequence of nucleotides selected from the group consisting of:
i) a sequence of nucleotides as provided in SEQ ID NO:41;
ii) a sequence of nucleotides as provided in SEQ ID NO:42;
iii) a sequence encoding a polypeptide of the invention;
iv) a sequence of nucleotides which is at least 50% identical to SEQ ID NO:41 or SEQ ID NO:42; and
v) a sequence which hybridizes to any one of i) to iv) under high stringency conditions,
wherein the polynucleotide does not comprise a sequence of nucleotides as provided in SEQ ID NO:55.

In another aspect, the present invention provides an isolated polynucleotide comprising a sequence of nucleotides selected from the group consisting of:
i) a sequence of nucleotides as provided in SEQ ID NO:43;
ii) a sequence of nucleotides as provided in SEQ ID NO:44;
iii) a sequence encoding a polypeptide of the invention;
iv) a sequence of nucleotides which is at least 65% identical to SEQ ID NO:43 or SEQ ID NO:44; and
v) a sequence which hybridizes to any one of i) to iv) under high stringency conditions,
wherein the polynucleotide does not comprise a sequence of nucleotides as provided in SEQ ID NO:56.

In another aspect, the present invention provides an isolated polynucleotide comprising a sequence of nucleotides selected from the group consisting of:
i) a sequence of nucleotides as provided in SEQ ID NO:45;
ii) a sequence encoding a polypeptide of the invention;
iii) a sequence of nucleotides which is at least 50% identical to SEQ ID NO:45; and
iv) a sequence which hybridizes to any one of i) to iii) under high stringency conditions,
wherein the polynucleotide does not comprise a sequence of nucleotides as provided in SEQ ID NO:57.

With regard to the polynucleotide aspects, it will be appreciated that % identity figures higher than those provided above will encompass preferred embodiments. Thus, where applicable, in light of the minimum % identity figures, it is preferred that the polynucleotide comprises a nucleotide sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further aspect, the present invention provides a catalytic polynucleotide capable of cleaving a polynucleotide according to the invention.

Preferably, the catalytic polynucleotide is a ribozyme.

In yet another aspect, the present invention provides an oligonucleotide which comprises at least 19 contiguous nucleotides of a polynucleotide according to the invention.

In another aspect, the present invention provides a double stranded RNA (dsRNA) molecule comprising an oligonucleotide according to the invention, wherein the portion of the molecule that is double stranded is at least 19 basepairs in length and comprises said oligonucleotide.

Preferably, the dsRNA is expressed from a single promoter, wherein the strands of the double stranded portion are linked by a single stranded portion.

In a further aspect, the present invention provides a vector comprising or encoding the polynucleotide according to the invention.

The vectors may be, for example, a plasmid, virus, transposon or phage vector provided with an origin of replication, and preferably a promotor for the expression of the polynucleotide and optionally a regulator of the promotor. The vector may contain one or more selectable markers, for example an ampicillin resistance gene in the case of a bacterial plasmid or a neomycin resistance gene for a mammalian expression vector. The vector may be used in vitro, for example for the production of RNA or used to transfect or transform a host cell. Preferably, the vector is capable of replication in a plant cell.

Preferably, the polynucleotide is operably linked to a plant ovule or fibre specific promoter.

In another aspect, the present invention provides a vector comprising or encoding oligonucleotide of the invention or the dsRNA molecule of the invention.

In a further aspect, the present invention provides a host cell comprising a vector according to the invention.

In a further aspect, the present invention provides a transgenic plant, the plant having been transformed with a polynucleotide according to the invention or an oligonucleotide of the invention.

In one embodiment, the polynucleotide is capable of expression to produce a polypeptide according to the invention.

In an alternate embodiment, the plant has been transformed such that it produces a catalytic polynucleotide of the invention, or a dsRNA molecule of the invention.

In a further embodiment, the polynucleotide, catalytic polynucleotide or dsRNA down-regulates the production of a polypeptide of the invention which is endogenously produced by the plant.

In a further aspect, the present invention provides a substantially purified antibody, or fragment thereof, that specifically binds a polypeptide of the invention.

In another aspect, the present invention provides a method of breeding a fibre producing plant, the method comprising performing a method according to the first, second or third aspects of the invention.

In a further aspect, the present invention provides a method of selecting from a breeding population a fibre producing plant with altered fibre initiation and/or elongation potential, the method comprising;
  i) crossing two plants which have differing potential to produce fibre,
  ii) performing a method according to the first, second or third aspects of the invention on progeny plants,
  iii) selecting a progeny plant with altered fibre initiation and/or elongation potential when compared to a parent plant.

In another aspect, the present invention provides a plant produced by a method of the invention.

In a further aspect, the present invention provides a seed of a plant, transgenic or otherwise, of the invention.

In a further aspect, the present invention provides fibre of a plant, transgenic or otherwise, of the invention.

In another aspect, the present invention provides a method of identifying an agent which alters fibre initiation and/or elongation of a fibre producing plant, the method comprising
  a) exposing a polypeptide which is at least 50% identical to any one of SEQ ID NO's:1 to 16 to a candidate agent, and
  b) assessing the ability of the candidate agent to modulate the activity of the polypeptide.

In a further aspect, the present invention provides a method of identifying an agent which alters fibre initiation and/or elongation of a fibre producing plant, the method comprising
  a) exposing a polypeptide which is at least 50% identical to any one of SEQ ID NO's:1 to 16 to a binding partner which binds the polypeptide, and a candidate agent, and
  b) assessing the ability of the candidate agent to compete with the binding partner for binding to the polypeptide.

Preferably, the binding partner is detectably labeled.

In a further aspect, the present invention provides a method of identifying an agent which alters fibre initiation and/or elongation of a fibre producing plant, the method comprising a) exposing a polynucleotide encoding a polypeptide which is at least 50% identical to any one of SEQ ID NO's:1 to 16 to a candidate agent under conditions which allow expression of the polynucleotide, and
  b) assessing the ability of the candidate agent to modulate levels of polypeptide produced by the polynucleotide.

In another aspect, the present invention provides a method of identifying an agent which alters fibre initiation and/or elongation of a fibre producing plant, the method comprising
  a) exposing a polynucleotide which is at least 50% identical to any one of SEQ ID NO's:17 to 45 to a candidate agent, and b) assessing the ability of the candidate agent to hybridize and/or cleave the polynucleotide.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Expression profiles of the candidate genes measured by microarrays. The plots on the left side (column A) represent the results from the DP16 time course experiment and the values plotted are the ratios relative to 0 dpa. The plots on the right side (column B) represent the results of multi-time point Lintless 4A/DP 16 comparisons and the values plotted are the ratios of Lintless 4A/DP16 at the corresponding dpa. The genes showing similar expression profiles are plotted together.

Figure 2:
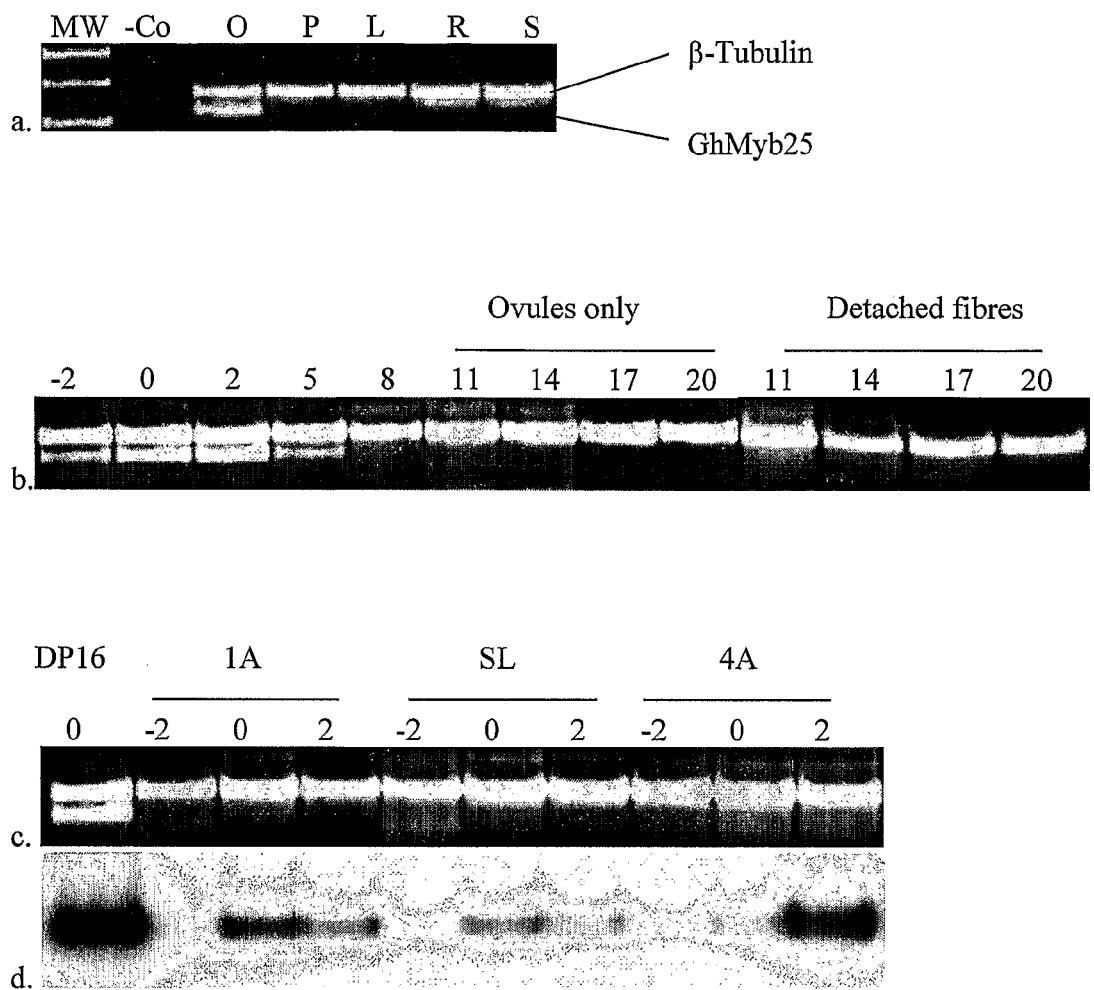

FIG. 2. RT PCR of GhMyb25 with β-tubulin as control.
  a. Different tissues from DP16. −Co: negative control, reaction without reverse transcriptase; O: 0 dpa ovule; P: petal; L: leaf; R: root; S: stem.
  b. Ovule and fibre from DP16. The numbers indicate the corresponding dpa.
  c. Ovule from 3 mutants. The numbers indicated the corresponding dpa.
  d. Southern blotting of the c. hybridised with an ON035F4 probe.

Figure 3:
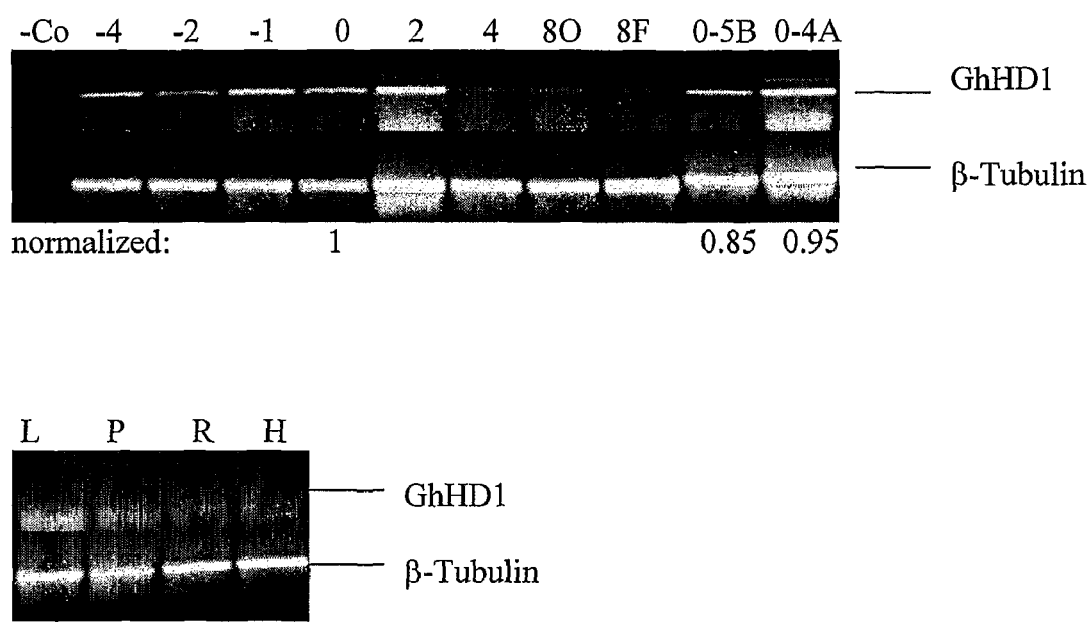

FIG. 3. RT-PCR of GhHD1 with β-tubulin as control. −Co: negative control, reaction without reverse transcriptase; −4 to 4: DP16 ovules of various stages (dpa) as indicated by the corresponding number; 8O: 8 dpa ovule of DP16 after fibres being removed; 8F: 8 dpa detached fibres of DP16; 0-5B: 0 dpa ovule form mutant 5B; 0-4A: 0 dpa ovule from mutant 4A; L: leaf; P: petal; R: root; H: hypocotyl.

Figure 4:
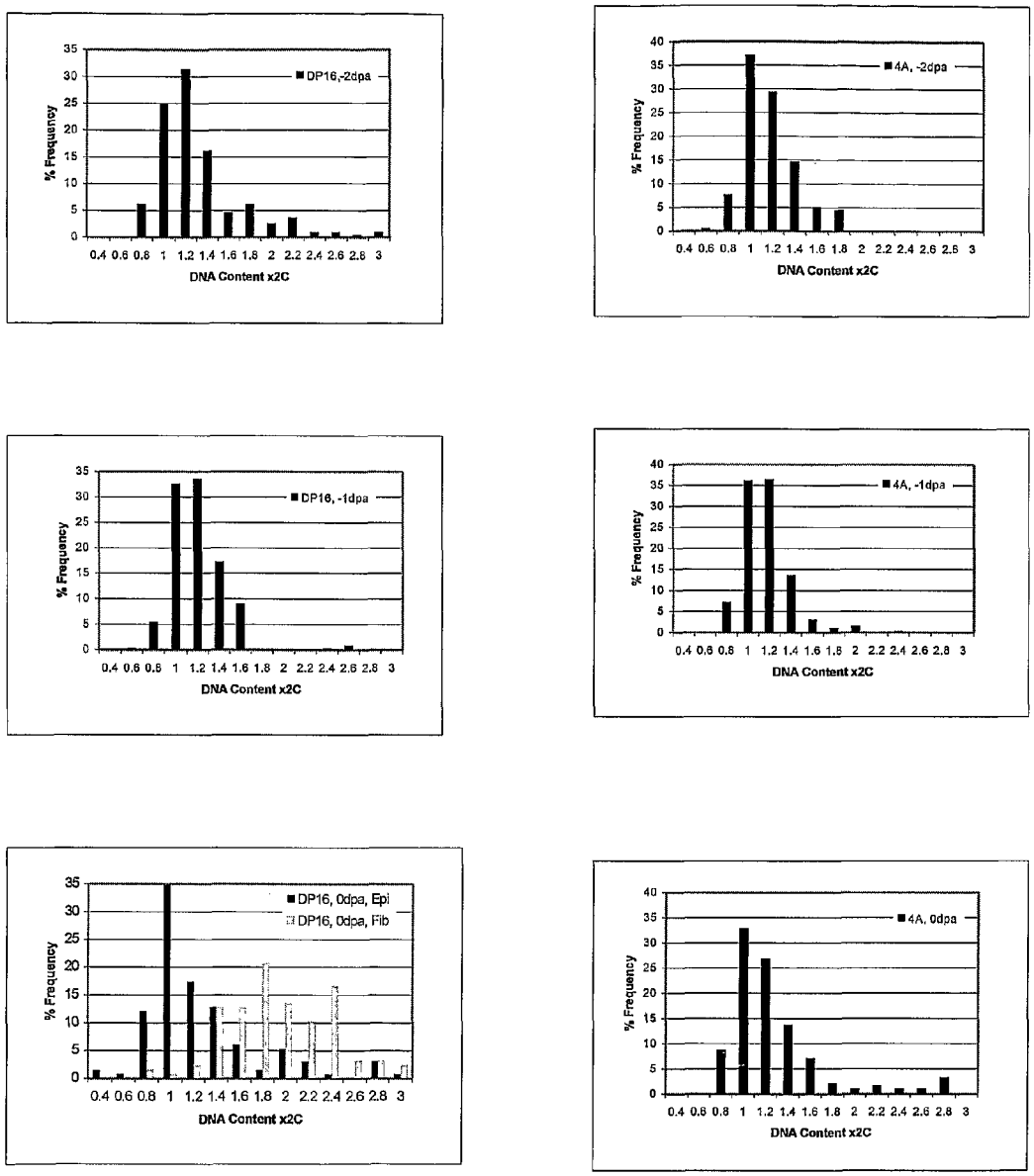

FIG. 4. Histograms of relative DNA contents of ovule epidermal cells and fibre cells.

KEY TO THE SEQUENCE LISTING

SEQ ID NO:1—Partial homeodomain like protein encoded by GhHD1 cDNA (clone ON033M7).
SEQ ID NO:2—Myb transcription factor like protein encoded by GhMyb25 cDNA (clone ON035F4).
SEQ ID NO:3—Partial cyclin D3 like protein encoded by GhCycD3;1 cDNA (clone OCF07F4).

SEQ ID NO:4—Partial protein encoded by GhFaE1 cDNA (clone ON035N9).
SEQ ID NO:5—Possible partial protein encoded by GhFU1 cDNA (clone ON035C9).
SEQ ID NO:6—Possible partial protein encoded by GhFU2 cDNA (clone ON005F1).
SEQ ID NO:7—α-expansion like protein cDNA (encoded in part by clone Pfs14x).
SEQ ID NO:8—Partial protein encoded by GhTMTP cDNA (clone CHX015K18).
SEQ ID NO:9—Sucrose synthase gene encoded by Ghsus cDNA (clone CHX002C10).
SEQ ID NO:10—Partial protein encoded by GhLTP cDNA (clone ON033M19).
SEQ ID NO:11—Protein encoded by GhLTP2 cDNA (clone OCF101D8).
SEQ ID NO:12—Partial protein encoded by GhMyb25-like cDNA (clone ON038N8).
SEQ ID NO:13—Protein encoded by GhRD22 cDNA (clone OCF005C10).
SEQ ID NO:14—Protein encoded by GhRD22-like cDNA (clone OCF010D8).
SEQ ID NO:15—Partial protein encoded by GhAsp cDNA (clone OCF008G9).
SEQ ID NO:16—Partial protein encoded by cDNA clone CHX007D1.
SEQ ID NO:17—GhHD1 cDNA (clone ON033M7).
SEQ ID NO:18—Coding region of GhHD1 cDNA (clone ON033M7).
SEQ ID NO:19—GhMyb25 cDNA (clone ON035F4).
SEQ ID NO:20—Coding region for GhMyb25 cDNA (clone ON035F4).
SEQ ID NO:21—GhCycD3;1 cDNA (clone OCF07F4).
SEQ ID NO:22—Coding region of GhCycD3;1 cDNA (clone OCF07F4).
SEQ ID NO:23—GhFaE1 cDNA (clone ON035N9) (entire clone coding region).
SEQ ID NO:24—GhFU1 cDNA (clone ON035C9).
SEQ ID NO:25—Coding region of GhFU1 cDNA (clone ON035C9).
SEQ ID NO:26—GhFU2 cDNA (clone ON005F1).
SEQ ID NO:27—Coding region of GhFU2 cDNA (clone ON005F1).
SEQ ID NO:28—α-expansin like clone Pfs14x.
SEQ ID NO:29—Coding region of α-expansin like clone Pfs14x.
SEQ ID NO:30—GhTMTP cDNA (clone CHX015K18).
SEQ ID NO:31—Coding region for GhTMTP cDNA (clone CHX015K18).
SEQ ID NO:32—Ghsus cDNA (clone CHX002C10).
SEQ ID NO:33—Coding region of Ghsus cDNA (clone CHX002C10).
SEQ ID NO:34—GhLTP cDNA (clone ON033M19).
SEQ ID NO:35—Coding region for GhLTP cDNA (clone ON033M19).
SEQ ID NO:36—GhLTP2 cDNA (clone OCF010D8).
SEQ ID NO:37—Coding region for GhLTP2 cDNA (clone OCF010D8).
SEQ ID NO:38—GhMyb25-like cDNA (clone ON038N8) (entire clone coding region).
SEQ ID NO:39—GhRD22 cDNA (clone OCF005C10).
SEQ ID NO:40—Coding region for GhRD22 cDNA (clone OCF005C10).
SEQ ID NO:41—GhRD22-like cDNA (clone OCF010D8).
SEQ ID NO:42—Coding region for GhRD22-like cDNA (clone OCF010D8).
SEQ ID NO:43—GhAsp cDNA (clone OCF008G9).
SEQ ID NO:44—Coding region for GhAsp cDNA (clone OCF008G9).
SEQ ID NO:45—cDNA clone CHX007D1 (entire clone coding region).
SEQ ID NO:46—Cotton EST BE052193.
SEQ ID NO:47—Cotton EST BQ412597.
SEQ ID NO:48—Cotton EST AI731943.
SEQ ID NO:49—Cotton EST BG442467.
SEQ ID NO:50—Cotton EST BQ403714.
SEQ ID NO:51—Cotton EST BG443329.
SEQ ID NO:52—Cotton EST BF275177.
SEQ ID NO:53—Cotton EST BQ410140.
SEQ ID NO:54—Cotton EST CA993037.
SEQ ID NO:55—Cotton EST BG441493.
SEQ ID NO:56—Cotton EST BQ402375.
SEQ ID NO:57—Cotton EST BQ413582.
SEQ ID NO's:58 to 64—Stem loop sequences of dsRNA molecules.
SEQ ID NO's:65 to 74—Oligonucleotide primers.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant physiology and biochemistry, immunohistochemistry, protein chemistry, and biochemistry).

Unless otherwise indicated, the recombinant protein, cell culture and others methods utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present), and are incorporated herein by reference.

As used herein, the term "gene" is to be taken in its broadest context and includes the deoxyribonucleotide sequences comprising the protein coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences". Introns are segments of a gene which are transcribed into nuclear RNA (hnRNA); introns may contain regulatory elements such as enhancers.

Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

A "polymorphism" as used herein denotes a variation in the nucleotide sequence of genes of the invention, between different species, cultivars, strains or individuals of a plant. A "polymorphic position" is a preselected nucleotide position within the sequence of the gene. In some cases, genetic polymorphisms are reflected by an amino acid sequence variation, and thus a polymorphic position can result in location of a polymorphism in the amino acid sequence at a predetermined position in the sequence of a polypeptide. Typical polymorphisms are deletions, insertions or substitutions. These can involve a single nucleotide (single nucleotide polymorphism or SNP) or two or more nucleotides.

A "deletion," as used herein, refers to a change in either amino acid or nucleotide sequence in which one or more amino acid or nucleotide residues, respectively, are absent.

An "insertion" or "addition," as used herein, refers to a change in an amino acid or nucleotide sequence resulting in the addition of one or more amino acid or nucleotide residues, respectively.

A "substitution," as used herein, refers to the replacement of one or more amino acids or nucleotides by different amino acids or nucleotides, respectively.

By "linked" or "genetically linked" it is meant that a marker locus and a second locus are sufficiently close on a chromosome that they will be inherited together in more than 50% of meioses, e.g., not randomly. Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM apart and most preferably about 0 cM apart.

The term "fibre" refers to plant cell types that share in common the features of having an elongated shape and abundant cellulose in thick cell walls, usually, but not always, described as secondary walls. Such walls may or may not be lignified, and the protoplast of such cells may or may not remain alive at maturity. Here the term "fibre" is used in its most inclusive sense, for example including: (a) thick-walled conducting and non-conducting cells of the xylem; (b) fibres of extraxylary origin, including those from ovary including the outer integument of the ovary, phloem, bark, ground tissue, and epidermis; and (c) fibres from stems, leaves, roots, seeds, and flowers or inflorescences. Such fibres have many industrial uses, for example in textiles, paper, sacking and boxing material, cordage, brushes and brooms, filling and stuffing, caulking, reinforcement of other materials, and manufacture of cellulose derivatives. In some industries, the term "fibre" is usually inclusive of thick-walled conducting cells such as vessels and tracheids and to fibrillar aggregates of many individual fibre cells. In a preferred embodiment, cotton fibre refers to the lint produced from the cotton boll (seed capsule) that is produced commercially. Cotton fibre also includes the short (about several mm) fibres sometimes referred to as "fuzz fibres". Preferred fibre producing plants include, but are not limited to, cotton (such as *Gossypium arboreum, Gossypium herbaceum, Gossypium barbadense* and *Gossypium hirsutum*), silk cotton tree (Kapok, *Ceiba pentandra*), desert willow, creosote bush, winterfal, balsa, ramie, kenaf, hemp (*Cannabis sativa*), roselle, jute, sisal abaca, flax, and horticultural plants such as grape, peach, pear, and apple.

As used herein, a "wild-type plant" is a plant that has not been altered by a method of the invention and/or does not comprise a transgene of the invention. When performing a method of the invention for altering fibre initiation and/or elongation, the manipulated plant is compared to a non-manipulated ("wild-type") member of the same species to determine the impact of the manipulation on fibre initiation and/or elongation.

In one embodiment, the term "altering fibre initiation and/or elongation" refers to increasing the number and/or size of the fibres. In another embodiment, the term "altering fibre initiation and/or elongation" refers to decreasing the number and/or size of the fibres. In a further embodiment, the term "altering fibre initiation and/or elongation" refers to modifying the timing of fibre initiation and/or elongation during development of the plant, for example to promote earlier or delayed initiation, or to regulate the synchrony of fibre initiation. As a result, in some instances it may be desirable to alter the activity of a molecule described herein to delay anthesis, whereas in other instances it may be desirable to alter the activity of a molecule described herein to promote anthesis.

As used herein, the term "around anthesis" refers to at least about 2 days either side of anthesis. In other words, +/−2 dpa.

As used herein: "transcription factors" modulate the level or timing of transcription of genes in the cells and may be tissue or organ specific; "regulatory proteins" regulate the expression level of genes in the cells, which may be at any of the transcriptional, post-transcriptional (e.g. stability of transcripts) or translational levels, and so encompass transcription factors; whereas "cell cycle proteins" are proteins that promote or retard cell division or processes leading to cell division. In this context, cell cycle proteins include proteins that promote DNA endoduplication. Transcription factors, regulatory proteins, or a cell cycle proteins, are also generally grouped herein as "anthesis regulatory proteins".

Detection of Impaired Genes and/or Gene Expression Levels

Any molecular biological technique known in the art which is capable of detecting a polymorphism/mutation/genetic variation or differential gene expression can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage, or a combination thereof (see, for example, Lemieux, 2000). The invention also includes the use of molecular marker techniques to detect polymorphisms closely linked to genes of the invention. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells expressing, or that should be expressing, a gene of the invention. However, it will generally be easier if PCR is performed on genomic DNA isolated from a plant.

A primer is an oligonucleotide, usually of about 20 nucleotides long, with a minimum of about 15 and a maximum of about 50 nucleotides, that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the induction of restriction enzyme or catalytic nucleic acid recognition/cleavage sites in specific target sequences. Primers may also contain additional sequences and/or modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., eds., Short Protocols in Molecular Biology, 3rd ed., Wiley, (1995) and Sambrook et al., Molecular Cloning, 2nd ed., Chap. 13, Cold Spring Harbor Laboratory Press, (1989). Sequencing can be carried out by any suitable method, for example, dideoxy sequencing, chemical sequencing or variations thereof. Direct sequencing has the advantage of determining variation in any base pair of a particular sequence.

Hybridization based detection systems include, but are not limited to, the TaqMan assay and molecular beacons. The TaqMan assay (U.S. Pat. No. 5,962,233) uses allele specific (ASO) probes with a donor dye on one end and an acceptor dye on the other end such that the dye pair interact via fluorescence resonance energy transfer (FRET). A target sequence is amplified by PCR modified to include the addition of the labeled ASO probe. The PCR conditions are adjusted so that a single nucleotide difference will effect binding of the probe. Due to the 5' nuclease activity of the Taq polymerase enzyme, a perfectly complementary probe is cleaved during PCR while a probe with a single mismatched base is not cleaved. Cleavage of the probe dissociates the donor dye from the quenching acceptor dye, greatly increasing the donor fluorescence.

An alternative to the TaqMan assay is the molecular beacon assay (U.S. Pat. No. 5,925,517). In the molecular beacon assay, the ASO probes contain complementary sequences flanking the target specific species so that a hairpin structure is formed. The loop of the hairpin is complimentary to the target sequence while each arm of the hairpin contains either donor or acceptor dyes. When not hybridized to a donor sequence, the hairpin structure brings the donor and acceptor dye close together thereby extinguishing the donor fluorescence. When hybridized to the specific target sequence, however, the donor and acceptor dyes are separated with an increase in fluorescence of up to 900 fold. Molecular beacons can be used in conjunction with amplification of the target sequence by PCR and provide a method for real time detection of the presence of target sequences or can be used after amplification.

Marker assisted selection is a well recognised method of selecting for heterozygous plants required when backcrossing with a recurrent parent in a classical breeding program. The population of plants in each backcross generation will be heterozygous for the gene of interest, normally present in a 1:1 ratio in a backcross population, and the molecular marker can be used to distinguish the two alleles. By extracting DNA from, for example, young leaves or shoots and testing with a specific marker for the introgressed desirable trait, early selection of plants for further backcrossing is made whilst energy and resources are concentrated on fewer plants.

Polypeptides

By "substantially purified polypeptide" we mean a polypeptide that has been at least partially separated from the lipids, nucleic acids, other polypeptides, and other contaminating molecules with which it is associated in its native state. Preferably, the substantially purified polypeptide is at least 60% free, preferably at least 75% free, and most preferably at least 90% free from other components with which they are naturally associated. Furthermore, the term "polypeptide" is used interchangeably herein with the term "protein".

The % identity of a polypeptide is determined by GAP (Needleman and Wunsch, 1970) analysis (GCG program) with a gap creation penalty=5, and a gap extension penalty=0.3. Unless stated otherwise, the query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. Even more preferably, the query sequence is at least 100 amino acids in length and the GAP analysis aligns the two sequences over a region of at least 100 amino acids.

As used herein, the term "biologically active fragment" refers to a portion of the defined polypeptide/enzyme which still maintains the ability to regulate fibre initiation and/or elongation. Such biologically active fragments can readily be determined by serial deletions of the full length protein, and testing the activity of the resulting fragment.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active or binding site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment, the polypeptides of the invention are transcription factors, regulatory proteins, or proteins that regulate the cell-cycle in the fibre producing plant. The transcription factors may be Myb transcription factors or homeodomain containing transcription factors, which are classes well known in the art.

Polynucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid molecule".

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides.

Whilst reasonable avenues have been pursued in an attempt to identify prior art, such as EST-type database entries, which disclose polynucleotides/polypeptides related to those of the claimed invention and ensure that such prior art molecules are excluded from the claims, there is the possibility that some relevant molecules have not been located. Such further prior art molecules (whether they be polynucleotides and/or polypeptides), if they exist, are also excluded from the polynucleotide or polypeptide claims of the invention.

Oligonucleotides of the present invention can be RNA, DNA, or derivatives of either. The minimum size of such oligonucleotides is the size required for the formation of a stable hybrid between an oligonucleotide and a complementary sequence on a nucleic acid molecule of the present invention. Preferably, the oligonucleotides are at least 15 nucleotides, more preferably at least 18 nucleotides, more preferably at least 19 nucleotides, more preferably at least 20 nucleotides, even more preferably at least 25 nucleotides in length. The present invention includes oligonucleotides that can be used as, for example, probes to identify nucleic acid molecules, primers to produce nucleic acid molecules or as agents to modify fibre initiation and/or elongation (e.g., as antisense-, triplex formation-, ribozyme- and/or RNA drug-based reagents). Oligonucleotide of the present invention used as a probe are typically conjugated with a label such as a radioisotope, an enzyme, biotin, a fluorescent molecule or a chemiluminescent molecule.

Polynucleotides and oligonucleotides of the present invention include those which hybridize under stringent conditions to a sequence provided as SEQ ID NO's: 17 to 45. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Antisense Polynucleotides

The term "antisense nucleic acid" shall be taken to mean DNA or RNA, or combination thereof, molecule that is complementary to at least a portion of a specific mRNA molecule of the invention and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Bourque lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition. The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 85%, preferably at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al., 1992) and the hairpin ribozyme (Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for the ribozymes of this invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

RNA Interference

RNA interference (RNAi) is particularly useful for specifically inhibiting the production of a particular protein. Although not wishing to be limited by theory, Waterhouse et al. (1998) have provided a model for the mechanism by which dsRNA can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene. The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at, least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the plant (preferably cotton) in which it is to be introduced, e.g., as determined by standard BLAST search.

Preferred loop ("single stranded") sequences are selected from, but not limited to, the group consisting of:

| (i) | CCC; | (SEQ ID NO: 58) |
|---|---|---|
| (ii) | UUCG; | (SEQ ID NO: 59) |
| (iii) | CCACC; | (SEQ ID NO: 60) |
| (iv) | CUCGAG; | (SEQ ID NO: 61) |
| (v) | AAGCUU; | (SEQ ID NO: 62) |
| (vi) and | CCACACC; | (SEQ ID NO: 63) |
| (vii) | UUCAAGAGA. | (SEQ ID NO: 64) |

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, cosuppression or double stranded RNA molecules may also comprise a largely double-stranded RNA region, preferably comprising a nuclear localization signal, as described in WO 03/076619. In a preferred embodiment, the largely double-stranded region is derived from a PSTVd type viroid or comprises at least 35 CUG trinucleotide repeats.

Transgenic Plants

The term "plant" refers to whole plants, plant organs (e.g. leaves, stems roots, etc), seeds, plant cells and the like. Plants contemplated for use in the practice of the present invention include both monocotyledons and dicotyledons. Preferably, the plant is a horticultural plant or cotton.

The term "cotton" as used herein includes any species of the genus *Gossypium* which is used for commercial fibre production, preferably *G. hirsutum* or *G. barbadense*.

Transgenic plants, as defined in the context of the present invention include plants (as well as parts and cells of said plants) and their progeny which have been genetically modified using recombinant techniques. This would generally be to either i) cause or enhance production of at least one protein of the present invention in the desired plant or plant organ, or ii) disrupt the production and/or activity of a polypeptide of the present invention. Transformed plants contain genetic material that they did not contain prior to the transformation. The genetic material is preferably stably integrated into the genome of the plant. The introduced genetic material may comprise sequences that naturally occur in the same species but in a rearranged order or in a different arrangement of elements, for example an antisense sequence. Such plants are included herein in "transgenic plants". A "non-transgenic plant" is one which has not been genetically modified with the introduction of genetic material by recombinant DNA techniques.

Several techniques exist for introducing foreign genetic material into a plant cell. Such techniques include acceleration of genetic material coated onto microparticles directly into cells (see, for example, U.S. Pat. No. 4,945,050 and U.S. Pat. No. 5,141,131). Plants may be transformed using *Agrobacterium* technology (see, for example, U.S. Pat. No. 5,177,010, U.S. Pat. No. 5,104,310, U.S. Pat. No. 5,004,863, U.S. Pat. No. 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques described herein.

A particularly preferred method of producing a transgenic cotton plant is by *Agrobacterium*-mediated transformation of cotyledons, followed by the induction of callus formation, and the subsequent induction of embryogenic callus, and regeneration into plants.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of plant promoters include, but are not limited to ribulose-1,6-bisphosphate carboxylase small subunit, beta-conglycinin promoter, phaseolin promoter, high molecular weight glutenin (HMW-GS) promoters, starch biosynthetic gene promoters, ADH promoter, heat-shock promoters and tissue specific promoters. Promoters may also contain certain enhancer sequence elements that may improve the transcription efficiency. Typical enhancers include but are not limited to Adh-intron 1 and Adh-intron 6.

Constitutive promoters direct continuous gene expression in all cells types and at all times (e.g., actin, ubiquitin, CaMV 35S). Tissue specific promoters are responsible for gene expression in specific cell or tissue types, such as the leaves or seeds (e.g., zein, oleosin, napin, ACP, globulin and the like) and these promoters may also be used. Promoters may also be active during a certain stage of the plants' development as well as active in plant tissues and organs. Examples of such promoters include but are not limited to pollen-specific, embryo specific, corn silk specific, cotton fibre specific, root specific, seed endosperm specific promoters and the like.

In a particularly preferred embodiment, the promoter directs expression around anthesis which is when fibre initiation and elongation occur. Thus, it is preferred that the promoter is an ovule or fibre specific promoter. Examples include promoters described in U.S. Pat. No. 5,495,070, U.S. Pat. No. 5,608,148 and U.S. Pat. No. 5,602,321.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used.

In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S) and the like may be used.

Vectors

One embodiment of the present invention includes a recombinant vector, which includes at least one isolated polynucleotide molecule of the present invention inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

One type of recombinant vector comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, other animal, and plant cells. Preferred expression vectors of the present invention can direct gene expression in plant cells.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

Host Cells

Suitable host cells to transform include any cell that can be transformed with a polynucleotide of the present invention. Host cells can be either untransformed cells or cells that are already transformed with at least one nucleic acid molecule (e.g., nucleic acid molecules encoding one or more proteins of the present invention). Host cells of the present invention either can be endogenously (i.e., naturally) capable of producing proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite, arthropod, animal and plant cells. Preferred host cells are plant cells, in particular cotton cells. In a preferred embodiment, the cells are ovule cells such as the cells of the outer integument of cotton ovules.

Antibodies

The invention also provides monoclonal or polyclonal antibodies to polypeptides of the invention or fragments thereof. Thus, the present invention further provides a process for the production of monoclonal or polyclonal antibodies to polypeptides of the invention.

The term "binds specifically" refers to the ability of the antibody to bind to proteins of the present invention but not other proteins obtained of the plant.

As used herein, the term "epitope" refers to a region of a protein of the invention which is bound by the antibody. An epitope can be administered to an animal to generate antibodies against the epitope, however, antibodies of the present invention preferably specifically bind the epitope region in the context of the entire protein.

If polyclonal antibodies are desired, a selected mammal (e.g., mouse, rabbit, goat, horse, etc.) is immunised with an immunogenic polypeptide. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies of the invention may be bound to a solid support and/or packaged into kits in a suitable container along with suitable reagents, controls, instructions and the like.

Preferably, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect proteins of the invention.

Assessing Fibre Properties

Fibres produced from plants of the invention are compared to control fibres (e.g., fibres from wild-type plants or plants transformed with marker nucleic acids) to determine the extent of modulation of fibre properties. Modulation of fibre properties, such as fibre number, length, strength, or fineness, is achieved when the percent difference in these fibre properties of the plants of the invention and control plants is at least about 10%, preferably at least about 20%, most preferably at least about 30%.

Several parameters can be measured to compare the properties or quality of fibres produced from plants of the invention to wild-type plants. These include: 1) fibre number, 2) fibre length; 3) fibre strength; and 4) fineness of fibres. A number of methods are known in the art to measure these parameters, such as described in U.S. Pat. No. 5,495,070. For example, instruments such as a fibrograph and HVI (high volume instrumentation) systems can be used to measure the length of fibres. The HVI systems can also be used to measure fibre strength. Fibre strength generally refers to the force required to break a bundle of fibres or a single fibre. In HVI testing, the breaking force is expressed in terms of "grams force per tex unit." This is the force required to break a bundle of fibres that is one tex unit in size. In addition, fineness of fibres can be measured, e.g., from a porous air flow test. In a porous air flow test, a weighed sample of fibres is compressed to a given volume and controlled air flow is passed through the sample. The resistance to the air flow is read as micronaire units. More specifically, the micronaire value is a measurement of cotton fibre quality that is a reflection of both fineness and maturity; low values indicate fine and/or immature fibre; high values indicate coarse and/or mature fibres. These values are determined according to standard techniques by measuring the resistance offered by a plug of cotton to airflow (supra) that is influenced by a combination of fineness and maturity. Fineness is the outside diameter of the fibre that is measured in mTex (Millitex or mg/km). Maturity is the degree of wall thickening of the fibre. Short fibre count (w) % refers to the percentage of short fibre weight; short fibre count (n) % refers to the percentage of short fibre yield. Immature fibre count refers to the number of immature fibres, i.e., fibres in which the thickening of the fibre wall is appreciably less than normal. An increase in fibre yield (fibre weight/seed) can be measured by using the Advanced Fibre Information System (AFIS). Using these and other methods known in the art, one of skill can readily determine the extent of modulation of fibre characteristics, quality and/or yield plants produced by the methods of the invention.

EXAMPLES

Example 1

Comparison of Fibre Initials Development in Wild-Type and Lintless Mutants of Cotton To identify genes that were specific to fibre initiation, genes were identified that were differentially expressed in early stage fertilised ovules of wild-type and lintless mutants of cotton that produce little if any fibres. The cotton lines (*Gossypium hirsutum* L.) used included two wild type cotton lines: Deltapine 16 (DP16) and Xu-142, and 6 lintless lines: Lintless 1A, Lintless 4A, Lintless 5B, Lintless 53, SL1-7-1 and fl. The 1A, 4A, 5B, 53 lines were obtained from the Queensland Department of Primary Industry Tropical Crops and Pastures Germplasm Collection and were originally selections from a linted cultivar B1278 isolated by Dr Alistair Low (unpublished, CSIRO Irrigation Research, Griffith, NSW). SL1-7-1 was obtained from USDA-ARS (College Station, Tex., USA). The Fuzzless-lintless, fl, isolated from Xu-142 background, and Xu-142 were provided by Prof. Xiao-Ya Chen (Institute of Plant Physiology, Chinese Academy of Science, Shanghai, China). All the cotton lines were grown in a glasshouse with temperature of 30° C./22° C.

(day/night). Ovules were always collected at a similar time each day (1-3 pm) and samples to be compared on a microarray were only used when they were collected on the same date and from the same glasshouse to minimise between time or location variability.

The mutants were of varying provenance but it is not known whether they are allelic. The four lines Lintless 1A, Lintless 4A, Lintless 5B, Lintless 53 were originally separate selections from a fully linted cultivar B1278 as spontaneous mutants that showed low but differing levels of lint production isolated as part of a breeding program to produce a cultivar with high quality seed oil and protein but with only a small amount of lint to retain the seeds in the boll capsule (Alistair Low, unpublished). Genetic complementation testing has not yet been carried out. SL 1-7-1 (Mississippi Obsolete Collection Number 0504) was also a naturally occurring variant (Turley and Ferguson, 1996) that produced less lint than the most lintless of the B1278 selections. All the mutant lines, but particularly 5B which had the most lint of any of the lines, show a variable, but low level of leakiness and this may be a result of environmental or physiological influences on lint production. At maturity the seeds of all of the mutant lines exhibit a fuzz-less phenotype (ie they have a completely naked seed and lack the short fuzz fibres covering the ovules of most Upland cotton varieties, including B1278). The growth rate and general vegetative and floral development of the mutants were similar to the wild type except that lintless 4A was slightly slimmer, and taller (about 20%) than the Deltapine 16 (DP16) variety used as the wildtype, whereas SL 1-7-1 (SL) exhibited higher levels of red anthocyanin pigments in all parts of the plant. All lines produced normal amounts of trichomes on their stems and leaves.

Scanning electron microscopy was used to examine the fibre development of the 5 lintless cotton mutants (Lintless 1A, 4A, 5B, 53 and SL) at two days before anthesis (−2 dpa), the day of anthesis (0 dpa) and two days after anthesis (2 dpa). Cotton ovules were collected using the phyllotactic arrangement of cotton flowering nodes and size of cotton flower buds as indicator of the development stage as described by Hasenfratz et al., (1995). The collected ovules were observed using an Oxford Conn. 1500 cryotrans system attached to a JEOL 6400 scanning electron microscope as described by Craig and Beaton (1996). There was generally no obvious difference between the mutants and the wild type (DP16) at −2 dpa except that 4A ovules were covered with mucous-like substances. The ovule surfaces were flat and epidermal cells were interspersed with stomata. On the day of anthesis, a few fibre initials became visible on the mutant ovules but these were considerably fewer in number than on wild type ovules. The mucous-like substances covering 4A ovule disappeared at this stage. The mutant phenotype was best revealed at two days post-anthesis when the fibres have begun to elongate. At this time, all of the mutants had a much reduced number of fibre initials on the surface of ovules and those fibres that had developed were slower to elongate and less synchronized in their elongation than the fibre initials of the wild type. The degree of lintlessness varied among the mutants with some lines showing very few fibre initials (Lintless 4A, 1A and 53) and the others more (Lintless 5B and SL-1-7-1), but still considerably fewer than DP16. Early fibre growth was sensitive to environmental conditions demonstrated by the more rapid fibre growth of the wild type cotton grown in glasshouses with a temperature regime of 30° C./22° C. (day/night) than in a glasshouse with temperature of 25° C./15° C.

Example 2

Differential Expression of Genes in the Mutant Ovules Compared to Wild-Type cDNA Library Construction CHX cDNA library was constructed using cycloheximide treated ovules. Cotton flower buds of developmental stages of −3 dpa, −2 dpa, −1 dpa and 0 dpa were detached and pooled from glasshouse grown cotton plants and surface sterilized by dipping in 70% ethanol and flaming twice. The cotton ovules were dissected out under sterile conditions and cultured on 15 ml of cotton ovule culture medium (Beasley and Ting, 1973) supplemented with 5 μM IAA (indole acetic acid) and 1 μM GA in 100 ml glass flasks at 29° C. in the dark overnight and then treated with 10 μM cycloheximide for 4 hours under the same culture conditions. After the cycloheximide treatment, the ovules were rinsed with sterile water, stored in RNAlater solution (Ambion) at −20° C. Total RNA was isolated using a method described by Wu et al. (2002). Purification of poly $A^+$ mRNA from total RNA was carried out using Qiagen Oligotex mRNA kit (Cat. No. 70042), following the manufacturer's protocol. In vitro translation was carried out to verify the bioactivity of the poly $A^+$ RNA (Wu et al. 2002). 5 μg poly $A^+$ mRNA from cycloheximide treated ovules was used for cDNA synthesis using a Life Technologies' Superscript Choice system (Cat. Series 18090) following the manufacturer's instructions. The first strand cDNA was synthesized using a mix of 1 μg Oligo(dT)12-18 primer and 50 ng of random hexamers. The EcoRI adapted cDNA was size-fractionated and cDNA longer than 500 bp was randomly cloned in λZipLox EcoRI arms (Life Technology Cat No. 15397-029). This library was comprised of 2×106 primary pfu with average insert size of 1.05 kb.

OCF cDNA library was developed from DP16 0 dpa ovules. The total RNA isolation and poly $A^+$ mRNA purification was the same as for CHX library construction. 5 μg poly $A^+$ mRNA was used for cDNA synthesis and cDNA library construction using a Life Technologies' Superscript lamda system (Cat. No. 19643-014) following the manufacturer's instructions. The first strand cDNA was synthesized using the NotI primer-adapter, in the presence of 1 μCi [$\alpha$-$^{32}$P] dCTP. The SalI adapted and NotI digested cDNA was size-fractionated and the cDNA longer than 500 bp was directionally cloned in λZipLox NotI-SalI arms (Life Technology Cat No. 15397-029). This primary library was comprised of 5×10$^5$ pfu with average insert size of 0.9 kb.

For both CHX and OCF libraries, the cDNA could be recovered in the autonomously-replicating plasmid pZL1 using a in vivo excision protocol provided by Life Technology. Two bacterial strains (Life Technology) were used for the excision: DH10B (ZIP) for the preparation of double stranded plasmid DNA, and DH12S (ZIP) for the preparation of single stranded DNA by infection with helper phage M13K07 (NEW ENGLAND BioLabs).

Normalization of the OCF Library

The OCF library was normalised using a method essentially as described by Bonaldo et al. (1996) with some modifications. Single-stranded plasmid DNA (ssDNA) was prepared from the excised OCF library using helper phage M13K07 (NEW ENGLAND BioLabs) and purified using the Bio-Gel HTP hydroxyapatite (HAP) column (Bio-Rad) according to Ali et al. (2000) with some modifications. The ssDNA was loaded on to a jacketed HAP column (Bio-Rad) at 60° C. and washed with 3 ml 10 mM Na-phosphate. The column was washed with 3 ml 0.16M Na-phosphate buffer and the eluate was collected in small fractions (about) 200 μl)

and $OD_{260}$ was measured for each of the fractions. The fractions with the highest OD measurements were pooled and desalted using a Qiaquick PCR purification kit (Qiagen). The driver DNA was prepared from the same excised OCF library by SalI and NotI digestion of the double-stranded plasmid and the gel-separated cDNA fragments (smear on the gel) was purified using a Qiaquick gel extraction kit (Qiagen). Hybridization of driver with ssDNA tracer was performed in the presence of a 5'-blocking oligo (5'-CCCACGCGTCCG-3') (SEQ ID NO:71), and a 3'-blocking oligo (5'-AAAAAAGGGCGGCC-3') (SEQ ID NO:72). The hybridization mix comprised 0.5 M NaCl, 10 mM Tris (pH 8.0), 1 mM EDTA, 2 μg double-stranded driver DNA, 0.2 μg ssDNA, 10 μg of each of the blocking oligos, and 25 μl formamide in a total volume of 50 μl. The driver DNA was heat denatured by boiling for 5 min prior to mixing with the rest of the components and the whole hybridisation mix was heated to 65° C. for 3 min and then incubated at 42° C. for 24 hours. The hybridisation mix was run through a HAP column under the same conditions as described for ssDNA purification to separate the ssDNA from the hybridised DNA. The conversion of purified ssDNA into double-stranded plasmid DNA and transformation of competent DH10B (Life Technology) was as described by Ali et al. (2000). The normalized library was designated the ON library consisting $10^5$ primary transformants with average insert size of 0.9 kb.

PCR Amplification of cDNA Clones and Microarray Preparation

The cotton ovule cDNA microarray comprises a total of 10410 cDNA clones. Except for 52 clones encoding known cotton genes provided by colleagues, and 13 clones of negative controls (non-plant genes, intron sequences etc.), the rest of the clones were randomly picked from the CHX, OCF and ON cDNA libraries, including 5496 clones from CHX library, 1149 clones from OCF library and 3700 clones from the ON library.

All the anonymous cDNA clones from the ovule cDNA libraries were PCR amplified in 96 well PCR plates (AB gene). The PCR reaction contained of 2 mM $MgCl_2$, 0.2 mM each of the dNTPs, 0.2 μM each of the M13/pUC forward and reverse primers, 1 unit Taq F2 DNA polymerase and 1×F2 buffer (BIOTECH International Limited) in a 50 μl reaction with 2 μl overnight cultured bacterial cells as template. A row of 12 samples from each PCR plate was verified by agarose gel electrophoresis. The PCR fragments were ethanol precipitated and resuspended in 10 μl 50% DMSO and 8 μl of the fragments was transferred to 384 well plates for microarray slide printing. The PCR fragments were arrayed onto CMT-GAPS coated microarray slides (Corning) using a Virtek ChipWriter Pro (Virtek Biotech) arrayer. Post-printing slide processing was performed by baking the slides at 80° C. for 3 hours as described in the manufacturer's technical manual.

Micoarray Analysis

Cotton ovules used for RNA isolation were kept in RNAlater solution (Ambion) at 4° C. overnight and then stored at −20° C. For separating the ovule outer integument from the inner tissues, ovules stored in RNAlater were used and the separation was performed under a microscope at room temperature. Total RNA isolations were performed using a method described by Wu et al., (2002). Purification of polyA$^+$ mRNA from total RNA was carried out using Oligotex mRNA kit (Qiagen, Cat. No. 70042), following the manufacturer's protocol. The cotton ovule cDNA microarray comprises a total of 10410 cDNA clones. Except for 52 clones encoding known cotton genes, the clones were randomly picked from cDNA libraries constructed from DP-16 ovules of −3 dpa to 0 dpa.

For microarray probe labelling, equal amounts of mRNA (0.5-1 μg) of two compared samples were reverse transcribed using Superscript II reverse transcriptase (Life Technologies), using a combination of 1 μg oligo(dT)12-18 primer and 6 μg random primers (Life Technologies) per reaction. The purification and Cy3-dUTP and Cy5-dUTP (Amersham Pharmacia Biotech) labelling of the first strand cDNA was essentially as described by Schenk et al., (2000). The labelled probes were combined and purified using a Qiaquick PCR purification kit. The conditions for slide hybridisation and washing were as described in the manufacturer's instruction manual (Corning, CMT-GAPS coated slides). The microarray images were scanned using a GenePix 4000A microarray scanner (Axon Instruments, Union Calif., USA). A typical microarray comparison consisted of 4 replicates unless otherwise specified. This included two biological replicates and each biological replication contained two dye-swapped hybridisations. In a time course comparison where RNA from DP16 ovules of −4 dpa, −2 dpa and +2 dpa were compared to RNA from 0 dpa DP16 ovules, most comparisons consisted of 4 replications as mentioned above, however, self-comparison of 0 dpa to 0 dpa comprised 3 biological replications.

Scanned microarray images were analysed using the GenePix Pro program (Axon Instruments, Union Calif., USA). Grids were predefined and manually adjusted to ensure optimal spot recognition and bad spots, eg. dust contamination etc., were flagged. Spots were quantified using the GenePix's fixed circle method, and medians of the fluorescence intensity of the red and green channels were used to calculate the ratio of the two channels. The data were $log_2$ transformed and normalised using a spatial normalization method described by Wilson et al., (2003). The data were then rescaled by dividing by an estimate of the median absolute deviation (Wilson et al., 2003) before running the "find differentially expressed gene" function of tRMA (tools for R Microarray Analysis available via http://www.pi.csiro.au/gena/). For a typical microarray comparison that consisted of 4 replications, the "find differentially expressed gene" function of tRMA was used to select differentially expressed genes from each of the replications separately, and the gene lists were then compared and genes occurring in at least 3 of 4 replications were classified as differentially expressed genes for this comparison.

Gene expression in 0 dpa whole ovules of each of the mutants was compared to the wild-type DP16 at the same stage using microarray analysis as described above to identify differentially expressed genes. The number of genes identified are shown in Table 2. Each experiment was replicated a number of times as both biological replicates and dye swap replicates. The total number of cDNA clones that are differentially expressed amongst the mutants compared to the wild-type varied significantly, from an average of 60 clones in the Lintless 4A/DP16 comparison up to an average of 243 clones in the Lintless 53/DP16 comparison. In addition, the proportion of cDNA clones that are up or down-regulated also varied amongst the mutants with 4 mutant lines (1A, 53, 5B and SL) showing a higher number of cDNA clones that were up-regulated than down-regulated, and vise versa for the mutant Lintless 4A. These results may reflect the diverse genetic backgrounds or different genetic lesions of the mutants in addition to the variable amounts of lint produced by each line.

TABLE 2

Number of cDNA clones that are up- or down-regulated in each of the mutants as compared to the wild type

| Comparison | Genes Differentially Expressed | Genes Up in Mutant | Genes Down in Mutant | Number of Replicates* | Minimal Reproducibility** |
|---|---|---|---|---|---|
| 4A/DP16 | 60 | 9 (15%) | 51 (85%) | 8 | 75% |
| 1A/DP16 | 67 | 48 (72%) | 19 (28%) | 8 | 75% |
| SL/DP16 | 102 | 88 (86%) | 14 (14%) | 6 | 83% |
| 5B/DP16 | 144 | 91 (63%) | 53 (37%) | 4 | 75% |
| 53/DP16 | 243 | 199 (82%) | 44 (18) | 4 | 75% |

*Replicates consist both biological and technical replications. Each biological replicate (a RNA isolation) comprises two dye-swaped technical replicates. Number of biological replicates = Total number of replicates/2.
**Genes identified as being significantly differentially expressed in at least 6 out of 8 or 3 out of 4 replicates (75%), or 5 out of 6 replicates (83%).

Example 3

Identification of Genes that are Differentially Expressed in Seed Coat Outer Integument of Lintless Mutants Since the collected embryos described above may already have been pollinated and zygote development initiated, a separate microarray comparison was made between the mRNAs of the outer integument and those of the inner ovule tissues of the wild-type cotton, to filter out those genes that were not expressed specifically in the seed coat outer integument where fibres are initiated. Cotton ovules at 0 dpa are rapidly developing complex organs, composed of at least three separable layers of tissues: the outer integument, the inner integument and the nucellus (including a developing zygote). The genes identified as being differentially expressed in the mutant/wild-type comparisons might be constitutively expressed throughout the whole ovule or they may be expressed in only one or two of the layers. As cotton fibres develop only from the epidermal cells of the outer integument, genes that showed a higher expression level in this layer should be more relevant to fibre initiation and development compared to the genes that are predominantly expressed in the inner integument and nucellus. Outer integuments were therefore separated from the inner integuments and nucellus of 0 dpa wild type ovules by microdissection and labeled cDNA prepared from the partitioned tissues as described above. The gene expression in the outer integument was then compared to that of the inner integument and nucellus by probing the ovule cDNA microarray. The results, averaged over four replicates (two biological replicates each consisting of two dye-swapped technical replicates) revealed a total of 120 cDNA clones that were differentially expressed with 65 clones up-regulated and 55 clones down-regulated in the outer integument of wild type ovules. The list of 65 outer integument up-regulated clones was then used as a filter on the differentially expressed gene lists identified from the lintless mutant/wild type comparisons to select for cDNA clones that were up-regulated in the outer integument. This filtering resulted in the identification of a surprisingly small number of genes: 4, 7, 6, 10, 4 genes from the 1A, 4A, 5B, 53 and SL mutants respectively that were both differentially expressed in mutant/wild type comparisons and up-regulated in the outer integument.

There was significant overlap of the cDNA clones amongst the different mutants and in total only 11 unique cDNA clones were identified from this experiment as potential candidate genes involved in early stage fibre development. The changes in relative expression in each mutant are summarized in Table 3.

Except for clone CHX007D10, which appears to be a chimeric clone, that was up-regulated in mutant Lintless 53, the rest of the clones were all down-regulated in the mutants. Three genes (corresponding to clones ON035F4, ON035N9, ON035C9) were down-regulated in all 5 mutants and the other clones are down-regulated in up to 4 of the mutants. Sequence analysis showed a range of genes that had not been identified or characterized previously as important in early fibre development, including two transcription factors (Gh-Myb25 and a gene encoding a putative homeodomain protein); a cyclin D3 homolog; a transferase protein; a transmembrane transporter and two genes of unknown biochemical function. For ease of referring to the different genes, we have assigned them gene names that refers to their presumed functions, such as GhHD1 to refer to the cotton homeodomain protein like gene represented by ON035N9 (Table 3).

TABLE 3

Genes that were up- or down-regulated in the lintless mutants and up-regulated in the outer integument[a]

| Name | Clone No | SL/DP | 1A/DP | 53/DP | 4A/DP | 5B/DP | OI/I I[c] | Most Homologous gene[d] |
|---|---|---|---|---|---|---|---|---|
| GhMyb25 | ON035F4 | −5.8 | −10.1 | −10.8 | −10.8 | −10.8 | 4.6 | (AF336283) GHMYB25 |
| GhFaEl | ON035N9 | −5.6 | −6.7 | −5.7 | −7 | −5.8 | 4.7 | (NP_195909) Transferase |
| GhFU1 | ON035C9 | −8.5 | −11 | −14.1 | −15.2 | −13.8 | 2.7 | Unknown |
| α-Expansin | Pfs14x | −6.8 | −7.6 | −9.1 | / | −9.1 | 3.3 | (AF512539) Alpha-expansin |
| GhFU2 | ON033F1 | / | / | −5.9 | −5.6 | −8.2 | 2.8 | Unknown |

TABLE 3-continued

Genes that were up- or down-regulated in the lintless mutants and up-regulated in the outer integument[a]

| Name | Clone No | SL/DP | 1A/DP | 53/DP | 4A/DP | 5B/DP | OI/I[c] | Most Homologous gene[d] |
|---|---|---|---|---|---|---|---|---|
| GhHD1 | ON033M7 | / | / | / | −5.5 | −4.9 | 2.8 | (T05850) Homeobox protein ATML1 |
| GhTMTP | CHX015K18 | / | / | / | −8.1 | −4.4 | 4.7 | (NP_175557) ATP-dependent transmembrane transporter |
| GhCycD3;1 | OCF07F4 | / | / | / | −5.3 | −3.7 | 4.9 | (AAQ19972) Cyclin D3 |
| CHX007D10[b] | CHX007D10 | / | / | 3.2 | / | / | 4.4 | (AC084282) Putative protein phosphotase/(BAB83948) CIG1 |
| GhSus | CHX002C10 | / | / | / | / | −3.5 | 4.6 | (AAD28641) Sucrose synthase |
| GhLTP | ON033M19 | / | / | / | / | −5.9 | 3.2 | (AAM62634) Lipid transfer protein |

[a]The values presented in the table are the medians of Log$_2$ transformed, normalized and rescaled ratios of the two compared samples. The rescaling was performed by dividing through by an estimate of the median absolute deviation (Wilson et al., 2003).
[b]Most probably a chimeric clone.
[c]OI: Outer Integument; II: Inner Integument and Nucellus.
[d]Most homologous gene based on the top BlastX identity score, with Genbank Accession No. and putative biochemical function.

Example 4

Expression Patterns of Genes in Wild-Type Developing Ovules

RNA from DP16 ovules of −4 dpa, −2 dpa and +2 dpa was compared to RNA from 0 dpa DP16 ovules using microarrays to profile the temporal changes in expression of genes around the time of fibre initiation (DP16 time course). RNA from −2 dpa and +2 dpa ovules from the Lintless 4A mutant, which shows more severe lintless phenotypes amongst the B1278 mutants, was compared with RNA from DP ovules of corresponding stages to reveal the temporal profiles of the genes inhibited in mutant 4A (4A/DP multi-time point comparison). The results of these experiments for the identified candidate genes are shown in FIG. 1.

The DP16 time course showed two classes of expression profiles: Class I genes showed peak expression at 0 dpa; while Class II genes exhibited increased expression towards +2 dpa (FIG. 1. Column A). Three genes, GhMyb25, the GHHD1 and GhCycD3;1, had a Class I expression profile suggesting a role in the early events of fibre initiation at anthesis. The expression of GhCycD3;1 increased continually from −4 dpa to 0 dpa and plateaued between 0 dpa and +2 dpa, while GhMyb25 and the GhHD1 exhibit a dip in expression at −2 dpa followed by a peak at 0 dpa and then a decline towards +2 dpa. The peak expression at 0 dpa of these three genes coincided with the time of fibre initiation. The rest of the genes all showed a Class II expression pattern although the specific details differed among them. The expression of GhFU1 and GhSus (sucrose synthase) increased gradually in the time period examined. GhFaE1 (transferase family) and the expression of GhTMTP (transmembrane transporter) showed a slight decrease from −4 dpa to −2 dpa and then increased gradually towards +2 dpa. The third group from this class comprised α-Expansin and GhLTP (lipid transfer protein) which show a distinctly flat profile from 4 dpa to 0 dpa followed by a sharp increase from 0 dpa to +2 dpa. The last member from this class, GhFU2, exhibited increased expression from −4 dpa to −2 dpa and again from 0 dpa to +2 dpa, while the expression between −2 dpa to 0 dpa remained unchanged.

The multiple time point comparisons of 4A/DP16 revealed the time and duration of up- or down-regulation of the genes in the 4A mutant relative to DP16 (FIG. 1. Column B). Among the Class I genes, none showed significant repression relative to DP16 at −2 dpa in 4A ovules, instead, the repression started after −2 dpa and reached the lowest level at 0 dpa for the GhHD1 and GhCycD3;1 genes, while GhMyb25 continued to decrease slightly after 0 dpa. Class II genes, in a similar fashion, did not show any significant repression at −2 dpa, and repression started after −2 dpa for most of the genes except GhSus, which only showed a later repression after 0 dpa. All the Class II genes exhibited repression at about +2 dpa. Three Class II genes, GhSus, α-Expansin and GhLTP, were not identified as differentially expressed genes in the initial 0 dpa 4A/DP comparisons. It became clear from this experiment that the repression of GhSus did not occur until after 0 dpa and only became significant at +2 dpa, while the repression of α-Expansin and GhLTP began after −2 dpa only became highly significant towards +2 dpa when fibres were rapidly elongating in the wild-type.

Example 5

Confirmation of Down-Regulation of Fibre Initiation Genes

The genetic background of the fibre mutants (B1278 and SL) used herein was not identical to that of the DP16 control used in the comparisons. Neither parental genotype was available for use in the experiments described above. While the differential expression of genes observed between the mutants and the wild-type might have arisen due to differences in the genetic backgrounds of the plants, the commonality of the genes identified among the different mutants and the fact that some have been characterized previously as important for fibre development using different strategies, suggested otherwise. A fuzzless-lintless (fl) mutant had recently been isolated from the Chinese *G. hirsutum* cultivar Xu-142 and used to identify and characterize fibre development related genes (Yu et al., 2000, Li et al., 2002, Ji et al., 2003). These two lines provided an isogenic pair with which to validate the genes identified from the other mutants. RNA from 0 dpa ovules of fl was compared to that of 0 dpa ovules of Xu-142 and 119 clones were identified as differentially expressed in four replicates. The same outer/inner integument gene expression filter as described above was applied to the data set and identified 13 differentially expressed genes that were also up-regulated in the outer integument of DP16 ovules. Amongst the 13 genes, 8 were in common with genes identified in the other lintless mutant/DP16 comparisons and the results are presented in Table 4. This comparison also revealed 5 additional genes that had not been identified in the previous 5 mutants. One of the cDNA clones, ON038N8 (886 bp), encodes a Myb protein which was 69% identical to the GhMyb25 protein. Other genes include two different RD22 genes, a second LTP and a putative L-asparaginase.

Reverse transcription-polymerase chain reaction (RT-PCR) assays were used to analyse expression of the gene as follows. Total RNA samples isolated from cotton tissues were DNase (RQ1 RNase-free DNase, Promega) treated and 0.5 μg of the total RNA was used in a RT-PCR reaction. The first strand cDNA synthesis was performed using SuperScript II reverse transcriptase and buffer supplied by the manufacturer (Life Technologies). The RT-PCR reaction was performed essentially as described by McFadden et al., (2001). The cotton β-tubulin gene was used as a control in all the RT-PCR reactions. The forward and reverse primers used for β-tubulin are 5'-AGAACATGATGTGTGCTGC-3' (SEQ ID NO:65) and 5'-AGCTGTGAACTGCTCACTC-3' (SEQ ID NO:66) respectively and the resulting cDNA fragment was 300 bp. The forward and reverse primers used for GhMyb25 RT-PCR were: 5'-TCAAACCCTCCTCAAAGCAACC-3' (SEQ ID NO:67) and 5'-ATTCCATTACCAGACGATGATGAC-3' (SEQ ID NO:68) respectively and this produced a cDNA fragment of 224 bp. The GhMyb25 and β-tubulin RT-PCR

TABLE 4

Genes differentially expressed in fl as compared to Xu-142

| Name | Clone No | fl/Xu-142** | Most Homologous gene*** |
|---|---|---|---|
| α-Expansin* | Pfs14x | −11.5 | (AF512539) Alpha-expansin |
| GhFU1* | ON035C9 | −9.8 | Unknown |
| GhMyb25* | ON035F4 | −9.0 | (AF336283) GHMYB25 |
| GhFU2* | ON003F1 | −7.8 | Unknown |
| GhFaE1* | ON035N9 | −7.4 | (NP_195909) Transferase |
| GhHD1* | ON033M7 | −6.1 | (T05850) Homeobox protein ATML1 |
| GhLTP* | ON033M19 | −4.9 | (AAM62634) Lipid transfer protein |
| GhTMTP* | CHX015K18 | −3.7 | (NP_175557) ATP-dependent transmembrane transporter |
| GhMyb25-like | ON038N8 | −4.4 | (AF336283) GHMYB25 |
| GhRD22 | OCF005C10 | −4.4 | (AAL67991). Dehydration-induced protein RD22 |
| GhAsp | OCF008G9 | −3.4 | (BAC66615) L-aspraginase |
| GhLTP2 | OCF010D8 | 3.4 | (CAA65477) Non-specific lipid-transfer protein |
| GhRD22-like | OCF006C1 | 5.3 | (BAC22498) Resistant specific protein-1 |

*Genes in common with the candidate genes from the other 5 mutants.
**The values presented in the table are the medians of Log₂ transformed, normalized and rescaled ratios of the two compared samples. The rescaling was performed by dividing through by an estimate of the median absolute deviation (computed on the final residual mean-difference data) as described by Wilson et al., (2003).
***Based on the top BlastX hit.

Example 6

Characterisation of GhMyb25 Expression

The nucleotide sequence of the clone ON035F4 was obtained. It was 1160 nucleotides in length with a coding region from nucleotides 68 to 995, encoding a protein which was 98% identical at the amino acid level to GhMyb25 (AF336283), expressed in 0 dpa ovules of *G. hirsutum* cultivar Acala Maxxa (Benjamin Burr, in Genbank). The encoded protein was an R2R3 type of Myb transcription factor. It was also 96% identical to the *G. arboretum* EST (BE054276, suggesting that it was from the A-genome present in tetraploid cotton. Outside the R2R3 region, which is highly conserved amongst all Myb transcription factors, GhMyb25 showed highest homology to the *Petunia hybrida* MYB.Ph3 and *Antirrhinum majus* MIXTA (AmMIXTA) than to *Arabidopsis* GL1 and cotton MYBA, another cotton myb which caused distinct abnormalities when over expressed in transgenic tobacco including the production of cotyledonary trichomes (Payne et al., 1999). The sequence of GhMyb25 currently in Genbank (AF336283) contained an unspliced intron that was not present in our clone (nucleotides 201-282 of AF336283).

reactions were performed in a one-tube reaction amplified with an initial denaturation cycle at 95° C. for 3 min followed by 23 cycles at 95° C. for 15 sec, 55° C. for 15 sec, 72° C. for 1 min and with a final cycle of 72° C. for 2 min. 5 μl of the RT-PCR reaction was checked on a 2% agarose gel and the gel was Southern-blotted to Hybond-N⁺ membrane (Amersham Pharmacia Biotech) and hybridized with $^{32}$P labelled probe derived from the cDNA clone of GhMyb25.

GhMyb25 expression was detected in 0 dpa wild-type ovules and not in petal, leaf and stem using RT-PCR (FIG. 2, panel a). GhMyb25 expression was detected in −2, 0, 2 and 5 dpa ovules with highest expression in 0 and 2 dpa ovules (FIG. 2, panel b). No expression of GhMyb25 was visible in ovules of −2, 0 and 2 dpa from three of the lintless mutants, 1A, SL1-7-1 and 4A (FIG. 2, panel c) although very low expression in the mutant ovules was revealed after hybridizing RT-PCR products with an ON035F4 probe (FIG. 2, panel d), consistent with the low levels of lint production that still occurs on these ovules. GhMyb25 expression peaked at 0 dpa in lines 1A and SL1-7-1, whereas in 4A, the highest expression was detected slightly later at 2 dpa.

Example 7

Characterisation of the Homeodomain Protein Gene GhHD1

ON033M7, a partial cDNA clone of 442 nucleotides, was extended by RT-PCR to 2207 nucleotides (without polyA tail), and encodes a protein with homology to two homeodomain proteins; protodermal factor 2 (Genbank: NP_567274) (507/634 or 79% identical amino acids) and the L1-specific and ovule specific homeodomain gene ATML1 (Genbank: T05850) (518/657, 78% identical). ATML1 has been grouped with the *Arabidopsis* GLABRA2 in the same HD-GL2 class and they also share a common L1 layer-specific or dermal-specific pattern of expression (Lu et al., 1996). The cotton gene was designated GhHD1. GhHD1 is only 43% and 42% identical to the other cotton homeodomain proteins that are present in Genbank, GhHOX1 (AAM97321) and GhHOX2 (AAM97322), respectively.

RT-PCR experiments were carried out to analyse expression, in similar fashion to those described above. The forward and reverse primers used for the GhHD1 RT-PCR were: 5'-GCTTTCTCTTGGATCAG-3' (SEQ ID NO:69) and 5'-CAATAACACATGAAACCAG-3' (SEQ ID NO:70) respectively and these resulted in a cDNA fragment of 384 bp. The GhHD1 and β-tubulin RT-PCR reactions were performed separately under the conditions described above. 10 µl of the RT-PCR reaction was electrophoresed on a 2% agarose gel and the gel was Southern-blotted to Hybond-N+ membrane (Amersham Pharmacia Biotech) and hybridized with $^{32}$P-labelled probe derived from the cDNA clone of the putative homeodomain gene. Since the expression of the β-tubulin appeared to be variable in different cotton tissues, the quantification of the GhHD1 expression using α-tubulin gene as a standard was only performed on the 0 dpa ovules of different cotton lines using an Image-Quant program (Molecular Dynamics).

GhHD1 was mainly expressed in ovules of various developmental stages and at much lower levels in leaves as revealed by RT-PCR (FIG. 3). The expression increased at −1 dpa and remained high till 2 dpa. Low expression levels were observed in 4 dpa ovules (with fibres attached), 8 dpa ovules (without fibres) and 8 dpa detached fibres. The expression levels of 0 dpa ovules of mutants 5B and 4A relative to DP16 0 dpa ovules after normalization with β-tubulin expression is shown in FIG. 3. The expression in the mutant ovules was slightly reduced in 5B and remained similar to wild-type in 4A ovules. The RT-PCR band was confirmed as GhHD1-specific by Southern blot hybridization using the ON033M7 cDNA fragment as probe.

Example 8

Characterisation of Other Genes

The characteristics of the genes identified in this study are summarized in Tables 5 and 6.

Clone OCF07F4 encoded a cyclin D3, similar to AAQ19972, 106/149 similar amino acids, 71%).

TABLE 5

Characteristics of fibre initiation genes identified from cotton ovules.

| Designation | Clone No | Length (nt*) | Full Length Or Partial? | Translation start/stop | Translation product size |
|---|---|---|---|---|---|
| GhMyb25 | ON035F4 | 1160 | F | 68/995 | 309 |
| GhFaEl | ON035N9 | 704 | P | — | at least 234 |
| GhFU1 | ON035C9 | 548 | F | 50/371 | 107 |
| α-Expansin | Pfs14x[b] | 835 | P | ?/766 | 255 |
| GhFU2 | ON003F1 | 727 | P | ?/563 | 113 |
| GhHD1 | ON033M7 | 2222 | P | ?/1873 | 624 |
| GhTMTP | CHX015K18 | 985 | P | ?/572 | 191 |
| GhCycD3; 1 | OCF07F4 | 600 | P | ?/453 | 151 |
| CHX007D10[c] | CHX007D10 | | Chimerical ? | — | |
| GhSus | CHX002C10 | 2611 | F | 8/2423 | 805 |
| GhLTP | ON033M19 | 732 | F | 10/595 | 195 |
| GhMyb25-like | ON038N8 | 886 | P | ?/887 | 295 |
| GhRD22 | OCF005C10 | 1353 | F | 58/1180 | 374 |
| GhAsp | OCF008G9 | 1024 | P | ?/796 | 265 |
| GhLTP2 | OCF010D8 | 610 | F | 33/402 | 123 |
| GhRD22-like | OCF006C1 | 1373 | P | ?/1213 | 404 |

*Omitting polyA sequence if present.

TABLE 6

Summary of closest match for the cotton ovule genes.

| Name | Clone No | Most Homologous gene (BlastX)[a] | Percentage Identity by BlastX (Similarity)[a] | Accession No. of nearest match (BlastN)[b] | Percentage identity (No. of matched nucleotides) | Percentage identity over fill length |
|---|---|---|---|---|---|---|
| GhMyb25 | ON035F4 | (AF336283) GHMYB25 [*Gossypium hirsutum*] | 98% (98%) | AF336283 *G. hirsutum* GHMYB | 99% (951/964) | 99% |
| GhFaEl | ON035N9 | (NP_195909) Transferase family [*Arabidopsis thaliana*] | 54% (72%) | NM_120367.2| *A. thaliana* transferase | 81% (88/108) | 58% |

TABLE 6-continued

Summary of closest match for the cotton ovule genes.

| Name | Clone No | Most Homologous gene (BlastX)[a] | Percentage Identity by BlastX (Similarity)[a] | Accession No. of nearest match (BlastN)[b] | Percentage identity (No. of matched nucleotides) | Percentage identity over fill length |
|---|---|---|---|---|---|---|
| GhFU1 | ON035C9 | none | none | AF027686 *Onobrychis viciifolia* | 81% (89/109) | 50% |
| α-Expansin | Pfs14x | (AF512539) Alpha-expansin precursor [*Gossypium hirsutum*] | 99% | AF043284 *G. hirsutum* expansin | 99% (828/836) | 99% |
| GhFU2 | ON003F1 | none | none | none | none | — |
| GhHD1 | ON033M7 | (T05850) Homeobox protein ATML1 [*Arabidopsis thaliana*] | 86% (93%) | NM_116727.2|; *A. thaliana* homeodomain | 79% (482/605) | 70% |
| GhTMTP | CHX015K18 | (NP_175557) ATP-dependent transmembrane transporter [*Arabidopsis thaliana*] | 65% (86%) | NM_104024.2| | 87% (68/78) | 63% |
| GhCycD3; 1 | OCF07F4 | (AAQ19972) Cyclin D3-2 [*Euphorbia esula*] | 53% (71%) | NM_119579.2| | 91% (31/34) | 52% |
| CHX007D10 | CHX007D10 | (BAB83948) proline oxidase/dehydrogenase | | AY492003.1| *G. max* proline dehydrogenase | 80% (120/149) | 40% |
| GhSus | CHX002C10 | (AAD28641) Sucrose synthase [*Gossypium hirsutum*] | 94% (95%) | U73588 *G. hirsutum* sucrose synthase | 98% (2443/2482) | 98% |
| GhLTP | ON033M19 | (AAM62634) Lipid transfer protein, putative [*Arabidopsis thaliana*] | 66% (83%) | none | none | |
| GhMyb25-like | ON038N8 | (AF336283) GHMYB25 [*Gossypium hirsutum*] | 58% (64%) | AF336283 *G. hirsutum* GHMYB | 94% (64/68) | 63% |
| GhRD22 | OCF005C10 | (AAL67991) Dehydration-induced protein RD22 [*Gossypium hirsutum*] | 76% (80%) | AY072821.1| *G. hirsutum* dehydration induced | 94% (810/864) | 94% |
| GhAsp | OCF008G9 | (BAC66615) L-aspraginase [*Glycine max*] | 63% (76%) | AP006428.1| *Lotus corniculatus* Chromosome5 complete sequense 127049bp | 93% (56/60) | |
| GhLTP2 | OCF010D8 | (CAA65477) Non-specific lipid-transfer protein [*Prunus dulcis*] | 54% (74%) | AF519812.1| *Nicotiana tabacum* | 91% (41/45) | 54% |
| GhRD22-like | OCF006C1 | (BAC22498) Resistant specific protein-1 [*Vigna radiata*] | 43% (60%) | none | 30/32, coincidental | |

[a]BlastX determines the percentage amino acid identity (% similarity in parentheses) over the region of closest match to the Genbank database.
[b]BlastN determines the nearest match at the nucleotide level in the Genbank database.

Example 9

Fibre Cells Undergo DNA Endoreduplication During Initiation

The observation that a cyclin D3 gene encoded by clone OCF007F4 was down-regulated in 0 dpa ovules of mutants 4A and 5B compared to DP16 prompted the inventors to investigate the cell division and DNA replication activities of the epidermal layers of DP16 and lintless 4A ovules. Ovules of cotton line DP16 and 4A at −2, −1, and 0 dpa stages were fixed in 3:1 (95% ethanol:acetic acid) for 1 hr at room temperature, cleared in 95%/1 mM $MgCl_2$ ethanol over night at room temperature and rehydrated through an ethanol series to 10 mMTris/1 mM $MgCl_2$ according to Szymanski and Marks (1998). The ovules were stained in 0.1 μg/ml propidium iodide for 30 seconds and than distained and kept in 10 mMTris/1 mM $MgCl_2$.

Nuclear DNA content of ovule epidermal and fibre cells at the chalazal end were measured using a Leica SP2 confocal laser scanning microscope (Leica, Wetzler, Germany). At least 200 nuclei were measured from each sample which consisted of at least 3 ovules. Fluorescence at 600-740 nm was collected after excitation at 488 and 543 nm using a 63×NA 1.25 water-immersion lens. After optically sectioning through the ovule epidermis, the mean fluorescence intensity and dimensions of epidermal and fibre cell nuclei was measured from the maximum projection of the optical stack. Total fluorescence of individual nuclei was calculated by multiplying nuclear area by average fluorescence. This value was converted to a ratio by normalising against total fluorescence of epidermal cell nuclei at telophase or anaphase (2C) within the same image. The normalized values were then used to construct histograms of epidermal and fibre cell nuclear DNA content.

Since fibre cells are known to cease dividing after differentiation, the ovule epidermal cell division activities of DP16 and 4A-183 were examined at and before anthesis. Over the period examined (−2, −1 and 0 dpa), the extent of cell division in the ovule epidermis of lintless 4A and DP16 were not significantly different (paired t-test, P=2.1%) although the division rate in 4A was slightly higher than in DP16 (Table 7). It appears that the ovule epidermis division rates are higher at −1 dpa for both DP16 and 4A, although the significance of this is unclear.

TABLE 7

Cell division rates in ovule epidermal cells of DP16 and mutant 4A

| DPA | DP16 | 4A |
|---|---|---|
| −2 dpa | 2.78% | 2.97% |
| −1 dpa | 3.25% | 3.5% |
| 0 dpa | 2.69% | 2.84% |

Relative DNA contents of the epidermal cells and fibre cells were also measured, and normalized using DNA contents of nuclei at anaphase or telophase (2C) and the results are presented in FIG. 4. Since the pre-fibre initials and epidermal cell are visually indistinguishable at −2 and −1 dpa, the data for those times are presented as total epidermal cells. The results indicate that epidermal pavement cells of DP16 and Lintless 4A at these time points have a DNA content peak around 2 to 2.4 C, while differentiated fibre initials of DP16 when clearly distinguishable at 0 dpa, have an increased DNA content with the majority of cells showing a DNA content between 2.8 C and 5.2 C. While this result clearly suggests that the majority of fibre cells undergo at least one round of DNA endoreduplication during initiation, the involvement of the cyclin D3 gene in this process still needs to be verified.

Example 10

Cloning of Full-Length cDNA Sequences and Genes Encoding Therefor

At least two approaches can be used to determine the full length sequence of partial cDNA clones described herein.

One method is to screen a cDNA library, such as the cotton DP-16 ovule −3 dpa to 0 dpa library described herein, with a radioactively labelled polynucleotide which comprises the known portion of the cDNA. Library screening is performed as described by Sambrook et al., (supra), or other techniques known to those of skill in the art.

In another method, two primers of about 17 to about 20 nucleotides derived from both ends of the known partial sequence are synthesized and used to amplify the desired cDNA from a population of cDNA reverse transcribed with a poly-T comprising primer from mRNA obtained from, for example, cotton DP-16 ovule −3 dpa to 0 dpa. The polymerase chain reaction (PCR) is carried out under routine conditions, for instance, in 25 µl of reaction mixture with 0.5 µg of the above cDNA mixture. A convenient reaction mixture is 1.5-5 mM $MgCl_2$, 0.01% (w/v) gelatin, 20 µM each of dATP, dCTP, dGTP, dTTP, 25 µmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight (as determined by Northen blot analysis) is excised and purified. The PCR product is verified to be the selected sequence by subcloning and sequencing the DNA product.

Several other methods are available for the identification of the 5' or 3' ends of an mRNA sequence. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length cDNA.

To clone the corresponding gene of a cDNA described herein, a cotton genomic library is made in a λ vector and plaques obtained by plating $10^6$ or more λ infectious particles at high density in a suitable E. Coli host. The plaques are transferred to nylon filters. A gene specific probe designed considering the polynucleotides provided herein is labelled with radioactive label and used to hybridise to the nylon filters. Plaques corresponding to spots of hybridisation are isolated and confirmed to be positive for desired sequence by second or third rounds of hybridisation. DNA sequencing of the gene segments in the λ clones is carried out by standard methods to determine the full nucleotide sequence of the gene and the flanking upstream and downstream regions.

Example 11

Up-Regulation of Genes in the Fibre Initials Compared to Epidermal Cells

To investigate whether the differentially expressed genes described above such as GhMyb25 and GhHD1 were expressed in fibre initials on the day of anthesis, laser capture microdissection (LCM) was used to isolate fibre initial cells and epidermal cells from sections of 0 dpa DP16 ovules, as follows. Ovaries of DP16 were fixed in 75% (v/v) ethanol and 25% (v/v) acetic acid immediately on ice after the ovaries were dissected from 0 dpa flowers and ovary wall removed. The subsequent infiltration of the fixative, 10% (w/v) sucrose and 15% (w/v) sucrose was as described by Nakazono et al. (2003). The ovaries were then embedded in TissueTek OCT (Sakura Finetechnical, Tokyo, Japan), frozen immediately on brass stubs and sectioned at 40-50 µm in a cryomicrotome (Model CT1, International Equipment Co., Nedham Heights, USA). The tissue sections were mounted on polylysine coated slides (Polysine, Biolab Scientific, Australia) air-dried and then dehydrated for 1 min in each of 70%, 95% and 100% ethanol on ice. The slides were then stored at −80° C. The PALM laser capture system (P.A.L.M. Microlaser Technologies AG Inc., Bernried, Germany) was used for LCM. The slides were removed from the freezer and dehydrated in 100% ethanol for 3 min and air dried before LCM. The LCM was performed according to the manufacturer's instruction. Individual fibre initial cells (total approx. 400 cells) or epidermal cells (total approx. 100 cells) were catapulted without precutting into 45 µl RNALater then stored at −20° C.

RNA was isolated from the captured cells as follows. RNA was extracted from the captured cells using the method described by Wu et al. (2002) with some modifications. The sample of the captured cells (with 45 µl RNALater) were homogenized in 500 µl RNA extraction buffer with 20 ng carrier RNA (carrier RNA from Qiagen RNeasy micro kit) using a Ystral homogenizer (HD Scientific). After spinning for 2 min at maximum speed in an Eppendorf micro centrifuge, the supernatant was transferred to a fresh tube. 250 µl ethanol was added to the sample before the sample was loaded onto a Qiagen RNeasy mini column. The column washing and RNA elution was as described in Qiagen RNeasy mini kit protocol. The eluted RNA was concentrated under vacuum until remaining volume was about 10 µl.

The isolated RNA was amplified using a MessageAmp aRNA Kit (Ambion) following manufacturer's instructions. Two rounds of amplifications were performed and the resulting anti-sense RNA was quantified at $OD_{260}$ and resuspended at concentration of 100 ng/µl. The RT-PCR of Myb25 and GhHD1 using the amplified RNA was essentially as described earlier except that 100 ng of amplified RNA (instead of 0.5 µg total RNA) per reaction was used as template. In addition to the β-tubulin positive control, a cotton polyubiquitin (CK738219 in Dowd et al. 2004) was used as a normalisation standard. The forward and reverse primers used for polyubiquitin RT-PCR were: 5'-CAAGACAAG-GAAGGCATCCCAC-3' (SEQ ID NO: 73) and 5'-TCG-GAACTCTCCACCTCCAAAG-3' (SEQ ID NO: 74) respectively and these resulted in a cDNA fragment of 200 bp. All RT-PCR reactions were amplified using the previously described RT-PCR program with 28 cycles and the resulting RT-PCR bands were quantified using Multi Gange V 2.11 (FUJIFILM) and then normalised using the corresponding polyubiquitin bands.

Both GhHD1 and GhMyb25 exhibited fibre initial enriched expression with the expression of GhHD1 being more than two fold enhanced in fibre initial cells relative to non-fibre epidermal cells, and GhMyb25 expression enhanced by 1.8 fold in fibre initial cells relative to in non-fibre epidermal cells.

Laser capture microdissection thus provided a very specific means of isolating the fibre initial cells from the adjacent non-fibre initial cells in the outer epidermis. Combining LCM with RT-PCR techniques, we have shown that both the GhMyb25 and the homeodomain gene were up-regulated on the day of anthesis in fibre initials relative to adjacent non-fibre ovule epidermal cells and expression was predominantly ovule-specific. Their spatial and temporal expression pattern therefore coincided with the time and location of fibre initiation and is further evidence of a role in this process.

Example 12

Heterologous Function of Genes in Other Plant Species

To show that these genes can have function in plants other than cotton, an over-expression construct with the subterranean clover stunt virus promoter 7 (Schünmann et al. 2003) driving the expression of the full length GhMyb25 cDNA clone was introduced into tobacco and *Arabidopsis* by *Agrobacterium* mediated transformation as follows. The coding region of Myb25 cDNA 0.9 Kb fragment was cloned into the EcoRI site of binary vector pPLEX3003 (GenBank AY159024) expressed from the subterranean clover stunt virus promoter 7 and linked to NADP malic enzyme terminator MeI (Schünmann et al., 2003). The pPLEX3003-GhMyb25 construct was then introduced into *Agrobacterium tumefaciens* AGL1 strain and used to transform (*Nicotiana tabacum* L. cv. 38) leaf as described by Horsch et al. (1985).

For RT-PCR verification of GhMyb25 expression in $T_0$ and $T_1$ generations of transgenic tobacco, total RNA was isolated from young leaves of the transgenic tobacco lines using the Trizol method (GibcoBRL) and DNase treated. 2 μg of RNA was used in each RT-PCR reaction using Qiagen one-step RT-PCR Kit and following the manufacture's protocol. The primers were the same as in the RT-PCR from cotton RNA resulting in a 224 bp cDNA fragment. A total number of 32 cycles at 94° C. for 1 min, 50° C. for 1 min and 72° C. for 1 min was used for the amplification and 5 μl of the reaction was loaded on a 2% agarose gel to visualise the RT-PCR band.

Genomic DNA was isolated from leaves of transgenic tobacco $T_1$ plants using half strength CTAB buffer and a simplified procedure of Patterson et al (1992). PCR reactions using genomic DNA of tobacco plants were performed to verify transgene (GhMyb25) segregation in T1 population. The PCR reaction contained 2 mM $MgCl_2$, 0.2 mM each of the dNTPs, 0.2 μM each of the same Myb25 forward and reverse primers as for RT-PCR, 1 unit Taq F2 DNA polymerase and 1×F2 buffer (Fisher Biotech Limited, Perth) in a 50 μl reaction. Twenty plants from each line were analysed and the presence of the transgene resulted a 224 bp fragment.

Phenotypic analysis of 4 independent primary transformants of tobacco expressing GhMyb 25 showed increased numbers of branched long-stalked trichomes not normally formed on the adaxial leaf surface. Branched long-stalked trichomes were occasionally observed on leaf veins of wild type tobacco, but on the transformants, a 3 to 12 fold increase in these trichomes was observed primarily on parts of the leaf other than on veins. In transgenic *Arabidopsis*, the expression of GhMyb25 had no obvious effect on trichomes.

$T_1$ plants (minimum 20 plants/line) of 6 transgenic tobacco lines were screened for transgene segregation at both genomic and mRNA level. A correlation between the increased number of branched long-stalked trichomes and transgene expression was observed visually in all the 6 lines. Line 11, for example, showed a 3:1 transgene segregation ratio and 5 plants from this line were used for detailed trichome number analysis. The number of long-stalked trichomes, short trichomes, stomata and epidermal pavement cells were counted on SEM images. The number of the long-stalked trichomes, short-stalked trichome and stomata per thousand epidermal cells from the four plants expressing the transgene (11-7, 11-4, 11-19 and 11-3) were compared to that of a null segregant plant, 11-8, that showed no expression of the transgene by RT-PCR. Amongst the three cell types, only the density of long-stalked trichomes showed a small (about 20%, averaged over the 4 plants), but significant increase over that of plant 11-8. The other two cell types had variable densities with some plants showing slightly higher and other plants slightly lower numbers when compared to 11-8. The most visible phenotype however was the branching of the long-stalked trichomes observed on the TO plants that were on average 8 times more prevalent in the transgenic T1 lines than in the null segregant controls.

GhMyb25 (and the GhMyb25-like gene) showed higher sequence similarity to the *Petunia hybrida* PhMyb1 and the *Antirrhinum* MIXTA factors than to GL1 or other cotton Mybs. Both PhMyb1 and MIXTA show petal epidermis-specific expression (Solano et al. 1995, Noda et al 1994) and MIXTA is a regulator of the conical shape of the petal epidermal cells (Noda et al 1994). Over-expression of MIXTA in transgenic tobacco caused the production of supernumerary trichomes on cotyledons, leaves, stems and floral organs as well as the production of novel conical cells on leaves (Glover et al. 1998, Payne et al. 1999). GhMyb25 on the other hand only caused an increase of branched long-stalked trichomes and a small increase in the total number of long-stalked trichomes in tobacco, but did not have any effect on short trichomes or epidermal cell shape. GhMyb25 was expressed only in the ovules, predominantly in fibre initials and not in later stage fibres, or petals, so is not a direct homolog of MIXTA.

Example 13

Production of Transgenic Cotton

For over-expression of genes in a fibre producing plant such as cotton, the coding sequence of a gene of the invention may be operably linked to a promoter and a 3' transcription termination and polyadenylation signal functional in plants, to form a chimeric gene. The promoter may be expressed constitutively throughout the plant, for example, a subterranean clover stunt virus promoter (S7; WO 96/06932), or in a tissue-specific manner. For example, the promoter may be preferentially active in the epidermal cells of the ovule, to provide an altered expression pattern of the coding sequence in these cells. The chimeric gene is operably linked to a selectable marker gene and introduced into a T-DNA vector. Cotton plants are transformed using the *Agrobacterium* mediated transformation technique. Transgenic cotton lines are identified, fibre number, fibre length, fuzz fibre length, cellulose content, and dry weight of the lint is analyzed.

For down-regulation of expression of one or more of the genes, hairpin-RNA (RNAi) constructs were generated for six genes: GhMyb25, GhHD1, GhMyb25-like, GhEX1, GhFU1 and GhFaE1 using the vector pHELLSGATE8 and recombinational cloning technology (Gateway™, Invitrogen). pHELLSGATE8 was based on pHELLSGATE described in Wesley et al (2001) (Genbank Accession no. AJ311874). pHELLSGATE8 was an improved vector which contained attR recombinational sites instead of attP sites and gave more efficient gene silencing compared to pHELLSGATE. pHELLSGATE8 did not contain a selectable marker in the intron; this did not affect the efficiency of obtaining the correct recombinant. For production of constructs in pHELLSGATE8, each gene insert is first introduced into the attP containing vector pDONR201 (Invitrogen) after PCR amplification of the gene insert using PCR primers containing attP sequences, so that the attP sites flanked the gene insert. The gene sequences used in the constructs are presented in Table 8.

TABLE 8

Gene sequences used in the constructs for RNAi.

| Candidate gene | Vector | Construct type | Sequence 5' (start) | Sequence 3' (end) | Sequence Length |
|---|---|---|---|---|---|
| GhMyb25 | pHELLSGATE8 | Hairpin | 581 | 804 | 224 bp |
| GhHD1 | pHELLSGATE8 | Hairpin | 1785 | 2119 | 335 bp |
| GhMyb25-like | pHELLSGATE8 | Hairpin | 272 | 832 | 561 bp |
| GhEX1 | pHELLSGATE8 | Hairpin | 344 | 779 | 436 bp |
| GhFU1 | pHELLSGATE8 | Hairpin | 52 | 530 | 479 bp |
| GhFaE1 | pHELLSGATE8 | Hairpin | 163 | 686 | 524 bp |

BP and LR Clonase enzymes (Invitrogen) were used according to the suppliers instructions. Detailed descriptions and methods for using the Gateway™ cloning system were available from the supplier (www.invitrogen.com). When the ccdB gene was present in a vector, it was propagated in the *E. coli* strain DB3.1 (Invitrogen).

Recombinants were selected on plates containing 50 µg/ml spectinomycin and grown in the same medium.

Recombination to introduce two copies of the gene inserts, one in sense orientation and the second in antisense orientation, into pHELLSGATE8 was carried out as follows. Each reaction mix contained 2 µl LR clonase buffer, 1-2 µl PCR product, 2 µl pHellsgate8 (150 ng/ml), Tris-EDTA to 8 µl, and 2 µl LR clonase. Each reaction was incubated at 25° C. for at least 1 hour, usually overnight, then 1 µl proteinase K added followed by incubation at 37° C. for 10 min. 1-10 µl of each reaction was transformed into DH5α cells, either RbCl- or electro-competent cells. Each mixture was plated on spectinomycin containing medium. Colonies were picked and small-scale plasmid preparations made for analysis with XbaI and XhoI restriction emzymes. In some cases the intron in pHELLSGATE8 became reversed during the recombination reaction, so it was necessary to screen a sufficient number of colonies to obtain a recombinant with the correctly oriented intron.

Each of the hairpin-RNA constructs was introduced into cotton using *Agrobacterium* mediated transformation. The cotton transformation method used was as described by Cousins et al (1991), as modified by Murray et al (1999).

Regenerated plants are analysed for the presence of the hairpin-RNA gene, its expression, and for altered fibre production.

Example 14

Discussion

The use of multiple mutant lines in the above mentioned expression studies enabled confirmation and complementation of the findings from one mutant to another and focus in on the most critical genes for fibre development. It also helps to smooth out "noise" contributed by the biological variability in fibre growth and the unknown and maybe diverse genetic backgrounds of some of the mutants. The comparison of gene expression profiles between the outer integument and the inner ovule tissues served as a filter, to eliminate those genes that are not expressed at higher levels in the outer integument and helped to focus on a small set of about 10 candidate genes. The wild type time course data reveal that the expression profiles of these candidate genes separated them into two classes with class I genes (GhMyb25, GhHD1 and GhCycD3; 1) showing peak expression at 0 dpa, coinciding with the time of fibre initiation; class II genes exhibiting increased expression at 2 dpa, suggesting a more important role in fibre elongation.

By analogy with the regulatory genes involved in *Arabidopsis* leaf trichome development, it might have been expected to find a Myb transcription factor expressed in cotton fibre that was similar to GL1. GhMyb25 (and the GhMyb25-like gene), however, shows higher sequence similarity to the *Petunia hybrida* Myb.Ph3 and the *Antirrhinum* MIXTA than to GL1 or other cotton Mybs. Both Myb.Ph3 and MIXTA show petal epidermis-specific expression. Based on its expression pattern, it was speculated that the function of Myb.Ph3 was to regulate flavonoid biosynthesis (Solano et al., 1995), but this speculation has not been confirmed. The function of MIXTA has been revealed as a controlling factor for the conical shape of petal epidermal cells (Noda et al., 1994). Over-expression of MIXTA in transgenic tobacco lead to production of supernumerary trichomes on cotyledons, leaves and stems as well as novel production of conical cells on leaves (Payne et al., 1999). In contrast, GhMyb25 is expressed only in the ovules and not in later stage fibres (or petals so is not a homolog of MIXTA). It had higher expression in outer integuments and the time of expression coincide with fibre initiation. Accordingly, GhMyb25 plays a role in fibre initiation. The fact that GhMyb25 is down-regulated in all the lintless mutants, including the new fl mutant, points to a role as a positive regulator of fibre initiation.

Comparison of the fl mutant with its parental genotype identified in addition to the 8 genes common to other mutants, a second Myb transcription factor, a GhMyb25-like gene, containing a conserved region outside the R2R3 domain shared by all the MIXTA class of Mybs (Stracke et al., 2001). The GhMyb25-like gene is only 64% identical to probable A-genome derived GhMyb25 at the nucleotide level (69% similarity at the amino acid level), suggesting it is unlikely to be the homoelogous D-genome partner of GhMyb25 present in tetraploid cotton. GhMyb25-like is expressed at low level in −4, −2 dpa ovules of DP16 (0.3 relative to 0 dpa ovule of 1) and increased sharply to 1 at 0 dpa and remained at a similar level of 1 at 2 dpa. This expression profile indicates a role for GhMyb25-like in fibre initiation. Among the 5 additional genes identified in this analysis, there were two RD22 genes, consistent with the findings of Li et al., (2002) who identified a RD22 gene showing fibre specific expression using the same lines.

The putative homeodomain gene identified in this study has high similarity in part of its C-terminus to the L1 specific and ovule specific homeodomain gene ATML1. ATML1 was classified in the same HD-GL2 class as *Arabidopsis* GL2 based on sequence homology and they share a common L1 layer-specific or dermal-specific pattern of expression (Lu et al., 1996). ATML1 was proposed to be involved in setting up morphogenetic boundaries of positional information necessary for controlling cell specification and pattern formation based on gene expression patterns. GL2 that has been studied for its role in trichome, root-hair and seed coat development (Rerie et al., 1994, Cristina et al., 1996, Masucci et al., 1996). The GL2 mutations resulted in aborted trichomes with aberrant cell expansion whereas entopic expression noticeably increased the number of trichomes and induced clusters of trichome formation (Ohashi et al., 2002). The GhHD1 gene is expressed in ovules with higher expression in outer integument, in fibres as well as in leaves and this expression pattern probably reflects a more general role in different epidermal cell specification and pattern formation similar to that shown by the GL2.

DNA endoreduplication, a strategy to amplify nuclear DNA without cell division is a major mechanism leading to somatic polyploidisation in plants (reviewed by Joubes and Chevalier 2000). Correlations have been established between polyploidy and cell differentiation and cell expansion. While it is well established that *Arabidopsis* trichomes undergo four rounds of endoreduplication during development, leading to branched cells with nuclei containing about 32C DNA (Schnittger et al., 2002), it has been less than clear whether cotton fibre initials undergo a similar process. Berlin (1986) studied tritiated thymidine uptake by epidermal layer using in vitro cultured cotton ovules and observed that there was an increase in thymidine incorporation from −2 dpa to 1 dpa and then the incorporation declined and finally stopped at 6 dpa. These observations were interpreted as DNA synthesis in preparation for cell division. Since fibre initials do not undergo divisions and no thymidine incorporation was observed in the elongating fibres, the author suggested that gene amplification did not occur during fibre development over the time observed (Berlin 1986). Van't Hof (1998) reported that the DNA content of developing cotton fibre cells only increased by about 24% from 2 dpa to 5 dpa and suggested that during early stages of development fibre cell nuclei either selectively amplify certain sequences or enter S-phase replicating only a portion of their genome. Using laser-confocal microscopy and propidium iodide staining, we examined ovule epidermal cell division rates and DNA contents of epidermal cells and fibre cells. Our results show that the epidermal cell division rates remain relatively constant from −2 dpa to 0 dpa (with a small increase at −1 dpa). While nuclear DNA contents of epidermal cells remain largely unchanged from −2 dpa to 0 dpa, the fibre initials contain nuclei that mostly show higher than 2C DNA content with the majority of cells showing DNA contents between 2.8 C and 5.2 C. While our results suggest the fibre initials undergo one round DNA endoreduplication starting at 0 dpa, they do not exclude the possibility of selective amplification of certain sequences or partial replication of the genome at later stages suggested by Van't Hof's work. In addition, the enlarged nuclei in fibre initials revealed by the ultrastructural studies (review by Berlin 1986) provided further support to the DNA amplification phenomenon.

Although accumulating data reveal that DNA endoreduplication is developmentally regulated, it is still poorly understood in plants (reviewed by Joubes and Chevalier 2000). Assuming the endoreduplication is a modified cell cycle, it may share common determinants with the classic cell cycle (Joubes and Chevalier 2000). The two main control points in the cell cycle are at the G1/S and G2/M transitions and in most plant cell types, the primary control point probably operates during G1 phase. This period not only includes the point of commitment to cell division, but may also represent the time during which differentiation decisions are made (reviewed by Meijer and Murray 2000). Mammalian cyclin D-Cdk4 complexes have been characterized as growth factor-responsive cell cycle regulators operating during G1 phase. Cyclin D3 was found to be present at high levels in megakaryocytes undergoing endoreduplication and was upregulated following exposure to the proliferation, maturation and ploidy-promoting factor, Mpl ligand (Zimmet et al., 1997). In plants, the presence of mutiple Cyclin D3 genes raises the question of functional redundancy of these genes and the extent to which they may have distinct or overlapping roles (Meijer and Murray, 2000). *Arabidopsis* CycD3; 1, which is highly cytokinin-inducible (Riou-Khamlichi et al. 1999), when ectopically expressed, induced not only DNA replication but also cell division in trichomes (Schnittger et al., 2002). In synchronized tobacco BY-2 cell suspension cultures, tobacco CycD3; 2 was induced in G1 and remained at a constant level throughout the cell cycle, similar to mammalian D-type cyclins. In contrast, CycD3;1 transcripts accumulated during mitosis, a pattern of expression not normally associated with D-type cyclins, suggesting a novel role for plant cyclins during mitosis or alternatively a BY-2 cell-specific phenomenon and not a normal feature of plant cell-cycle progression (Sorrell et al., 1999). The GhCycD3.1 identified in our experiments shows highest sequence homology to *Euphobia esula* cyclin D3;2. Since the decreased expression of this gene in the outer integuments of lintless mutant 4A-183 did not affect the epidermal cell division rates, it is appears that this gene is involved in the DNA endoreduplication of fibre initials similar to the tomato CycD3;1's involvement in endoreduplication of the differentiated giant cells of the fruit gel tissue (Joubes et al., 2000).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Ali, S., Holloway, B. and Taylor, W. C. (2000) *Plant. Mol. Biol. Rep.* 18:123-132.
Beasley, C. A. and Ting, I. P. (1973) *Am. J. Bot.* 60:130-139.
Berlin, J. D. (1986) *Cotton Physiology*, Memphis, Tenn., pp 375-414.

Bonaldo M. F., Lenno, G. and Soares, M. B. (1996) *Genome Res.* 6:791-806.

Bourque, J. E. (1995) *Plant Sci.* 105:125-149.

Cousins, Y. L., Lyon, B. R. and Llewellyn, D. J. (1991) *Australian Journal of Plant Physiology* 18:481-494.

Craig, S. and Beaton, C. D. (1996) *J. Microsc.* 182:102-105.

Cristina, M. D., Sessa, G., Dolan, L., Linstead, P., Baima, S., Ruberti, I. and Morelli, G. (1996) *Plant J.* 10:393-402.

Dowd, C., Wilson, I., and McFadden, H. (2004) *Mol. Plant. Microbe Interact.,* 17:654-667.

Haseloff, J. and Gerlach, W. L. (1988) *Nature* 334:585-591.

Hasenfratz, M. P., Tsou, C. L. and Wilkins, T. A. (1995) *Plant Physiol.* 108:1395-1404.

Horsch, R. B., Fry, J. E., Hoffmann, N. L., Eichoholtz, D., Rogers, S. G. and Fraley, R. T. (1985) *Science,* 227:1229-1231.

Hütlskamp, M., Misera, S. and Jürgens, G. (1994) *Cell* 76:555-566.

Glover, B. J., Perez-Rodriguez, M., and Martin, C. (1998) *Development* 125:3497-3508.

Ji, S. J., Lu, Y. C., Feng J. X., Wei, G., Li, J., Shi, Y. H., Fu, Q., Liu, D., Luo, J. C. and Zhu, Y. X. (2003) *Nucleic Acids Res.* 31:2534-2543.

Joubès, J. and Chevalier, C. (2000) *Plant Mol. Biol.* 43:735-745.

Joubès, J., Walsh, D., Raymond, P. and Chevalier, C. (2000) *Planta* 211:430-439.

Lemieux, B. (2000) *Current Genomics.* 1: 301-311.

Li, C. H., Zhu, Y. Q., Meng, Y. L., Wang, J. W., Xu, K. X., Zhang, T. Z. and Chen X. Y. (2002) *Plant Sci.* 163:1113-1120.

Li, X. B., Cai, L., Cheng, N. H. and Liu, J. W. (2002) *Plant Physiol.* 130:666-674.

Loguercio, L. L., Zhang J. Q. and Wilkins, T. A. (1999) *Mol. Gen. Genet.* 261:660-670.

Lu, P., Porat, R., Nadeau, J. A. and O'Neill, S. D. (1996) *Plant Cell* 8:2155-2168.

Masucci, J. D., Rerie, W. G., Foreman, D. R., Zhang, M. and Galway, M. E. (1996) *Development* 122:1253-1260.

McFadden, H. G., Chapple, R., De Feyter, R. and Dennis, E. (2001) *Mol. Plant. Pathol.* 58:119-131.

Meijer, M. and Murray, J. A. H. (2000) *Plant Mol. Biol.* 43:621-633.

Murray, F., Llewellyn, D., McFadden, H., Last, D., Dennis, E. S., and Peacock, W. J. (1999) *Molecular Breeding* 53:219-232.

Nakazono, M., Qiu, F., Borsuk, L. A., and Schnable, P. S. (2003) *Plant Cell,* 15:583-596.

Needleman, S. B. and Wunsch, C. D. (1970) *J. Mol. Biol.* 48:443-453.

Noda, K. I., Glover, B. J., Linstead, P. and Martin, C. (1994) *Nature* 369:661-664.

Ohashi, Y., Oka, A., Ruberti, I., Morelli, G. and Aoyama, T. (2002) *Plant J.* 29:359-369.

Oppenheimer, D. G., Herman, P. L., Sivakumaran, S., Esch, J. and Marks, M. D. (1991) *Cell* 67:483-493.

Patterson, A. H., Brubaker C. L., and Wendel J. F. (1993) *Plant Mol. Biol. Reptr.,* 11:122-127.

Payne, T., Clement, J., Arnold, D. and Lloyd, A. (1999) *Development* 126:561-682.

Perriman, R., Delves, A. and Gerlach, W. L. (1992) *Gene* 113:157-163.

Rerie, W. G., Feldmann, K. A. and Marks, M. D. (1994) *Genes & Development* 8:1388-1399.

Riou-Khamlichi, C., Huntley, R., Jacqmard, A. and Murray, J. A. H. (1999) *Science* 283:1541-1544.

Schellmann, S., Schnittger, A., Kirik, V., Wada, T., Okada, K., Beermann, A., Thumfahrt, J., Jürgens, G. and Hülskamp, M. (2002) *EMBO J.* 21:5036-5046.

Schenk, P. M., Kazan, K., Wilson, I., Anderson, J. P., Richmond, T., Somerville, S. C. and Manners, J. M. (2000) *Proc. Natl. Acad. Sci. USA* 97:11655-11660.

Schnittger, A., Schöbinger, U., Bouyer, D., Weinl, C., Stierhof, Y-D. and Hülskamp, M. (2002) *Proc. Natl. Acad. Sci. USA* 99:6410-6415.

Senior, I. J. (1998) *Biotech. Genet. Engin. Revs.* 15:79-119,

Shippy, R., Lockner, R., Farnsworth, M. and Hampel, A. (1999) *Mol. Biotech.* 12:117-129.

Schünmann, P. H. D., Llewellyn, D. J., Surin, B., Boevink, P., De Feyter, R. C. and Waterhouse, P. M. (2003) *Functional Plant Biol,* 30: 443-452.

Smith, N. A., Singh, S. P., Wang, M. B., Stoutjesdijk, P. A., Green, A. G. and Waterhouse, P. M. (2000) 407:319-320.

Solano, R., Nieto, C., Avila, J., Canas, L., Diaz, I. and Paz-Ares, J. (1995) *EMBO J.* 14:1773-1784.

Sorrell, D. A., Combettes, B., Chaubet-Gigot, N., Gigot, C. and Murray, J. A. M. (1999) *Plant Physiol.* 119:343-351.

Stracke, R., Werber, M. and Weisshaar, B. (2001) *Curr. Opin. Plant Biol.* 4:447-456.

Szymanski, D. B. and Marks, M. D. (1998) *Plant Cell* 10:2047-2062.

Szymanski, D. B., Lloyd, A. M. and Marks, M. D. (2000) *Trends in Plant Science* 5:214-219.

Turley, R. B. and Ferguson, D. L. (1996) *J. Plant Physiol.* 149:695-702.

Van't Hof, J. (1998) *Am. J. Bot.* 86:776-779.

Walker, A. R., Davison, P. A., Bolognesi-Winfield, A. C., James, C. M., Srinivasan, N., Blundell, T. L., Esch, J. J., Marks, M. D. and Gray, J. C. (1999) *Plant Cell* 11:1337-1350.

Waterhouse, P. M., Graham, M. W., and Wang, M.-B. (1998) *Proc. Natl. Acad. Sci.* 95:13959-13964.

Wesley, S. V., Helliwell, C. A., Smith, N. A., Wang, M. B., Rouse, D. T., Liu, Q., Gooding, P. S., Singh, S. P., Abboft, D., Stoutjesdijk, P. A., Robinson, S. P., Gleave, A. P., Green, A. G., and Waterhouse, P. M. (2001) *Plant Journal* 27:581-590.

Wilson, D. L., Buckley, M. J., Helliwell, C. A. and Wilson I. W. (2003) *Bioinformatics* 19:1325-1332.

Wu, Y., Llewellyn, D. J. and Dennis, E. S. (2002) *Plant Mol. Biol. Rep.* 20:213-218.

Yu, X. H., Zhu, Y. Q., Lu, S., Zhang T. Z., Chen X. Y. and Xu, Z. H. (2000) *Science in China* (Series C) 43:623-630.

Zimmet, J. M., Ladd, D., Jackson, C. W., Stenberg, P. E. and Ravid, K. (1997) *Mol. Cell. Biol.* 17:7248-7259.

The invention claimed is:

1. A method of increasing fibre initiation and/or elongation in a fibre producing plant comprising introducing into the plant a nucleotide sequence encoding a polypeptide comprising consecutive amino acids whose sequence is identical to the amino acid sequence encoded by the nucleotide sequence set forth in SEQ ID NO: 38, such that the production of the polypeptide is increased when compared to a wild-type fiber producing plant, wherein the nucleotide sequence had been previously isolated.

2. A method of reducing fibre initiation and/or elongation in a fibre producing plant comprising introducing into the plant an antisense polynucleotide or a polynucleotide that produces a dsRNA molecule such that the production of a polypeptide comprising consecutive amino acids whose sequence is identical to the amino acid sequence encoded by the nucleotide sequence set forth in SEQ ID NO: 38 is reduced when compared to a wild-type fiber producing plant, wherein the polynucleotide sequence that produces the dsRNA had been previously isolated.

3. The method of claim 1 or 2, wherein the polypeptide comprises consecutive amino acids whose sequence is set forth in SEQ ID NO: 12.

4. The method of claim 2, wherein the dsRNA molecule is double-stranded over at least 19 basepairs whose sequence corresponds to a consecutive sequence set forth in SEQ ID NO: 38, or to a consecutive sequence which is identical to the sequence set forth in SEQ ID NO: 38.

5. The method of claim 1 or 2, wherein the plant is a species of the Genus *Gossypium*.

6. A substantially purified and/or recombinant polypeptide comprising consecutive amino acids whose sequence is set forth in SEQ ID NO: 12.

7. An isolated and/or exogenous polynucleotide comprising a polynucleotide selected from the group consisting of:
   i) a polynucleotide comprising consecutive nucleotides whose nucleotide sequence is set forth in SEQ ID NO: 38; and
   ii) a polynucleotide which encodes a polypeptide comprising consecutive amino acids whose sequence is identical to the amino acid sequence encoded by the nucleotide sequence set forth in SEQ ID NO: 38.

8. A vector comprising the polynucleotide of claim 7.

9. A plant or bacterial cell comprising the vector of claim 8.

10. A transgenic plant which comprises the exogenous polynucleotide of claim 7.

11. The transgenic plant of claim 10, which when compared to an isogenic non-transgenic plant, produces an increased level of a polypeptide comprising consecutive amino acids whose sequence is identical to the amino acid sequence encoded by the nucleotide sequence set forth in SEQ ID NO: 38.

12. The transgenic plant of claim 11, wherein the polypeptide comprises consecutive amino acids whose amino acid sequence is set forth in SEQ ID NO:12.

13. A transgenic seed of the plant of claim 10 comprising said polynucleotide.

14. A process for producing fibre comprising obtaining the transgenic plant of claim 10 so as to thereby produce the fibre.

* * * * *

SEQUENCE LISTING

<160> NUMBER OF SEQ ID NOS: 74

<210> SEQ ID NO 1
<211> LENGTH: 624

```
<212> TYPE: PRT
<213> ORGANISM: Gossypium hirsutum

<400> SEQUENCE: 1

Val Lys Phe Trp Phe Gln Asn Lys Arg Thr Gln Met Lys Ala Gln His
1               5                   10                  15

Glu Arg His Glu Asn Ala Ile Leu Lys Ala Glu Asn Glu Lys Leu Arg
            20                  25                  30

Ala Glu Asn Asn Arg Tyr Lys Glu Ala Leu Ser Asn Ala Thr Cys Pro
        35                  40                  45

Ser Cys Gly Gly Pro Ala Ala Leu Gly Glu Met Ser Phe Asp Glu Gln
    50                  55                  60

His Leu Arg Ile Glu Asn Ala Arg Leu Arg Glu Ile Asp Arg Ile
65                  70                  75                  80

Ser Gly Ile Ala Ala Lys Tyr Val Gly Lys Pro Leu Ser Ser Leu Pro
                85                  90                  95

His Leu Ser Ser His Leu His Ser Arg Ser Ala Asp Leu Gly Ala Ser
            100                 105                 110

Asn Phe Gly Asn Gln Ser Gly Phe Val Gly Glu Met Asp Arg Ser Gly
        115                 120                 125

Asp Leu Leu Arg Ser Val Ser Gly Pro Thr Glu Ala Asp Lys Pro Met
    130                 135                 140

Ile Val Glu Leu Ala Val Ala Ala Met Glu Glu Leu Ile Arg Met Ala
145                 150                 155                 160

Gln Ser Gly Glu Pro Leu Trp Val Pro Gly Asp Asn Ser Thr Asp Val
                165                 170                 175

Leu Asn Glu Asp Glu Tyr Leu Arg Thr Phe Pro Arg Gly Ile Gly Pro
            180                 185                 190

Lys Pro Leu Gly Leu Arg Ser Glu Ala Ser Arg Glu Ser Ala Val Val
        195                 200                 205

Ile Met Asn His Val Asn Leu Val Glu Ile Leu Met Asp Val Asn Gln
    210                 215                 220

Trp Ser Ser Val Phe Cys Gly Ile Val Ser Arg Ala Met Thr Leu Glu
225                 230                 235                 240

Val Leu Ser Thr Gly Val Ala Gly Asn Tyr Asn Gly Ala Leu Gln Val
                245                 250                 255

Met Thr Ala Glu Phe Gln Val Pro Ser Pro Leu Val Pro Thr Arg Glu
            260                 265                 270

Asn Tyr Phe Ala Arg Tyr Cys Lys Gln His Ile Asp Gly Thr Trp Ala
        275                 280                 285

Val Val Asp Val Ser Leu Asp Asn Leu Arg Pro Asn Pro Met Ser Ser
    290                 295                 300

Val Glu Arg Pro Ser Gly Cys Leu Ile Gln Asn Cys Gln Met Asp Thr
305                 310                 315                 320

Ser Lys Val Ile Trp Val Glu His Val Glu Val Asp Asp Arg Ala Val
                325                 330                 335

His Asn Ile Tyr Arg Pro Val Val Asn Ser Gly Leu Ala Phe Gly Ala
            340                 345                 350

Lys Arg Trp Val Ala Thr Leu Asp Arg Gln Cys Glu Arg Leu Ala Ser
        355                 360                 365

Ser Met Ala Ser Asn Ile Pro Ala Gly Gly Leu Cys Val Ile Thr Ser
    370                 375                 380

Pro Glu Gly Arg Lys Ser Met Leu Lys Leu Ala Glu Arg Met Val Thr
385                 390                 395                 400
```

```
Ser Phe Cys Thr Gly Val Gly Ala Ser Thr Ala His Ala Trp Thr Thr
                405                 410                 415

Leu Ser Ala Thr Gly Ser Asp Asp Val Arg Val Met Thr Arg Lys Ser
            420                 425                 430

Met Asp Asp Pro Gly Arg Pro Pro Gly Ile Val Leu Ser Ala Ala Thr
        435                 440                 445

Ser Phe Trp Ile Gln Val Pro Pro Lys Arg Val Phe Asp Phe Leu Arg
    450                 455                 460

Asp Glu Asn Ser Arg Ser Glu Trp Asp Ile Leu Ser Asn Gly Gly Leu
465                 470                 475                 480

Val Gln Glu Met Ala His Ile Ala Asn Gly Arg Asp Pro Gly Asn Cys
                485                 490                 495

Val Ser Leu Leu Arg Val Asn Ser Ala Asn Ser Ser Gln Ser Asn Met
            500                 505                 510

Leu Ile Leu Gln Glu Ser Cys Thr Asp Ala Lys Gly Ser Tyr Val Ile
        515                 520                 525

Tyr Ala Pro Val Asn Ile Val Ala Met Asn Ile Val Leu Ser Gly Gly
    530                 535                 540

Asp Pro Asp Tyr Val Ala Leu Leu Pro Ser Gly Phe Ala Ile Leu Pro
545                 550                 555                 560

Asp Gly Pro Gly Val Asn Gly Gly Ile Leu Glu Ile Gly Ser Gly
                565                 570                 575

Gly Ser Leu Leu Thr Val Ala Phe Gln Ile Leu Val Asp Ser Val Pro
            580                 585                 590

Thr Ala Lys Leu Ser Leu Gly Ser Val Ala Thr Val Asn Ser Leu Ile
        595                 600                 605

Lys Cys Thr Val Glu Arg Ile Lys Ala Ala Val Lys Cys Asn Asn Ala
    610                 615                 620

<210> SEQ ID NO 2
<211> LENGTH: 309
<212> TYPE: PRT
<213> ORGANISM: Gossypium hirsutum

<400> SEQUENCE: 2

Met Gly Arg Ser Pro Cys Cys Glu Lys Val Gly Leu Lys Lys Gly Pro
1               5                   10                  15

Trp Thr Pro Glu Glu Asp Gln Lys Leu Leu Ala Tyr Ile Glu Gln His
                20                  25                  30

Gly His Gly Ser Trp Arg Ala Leu Pro Ser Lys Ala Gly Leu Gln Arg
            35                  40                  45

Cys Gly Lys Ser Cys Arg Leu Arg Trp Ile Asn Tyr Leu Arg Pro Asp
    50                  55                  60

Ile Lys Arg Gly Lys Phe Ser Leu Gln Glu Glu Gln Thr Ile Ile Gln
65                  70                  75                  80

Leu His Ala Leu Leu Gly Asn Arg Trp Ser Ala Ile Ala Thr His Leu
                85                  90                  95

Pro Lys Arg Thr Asp Asn Glu Ile Lys Asn Tyr Trp Asn Thr His Leu
            100                 105                 110

Met Lys Arg Leu Thr Lys Met Gly Ile Asp Pro Val Thr His Lys Pro
        115                 120                 125

Lys Thr Asp Ala Leu Gly Ser Thr Thr Gly Asn Pro Lys Asp Ala Ala
    130                 135                 140

Asn Leu Ser His Met Ala Gln Trp Glu Ser Ala Arg Leu Glu Ala Glu
145                 150                 155                 160
```

```
Ala Arg Leu Val Arg Glu Ser Lys Leu Val Pro Ser Asn Pro Pro Gln
            165                 170                 175

Ser Asn His Phe Thr Ala Val Ala Pro Ser Pro Thr Pro Ala Thr Arg
        180                 185                 190

Pro Gln Cys Leu Asp Val Leu Lys Ala Trp Gln Gly Val Val Cys Gly
    195                 200                 205

Leu Phe Thr Phe Asn Met Asp Asn Asn Leu Gln Ser Pro Thr Ser
210                 215                 220

Thr Leu Asn Phe Met Glu Asn Thr Thr Leu Pro Met Ser Ser Ser
225                 230                 235                 240

Ser Ser Val Asn Gly Met Phe Asn Glu Asn Phe Gly Trp Asn Ser Ser
                245                 250                 255

Ile Asn Pro Cys Glu Ser Gly Asp Asn Leu Lys Val Glu Tyr Gly Ser
            260                 265                 270

Asp Gln Ile Pro Glu Leu Lys Glu Arg Leu Asp His Pro Met Glu Leu
        275                 280                 285

His Glu Met Asp Tyr Ser Ser Glu Gly Thr Trp Phe Gln Glu Leu Phe
    290                 295                 300

Gly Phe Asn Gly Leu
305

<210> SEQ ID NO 3
<211> LENGTH: 150
<212> TYPE: PRT
<213> ORGANISM: Gossypium hirsutum

<400> SEQUENCE: 3

Arg Cys Glu Arg Leu Leu Leu Cys Val Ile Ser Asp Ala Arg Ser Ile
1               5                   10                  15

His Tyr Leu Pro Ser Val Leu Ala Thr Ala Thr Met Met His Val Ile
            20                  25                  30

Asp Gln Val Glu Leu Phe Asn Pro Ile Asp Tyr Gln Asn Gln Leu Leu
        35                  40                  45

Ser Val Leu Lys Ile Ser Lys Glu Lys Val Asn Asp Cys Tyr Lys Leu
    50                  55                  60

Ile Leu Asp Val Ser Thr Arg Pro Gln Ala Gln Gly Asn Gly Gly Ala
65                  70                  75                  80

Cys Lys Arg Lys Val Glu Glu Arg Val Pro Ser Ser Pro Ser Gly Val
                85                  90                  95

Ile Asp Ala Ala Phe Gly Ser Asp Ser Ser Asp Ser Trp Gly Thr
            100                 105                 110

Val Ser Leu Ser Pro Glu Gln Gln Pro Pro Phe Lys Lys Ser Arg Ala
        115                 120                 125

Gln Glu Gln Val Met Arg Leu Pro Ser Leu Asn Arg Val Phe Val Asp
    130                 135                 140

Ile Val Gly Ser Pro Ser
145                 150

<210> SEQ ID NO 4
<211> LENGTH: 229
<212> TYPE: PRT
<213> ORGANISM: Gossypium hirsutum

<400> SEQUENCE: 4

Met Ala Asn His Thr Val Thr Phe Leu Pro Lys Leu Ser Ile Glu Ala
1               5                   10                  15

Ile Gln Thr Val Thr Pro Met Arg Ile Thr Glu Pro Arg Gln Thr Arg
```

```
                    20                  25                  30
Gln Val Leu Ala Gly Glu Leu Val Gly Pro Gly Ile Phe Gln Arg Cys
                35                  40                  45

Leu Asn Val Val Gln Tyr Tyr Met Lys Glu Lys Glu Glu Asp Ser Gly
             50                  55                  60

Trp Leu Leu Ala Gly Trp Ile Lys Glu Thr Leu Gly Arg Ala Leu His
 65                  70                  75                  80

Glu Gln Pro Met Ile Ser Gly Arg Leu Arg Lys Gly Glu Arg Asn Asp
                 85                  90                  95

Gly Glu Leu Glu Ile Val Ser Asn Asp Cys Gly Ile Arg Leu Ile Glu
            100                 105                 110

Ala Arg Ile Gln Met Asn Leu Ser Asp Phe Leu Asp Leu Lys Gln Arg
            115                 120                 125

Glu Asp Ala Glu Ala Gln Leu Val Phe Trp Lys Ile Asp Glu Gln
            130                 135                 140

Asn Pro Gln Phe Ser Pro Leu Phe Tyr Val Gln Val Thr Asn Phe Gln
145                 150                 155                 160

Cys Gly Gly Tyr Ser Ile Gly Ile Ser Cys Ser Ile Leu Leu Ala Asp
                165                 170                 175

Leu Leu Leu Met Lys Glu Phe Leu Lys Thr Trp Ala Asp Ile Pro Thr
            180                 185                 190

Arg Leu Leu Ser Thr Lys Thr Met Asn Lys Ser Phe Leu Tyr Ser Thr
                195                 200                 205

Phe Leu Ala Glu Lys His Gln Trp Cys Leu Pro Thr Ser Ser His Gln
            210                 215                 220

Ile Gln Ala Lys Leu
225

<210> SEQ ID NO 5
<211> LENGTH: 107
<212> TYPE: PRT
<213> ORGANISM: Gossypium hirsutum

<400> SEQUENCE: 5

Met Ala Lys Tyr Leu Asn Val Val Leu Val Leu Ala Leu Val Val Val
 1               5                  10                  15

Gln Ala Thr Ala Arg Asn Val Pro Ser Asp Ala Ala Gly Leu Asn Asp
                20                  25                  30

Gln Lys Asn Leu Leu Thr Tyr Gly Gly Ile Gly Gly Tyr Ser Gly Met
            35                  40                  45

Gly Ser Asn Gly Met Pro Met Gly Val Gly Ser Val Gly Gly Met
         50                  55                  60

Thr Gly Leu Gly Gly Thr Gly Gly Met Gly Ala Met Val Gly Val Gly
 65                  70                  75                  80

Tyr Gly Gly Gly Pro Gly Ala Gly Gly Asn Glu Gly Gly Val Gly
                 85                  90                  95

Ile Gly Asn Ala Pro Gly Val Val His Phe Pro
            100                 105

<210> SEQ ID NO 6
<211> LENGTH: 112
<212> TYPE: PRT
<213> ORGANISM: Gossypium hirsutum

<400> SEQUENCE: 6

Ser Ser Asp Ser Arg Lys Pro Leu Ala Ser Phe Tyr Leu Glu Lys Thr
 1               5                  10                  15
```

```
Lys Lys Leu Leu Leu Cys Trp Thr Cys Ser Cys Phe Ser Leu Tyr
            20                  25                  30

Gly Val Val Tyr Gly Leu Tyr Tyr Glu Phe Tyr Met Asn Arg Thr Leu
            35                  40                  45

Asn Leu Val Arg Lys Leu Arg Met Ser Leu Gly Gly Ala Glu Val Leu
 50                  55                  60

Met Ala Ile Ala Gly Leu Trp Ala Val Val Leu Arg Pro Leu Met Ile
 65                  70                  75                  80

Arg Tyr Ala Val Glu Met Ser Gln Met Ile Gly Ile Ser Val Arg Arg
                 85                  90                  95

Phe Phe Ser Asn Pro Leu Ser Pro Ser Val Ser Phe Phe Tyr Trp Tyr
                100                 105                 110

<210> SEQ ID NO 7
<211> LENGTH: 258
<212> TYPE: PRT
<213> ORGANISM: Gossypium hirsutum

<400> SEQUENCE: 7

Met Ala Thr Lys Thr Met Met Leu Gln Ile Phe Pro Leu Phe Phe Phe
 1               5                  10                  15

Leu Phe Ser Val Cys Asn Ser Ile Phe Leu Gly Ala Asn Gly Asp Asp
            20                  25                  30

Asn Gly Gly Trp Gln Thr Ala His Ala Thr Phe Tyr Gly Gly Ala Asp
            35                  40                  45

Ala Thr Gly Thr Met Gly Gly Ala Cys Gly Tyr Gly Asn Leu Tyr Ser
 50                  55                  60

Gln Gly Tyr Gly Thr Ser Thr Ala Ala Leu Ser Thr Ala Leu Phe Asn
 65                  70                  75                  80

Asn Gly Leu Ser Cys Gly Ala Cys Tyr Glu Leu Arg Cys Asn Asn Asp
                 85                  90                  95

Pro Gln Trp Cys Ile Ser Arg Thr Ile Thr Val Thr Ala Thr Asn Phe
                100                 105                 110

Cys Pro Pro Asn Tyr Ala Leu Ser Ser Asp Asn Gly Gly Trp Cys Asn
            115                 120                 125

Pro Pro Arg Glu His Phe Asp Leu Ala Glu Pro Arg Phe Leu Arg Ile
130                 135                 140

Ala Glu Tyr Arg Ala Gly Ile Val Pro Val Met Phe Arg Arg Val Ser
145                 150                 155                 160

Cys Val Lys Lys Gly Gly Ile Arg Tyr Thr Met Asn Gly His Ser Tyr
                165                 170                 175

Phe Asn Met Val Leu Ile Thr Lys Leu Gly Gly Ala Gly Asp Ile Thr
            180                 185                 190

Ser Val Ser Ile Lys Gly Ser Arg Thr Gly Trp Leu Pro Met Ser Arg
            195                 200                 205

Asn Trp Gly Gln Asn Trp Gln Ser Asn Ala Tyr Leu Asn Gly Gln Ser
210                 215                 220

Leu Ser Phe Lys Val Thr Ala Ser Asp Gly Arg Thr Ile Thr Ala Tyr
225                 230                 235                 240

Asn Val Val Pro Ala Gly Trp Gln Phe Gly Gln Thr Phe Glu Gly Gly
                245                 250                 255

Gln Phe

<210> SEQ ID NO 8
<211> LENGTH: 190
```

<212> TYPE: PRT
<213> ORGANISM: Gossypium hirsutum

<400> SEQUENCE: 8

```
Val Pro Phe Tyr Ser Ser Asn Tyr Leu Leu His Glu Ser Cys Met Met
1               5                   10                  15

Met Ile Ala Ser Leu Val Pro Asn Phe Met Met Gly Val Ile Ile Gly
            20                  25                  30

Ala Gly Tyr Ile Gly Leu Leu Met Met Thr Ala Gly Tyr Phe Arg Leu
        35                  40                  45

Leu Pro Asp Leu Pro Lys Ile Phe Trp Arg Tyr Pro Val Ser Tyr Ile
    50                  55                  60

Asn Tyr Gly Ala Trp Ala Leu Gln Gly Ala Tyr Lys Asn Asp Met Val
65                  70                  75                  80

Gly Leu Glu Phe Asp Gly Phe Ile Pro Gly Gly Pro Lys Leu Lys Gly
                85                  90                  95

Asp Val Val Leu Thr Ser Met Leu Gly Ile His Leu Asp His Ser Lys
            100                 105                 110

Trp Trp Asp Leu Ala Ala Val Ile Met Ile Leu Ile Ala Tyr Arg Leu
        115                 120                 125

Leu Phe Phe Ile Ile Leu Lys Phe Lys Glu Arg Val Ser Pro Leu Phe
    130                 135                 140

Arg Thr Leu Tyr Thr Trp Arg Thr Leu Gln His Met Lys Lys Arg Pro
145                 150                 155                 160

Ser Phe Arg Lys Thr Ser Ala Phe Pro Ser Lys Arg His Gln Val Leu
                165                 170                 175

His Ser Leu Ser Ser Gln Glu Gly Leu Asn Ser Pro Ile His
            180                 185                 190
```

<210> SEQ ID NO 9
<211> LENGTH: 805
<212> TYPE: PRT
<213> ORGANISM: Gossypium hirsutum

<400> SEQUENCE: 9

```
Met Ala Asn Pro Val Ile Thr Arg Val His Ser Leu Arg Glu Arg Leu
1               5                   10                  15

Asp Glu Thr Leu Leu Ala His Arg Asn Glu Ile Leu Ala Leu Leu Ser
            20                  25                  30

Arg Ile Glu Gly Lys Gly Lys Gly Ile Leu Gln His His Gln Ile Ile
        35                  40                  45

Leu Glu Phe Glu Ala Ile Pro Glu Glu Asn Arg Lys Lys Leu Ala Asp
    50                  55                  60

Gly Ala Phe Phe Glu Val Leu Lys Ala Ser Gln Glu Ala Ile Val Leu
65                  70                  75                  80

Pro Pro Trp Val Ala Leu Ala Val Arg Pro Arg Pro Gly Val Trp Glu
                85                  90                  95

Tyr Ile Arg Val Asn Val His Ala Leu Val Val Glu Glu Leu Thr Val
            100                 105                 110

Ala Glu Tyr Leu His Phe Lys Glu Glu Leu Val Asp Gly Ser Ser Asn
        115                 120                 125

Gly Asn Phe Val Leu Glu Leu Asp Phe Glu Pro Phe Asn Ser Ser Phe
    130                 135                 140

Pro Arg Pro Thr Leu Ser Lys Ser Val Gly Asn Gly Val Glu Phe Leu
145                 150                 155                 160

Asn Arg His Leu Ser Ala Lys Leu Phe His Asp Lys Glu Ser Met His
```

```
                        165                 170                 175
Pro Leu Leu Glu Phe Leu Arg Val His Cys His Lys Gly Lys Asn Met
            180                 185                 190

Met Leu Asn Asp Arg Ile Gln Asn Leu Asn Ala Leu Gln His Val Leu
            195                 200                 205

Arg Lys Ala Glu Glu Tyr Leu Gly Thr Leu Pro Pro Glu Thr Pro Cys
            210                 215                 220

Ala Gly Phe Glu His Arg Phe Gln Glu Ile Gly Leu Glu Arg Gly Trp
225                 230                 235                 240

Gly Asp Thr Ala Gln Arg Val Leu Glu Met Ile Gln Leu Leu Leu Asp
            245                 250                 255

Leu Leu Glu Ala Pro Asp Pro Cys Thr Leu Glu Lys Phe Leu Gly Arg
            260                 265                 270

Ile Pro Met Val Phe Asn Val Ile Leu Thr Pro His Gly Tyr Phe
            275                 280                 285

Ala Gln Asp Asn Val Leu Gly Tyr Pro Asp Thr Gly Gly Gln Val Val
            290                 295                 300

Tyr Ile Leu Asp Gln Val Arg Ala Leu Glu Asn Glu Met Leu Leu Arg
305                 310                 315                 320

Ile Lys Gln Gln Gly Leu Asn Ile Thr Pro Arg Ile Leu Ile Ile Thr
            325                 330                 335

Arg Leu Leu Pro Asp Ala Val Gly Thr Thr Cys Gly Gln Arg Leu Glu
            340                 345                 350

Lys Val Tyr Gly Thr Glu Tyr Ser Asp Ile Leu Arg Val Pro Phe Arg
            355                 360                 365

Thr Glu Lys Gly Ile Val Arg Lys Trp Ile Ser Arg Phe Glu Val Trp
            370                 375                 380

Pro Tyr Leu Glu Thr Tyr Thr Glu Asp Val Ala His Glu Ile Ser Lys
385                 390                 395                 400

Glu Leu Gln Gly Lys Pro Asp Leu Ile Ile Gly Asn Tyr Ser Asp Gly
            405                 410                 415

Asn Ile Val Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
            435                 440                 445

Tyr Trp Lys Lys Leu Glu Asp Lys Tyr His Phe Ser Cys Gln Phe Thr
            450                 455                 460

Ala Asp Leu Phe Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
            485                 490                 495

His Thr Ala Phe Thr Leu Pro Gly Leu Tyr Arg Val Val His Gly Ile
            500                 505                 510

Asp Val Phe Asp Pro Lys Phe Asn Ile Val Ser Pro Gly Ala Asp Met
            515                 520                 525

Glu Ile Tyr Phe Pro Tyr Thr Glu Glu Lys Arg Arg Leu Lys His Phe
            530                 535                 540

His Thr Glu Ile Glu Asp Leu Leu Tyr Ser Lys Val Glu Asn Glu Glu
545                 550                 555                 560

His Leu Cys Val Leu Asn Asp Arg Asn Lys Pro Ile Leu Phe Thr Met
            565                 570                 575

Ala Arg Leu Asp Arg Val Lys Asn Leu Thr Gly Leu Val Glu Trp Tyr
            580                 585                 590
```

Gly Lys Asn Ala Lys Leu Arg Glu Leu Ala Asn Leu Val Val Gly
            595                 600                 605

Gly Asp Arg Arg Lys Glu Ser Lys Asp Leu Glu Lys Ala Glu Met
610                 615                 620

Lys Lys Met Phe Glu Leu Ile Glu Lys Tyr Asn Leu Asn Gly Gln Phe
625                 630                 635                 640

Arg Trp Ile Ser Ser Gln Met Asn Arg Ile Arg Asn Gly Glu Leu Tyr
                645                 650                 655

Arg Tyr Ile Cys Asp Thr Lys Gly Ala Phe Val Gln Pro Ala Leu Tyr
            660                 665                 670

Glu Ala Phe Gly Leu Thr Val Val Glu Ala Met Thr Cys Gly Leu Pro
                675                 680                 685

Thr Phe Ala Thr Cys Asn Gly Gly Pro Ala Glu Ile Ile Val His Gly
690                 695                 700

Lys Ser Gly Phe Asn Ile Asp Pro Tyr His Gly Asp Gln Ala Ala Asp
705                 710                 715                 720

Ile Leu Val Asp Phe Phe Glu Lys Cys Lys Asp Pro Ser His Trp
                725                 730                 735

Asp Lys Ile Ser Gln Gly Gly Leu Lys Arg Ile Glu Glu Lys Tyr Thr
            740                 745                 750

Trp Lys Ile Tyr Ser Glu Arg Leu Leu Thr Leu Thr Gly Val Tyr Gly
                755                 760                 765

Phe Trp Lys His Val Ser Asn Leu Glu Arg Arg Glu Ser Arg Arg Tyr
770                 775                 780

Leu Glu Met Phe Tyr Ala Leu Lys Tyr Arg Lys Leu Ala Glu Ser Val
785                 790                 795                 800

Pro Leu Ala Glu Glu
            805

<210> SEQ ID NO 10
<211> LENGTH: 195
<212> TYPE: PRT
<213> ORGANISM: Gossypium hirsutum

<400> SEQUENCE: 10

Met Glu Arg Gly Phe Ile Val Leu Ala Leu Thr Val Val Phe Ala Ala
1               5                   10                  15

Thr Val Val Thr Ala Ala Asp Glu Ser Gly Leu Ala Asn Glu Cys Ser
            20                  25                  30

Lys Asp Phe Gln Ser Val Met Thr Cys Leu Ser Phe Ala Gln Gly Lys
        35                  40                  45

Ala Ala Ser Pro Ser Lys Glu Cys Cys Asn Ser Val Ala Gly Ile Lys
    50                  55                  60

Glu Asn Lys Pro Lys Cys Leu Cys Tyr Ile Leu Gln Gln Thr Gln Thr
65                  70                  75                  80

Ser Gly Ala Gln Asn Leu Lys Ser Leu Gly Val Gln Glu Asp Lys Leu
                85                  90                  95

Phe Gln Leu Pro Ser Ala Cys Gln Leu Lys Asn Ala Ser Val Ser Asp
            100                 105                 110

Cys Pro Lys Leu Leu Gly Leu Ser Pro Ser Pro Asp Ala Ala Ile
        115                 120                 125

Phe Thr Asn Ser Ser Lys Ala Thr Thr Pro Ser Thr Ser Thr
    130                 135                 140

Thr Ala Thr Pro Ser Ser Ala Ala Asp Lys Thr Asp Ser Lys Ser Ser
145                 150                 155                 160

```
Gly Ile Lys Leu Gly Pro His Phe Val Gly Ser Thr Ala Ala Leu Leu
            165                 170                 175

Val Ala Thr Ala Ala Val Phe Phe Leu Val Phe Pro Ala Gly Phe Ala
            180                 185                 190

Ser Ile Val
        195

<210> SEQ ID NO 11
<211> LENGTH: 123
<212> TYPE: PRT
<213> ORGANISM: Gossypium hirsutum

<400> SEQUENCE: 11

Met Ala Ser Ser Gly Val Leu Lys Leu Val Ser Met Ile Leu Met Val
1               5                   10                  15

Cys Met Thr Met Met Ser Ala Pro Lys Ala Ala Lys Ala Ala Ile Thr
            20                  25                  30

Cys Ser Asp Val Val Asn His Leu Ile Pro Cys Leu Ser Tyr Val Gln
        35                  40                  45

Asn Gly Gly Thr Pro Ala Ala Ala Cys Cys Ser Gly Val Lys Ala Leu
    50                  55                  60

Tyr Gly Glu Val Gln Thr Ser Pro Asp Arg Gln Asn Val Cys Lys Cys
65                  70                  75                  80

Ile Lys Ser Ala Val Asn Gly Ile Pro Tyr Thr Ser Asn Asn Leu Asn
                85                  90                  95

Leu Ala Ala Gly Leu Pro Ala Lys Cys Gly Leu Gln Leu Pro Tyr Ser
            100                 105                 110

Ile Ser Pro Ser Thr Asp Cys Asn Lys Val Gln
        115                 120

<210> SEQ ID NO 12
<211> LENGTH: 282
<212> TYPE: PRT
<213> ORGANISM: Gossypium hirsutum

<400> SEQUENCE: 12

Pro Arg Val Arg Pro Arg Val Arg Ala His Leu Pro Lys Arg Thr Asp
1               5                   10                  15

Asn Glu Ile Lys Asn Tyr Trp Asn Thr Gln Leu Lys Lys Arg Leu Thr
            20                  25                  30

Thr Ile Gly Ile Asp Pro Ala Thr His Arg Pro Lys Thr Asp Thr Leu
        35                  40                  45

Gly Ser Thr Pro Lys Asp Ala Ala Asn Leu Ser His Met Ala Gln Trp
    50                  55                  60

Glu Ser Ala Arg Leu Glu Ala Glu Ala Arg Leu Val Arg Glu Ser Lys
65                  70                  75                  80

Arg Val Ser Asn Pro Ser Gln Asn Gln Phe Arg Phe Thr Ser Ser Ser
                85                  90                  95

Ala Pro Pro Leu Val Ser Lys Ile Asp Val Gly Leu Ala His Ala Thr
            100                 105                 110

Lys Pro Gln Cys Leu Asp Val Leu Lys Ala Trp Gln Arg Val Val Thr
        115                 120                 125

Gly Leu Phe Thr Phe Asn Thr Asp Asn Leu Gln Ser Pro Thr Ser Thr
    130                 135                 140

Ser Ser Phe Thr Glu Asn Thr Leu Pro Ile Ser Ser Val Gly Phe Ile
145                 150                 155                 160

Asp Ser Phe Val Gly Asn Ser Asn Asn Ser Cys Cys Gly Asn Asn Trp
```

-continued

```
                165                 170                 175
Glu Cys Val Glu Lys Ser Ser Gln Val Ala Glu Leu Gln Glu Arg Leu
            180                 185                 190

Asp Asn Ser Met Gly Leu His Asp Ile Leu Asp Leu Ser Ser Glu Asp
        195                 200                 205

Val Trp Phe Gln Gly Ser Tyr Arg Ala Glu Asn Met Met Glu Gly Tyr
    210                 215                 220

Ser Asp Thr Leu Met Val Cys Asp Ser Gly Asp His Pro Lys Ser Leu
225                 230                 235                 240

Ser Met Glu Pro Arg Gln Asn Phe Asn Val Gly Thr Ser Asn Ala Ser
                245                 250                 255

Ser Phe Glu Glu Asn Lys Asn Tyr Trp Asn Asn Ile Leu Asn Phe Ala
            260                 265                 270

Asn Ala Ser Pro Ser Gly Ser Ser Val Phe
                275                 280

<210> SEQ ID NO 13
<211> LENGTH: 177
<212> TYPE: PRT
<213> ORGANISM: Gossypium hirsutum

<400> SEQUENCE: 13

Met Lys Val Leu Ser Pro Ile Leu Ala Cys Leu Ala Leu Ala Val Val
1               5                   10                  15

Ala Ser His Ala Ala Leu Ser Pro Glu Gln Tyr Trp Ser Tyr Lys Leu
            20                  25                  30

Pro Asn Thr Pro Met Pro Lys Ala Val Lys Glu Ile Leu His Pro Glu
        35                  40                  45

Leu Met Glu Glu Lys Ser Thr Ser Val Asn Val Gly Gly Gly Gly Val
    50                  55                  60

Asn Val Asn Thr Gly Lys Gly Lys Pro Ala Gly Gly Thr His Val Asn
65                  70                  75                  80

Val Gly Arg Lys Gly Val Gly Val Asn Thr Gly Lys Pro Gly Gly Gly
                85                  90                  95

Thr His Val Asn Val Gly Gly Lys Gly Val Gly Val Asn Thr Gly Lys
            100                 105                 110

Pro Gly Gly Gly Thr His Val Asn Val Gly Gly Lys Gly Gly Gly Val
        115                 120                 125

Ser Val His Thr Gly His Lys Gly Lys Pro Val Asn Val Asn Val Ser
    130                 135                 140

Pro Phe Leu Tyr Gln Tyr Ala Ala Ser Glu Thr Gln Ile His Asp Asp
145                 150                 155                 160

Pro Asn Val Ala Leu Phe Phe Leu Glu Lys Asp Leu His Pro Gly Gln
                165                 170                 175

Gln

<210> SEQ ID NO 14
<211> LENGTH: 282
<212> TYPE: PRT
<213> ORGANISM: Gossypium hirsutum

<400> SEQUENCE: 14

Leu Ser Glu Ser Lys Glu Met Val Phe Gln Phe Asn Phe Pro Val Leu
1               5                   10                  15

Leu Leu Cys Leu Met Phe Leu Met Cys Gly Arg Gly Asn Ala Val Arg
            20                  25                  30
```

```
Asp Leu Glu Gly Lys His Asp Phe Glu Ser His Gly Arg Asp Asp Glu
        35                  40                  45

Val Glu Ser Leu Asp Asp Lys Tyr Val Ser Ala Tyr Phe His Gln Thr
 50                  55                  60

Phe Asp Ser Ala Asn His Phe Asp Gly Gly Asp Glu Val Lys Asn Leu
 65                  70                  75                  80

Glu Asp Lys Tyr Ser Thr Ala Tyr Phe His Lys Ser Leu Asp Ser Gly
                 85                  90                  95

Asn His Gly Arg Asp Asp Lys Ala Lys Ile Leu Glu Asp Lys Tyr Ala
                100                 105                 110

Thr Ala Tyr Phe His Lys Thr Ser Val Phe Glu Asn His Gly Glu Gly
            115                 120                 125

Asp Lys Leu Lys Ser Leu Glu Asp Lys Tyr Ser Ala Ala Tyr Phe His
        130                 135                 140

Asn Thr Gln Ser Ser Lys Met Met Lys Asp His Asn Met Glu His His
145                 150                 155                 160

His His Tyr His Asn His Val Glu Ser Ala Glu Ile Gly Leu Phe Thr
                165                 170                 175

Ile Asp Glu Leu His Thr Phe Asn Val Gly Lys Lys Leu Pro Ile Phe
            180                 185                 190

Phe Pro Ile Lys Asn His Ser Leu Tyr Pro Pro Leu Leu Pro Lys Gln
        195                 200                 205

Ile Ala Asp Thr Ile Pro Phe Ser Ser Phe Gln Val Ser Asn Ile Leu
    210                 215                 220

Arg Phe Phe Ser Val Ser Pro Asp Ser Pro Lys Gly Lys Ser Cys Ser
225                 230                 235                 240

Arg Tyr Leu Arg Lys Met Arg Thr Arg Ser Ser Ala Arg Gly Arg Pro
                245                 250                 255

Lys Ile Trp Ala Thr Ser Leu Lys Ser Leu His Gly Phe Leu Ser Met
            260                 265                 270

His Leu Gly Pro Met Leu Ile Ser Ser Ser
        275                 280

<210> SEQ ID NO 15
<211> LENGTH: 55
<212> TYPE: PRT
<213> ORGANISM: Gossypium hirsutum

<400> SEQUENCE: 15

Lys Trp Glu Ala Gly Gln Ser Gln Cys Met Val Val Leu Val Phe Thr
 1               5                  10                  15

Gln Ile Ser Leu Val Lys Gly Lys Arg Lys Leu Cys Tyr Ser Ser Ile
             20                  25                  30

Val Ala Leu Ile Leu Glu Ser Val Leu Phe Val Leu Thr Phe Pro Ala
         35                  40                  45

Leu Thr Asp Met Asn Leu Tyr
     50                  55

<210> SEQ ID NO 16
<211> LENGTH: 235
<212> TYPE: PRT
<213> ORGANISM: Gossypium hirsutum

<400> SEQUENCE: 16

Met Pro Arg Thr Arg Arg Phe Asn Pro Pro Ser Ile Thr Ser Arg Thr
 1               5                  10                  15

Leu Gly His His Val Tyr Lys Asp Asp Asn Pro Ile Val Tyr Gly Thr
```

```
                20                  25                  30
Met Gln Ala Tyr Leu Lys Asp Ala Arg Glu Arg Leu Phe Asn Thr Ala
        35                  40                  45
Arg Thr Ala Glu Lys Leu Gly Ile His Met Gly Phe Lys Leu Val Arg
    50                  55                  60
Gly Ala Tyr Met Ser Ser Glu Thr Lys Leu Ala Ser Ser Leu Gly Phe
65                  70                  75                  80
Asp Ser Pro Val His Asn Thr Ile Gln Asp Thr His Ala Cys Phe Asn
                85                  90                  95
Asp Cys Ala Ser Phe Met Ile Glu Lys Ile Ala Asp Gly Tyr Gly Gly
            100                 105                 110
Leu Val Leu Ala Thr His Asn Leu Glu Ser Gly Lys Leu Ala Ala Ser
        115                 120                 125
Lys Ala Arg Asn Leu Gly Ile Glu Lys Gly Asn Gln Lys Leu Glu Phe
    130                 135                 140
Ala Gln Leu Tyr Gly Met Ser Glu Ala Leu Ser Ile Gly Leu Arg Asn
145                 150                 155                 160
Ala Gly Phe Gln Val Ser Lys Tyr Leu Pro Tyr Gly Pro Val Asp Met
                165                 170                 175
Val Met Pro Tyr Leu Arg Arg Ala Glu Glu Asn Arg Gly Leu Leu
            180                 185                 190
Ser Thr Ser Ser Leu Asp Arg Thr Leu Met Gly Lys Glu Leu Lys Arg
        195                 200                 205
Arg Leu Lys Ser Leu Gln Phe Ala Lys Pro Glu Met Ala Ala Ser Ala
    210                 215                 220
Ala Gly Ser Met Lys Ile Glu Ile Gly Thr Pro
225                 230                 235

<210> SEQ ID NO 17
<211> LENGTH: 2207
<212> TYPE: DNA
<213> ORGANISM: Gossypium hirsutum

<400> SEQUENCE: 17
gtcaagttct ggttccaaaa caagcgcacc caaatgaagg cccaacatga acgccatgaa        60
aatgctatac tgaaggctga gaatgaaaaa ctccgagctg agaataatag gtacaaggaa       120
gctctcagca atgctacatg ccccagctgt ggaggcccag ctgcccttgg agagatgtca       180
tttgatgagc aacatttgag aatagaaaat gctcggttaa gggaagagat tgataggata       240
tctggaatag ctgctaaata tgttggcaag cctttatctt cattgcctca cctttcatct       300
catttacatt cgcgctctgc tgatcttgga gctagcaatt cgggaatcaa atcaggattt       360
gtaggggaaa tggatcgcag tggtgatctt ctgaggtctg tctctggacc tacagaagcg       420
gataagccca tgattgttga gcttgctgtt gctgcaatgg aggaactaat acgaatggcc       480
caatctgggg aacctttgtg ggttcctggg acaattctca gatgtgtt gaacgaagat        540
gaatacttaa gaactttccc taggggaatt ggaccaaagc ctttgggg tt gaggtctgaa       600
gcttcaagag aatctgcagt tgtcatcatg aatcatgtca acttagttga gattctcatg       660
gatgtgaatc aatggtcaag tgtgttttgc ggtattgttt caagggctat gactttagaa       720
gtcctatcaa ctggagttgc aggaaactac aatgggcct tgcaagtgat gacggctgag       780
ttccaagtcc cttcaccact tgtaccaact cgggaaaatt atttcgcgag gtactgtaag       840
cagcatattg atggaacttg ggcagtggtt gatgtttcct tggataattt cgcccctaac       900
ccaatgtcaa gtgtagagag gccctcaggt tgcttgatcc agaattgcca aatggatacc       960
```

```
tctaaggtta tatgggtcga gcatgtagaa gtggatgata gagctgtcca caacatatac    1020
agaccagtag ttaattccgg tctagctttt ggagcaaaac gttgggtggc tacgttggat    1080
cgacagtgtg agcgtctagc aagttcaatg gccagtaaca ttccagcagg ggtctatgc     1140 gttataacaa gcccagaagg gaggaaaagt atgttgaagt tggcagagag gatggtgact    1200
agcttttgta caggtgttgg tgcttctacg gcccatgctt ggacaacttt atcggcaaca    1260
ggctccgatg atgtgcgggt tatgacccga aagagcatgg atgatccagg aaggcctcct    1320
ggtattgtac ttagtgctgc aacttccttc tggatccaag ttccaccaaa gagggtattt    1380
gatttcctaa gggatgagaa ctctagaagt gagtgggata tcctatcaaa tggtggccta    1440
gttcaagaaa tggctcacat agctaatggt cgtgatccag gcaattgtgt ctctttactc    1500
cgcgtaaata gtgcaaactc tagccaaagc aacatgttga tacttcaaga gagctgcact    1560
gatgctaaag gtcctacgt gatatatgcc ccggtcaata ttgttgcaat gaacatcgtc     1620
ttaagtggcg gggacccgga ttatgtcgca ctattgccat ccggtttcgc aattcttccc    1680
gatggtccag gagttaatgg aggagggatc ctcgaaatcg gctcgggtgg ctctctcctt    1740
accgttgctt tccagatttt ggttgattca gttcccacag caaagctttc tcttggatca    1800
gtggcgactg tcaacagtct aattaaatgc acggttgaaa ggatcaaggc tgccgtaaag    1860
tgcaataatg cttgaccaaa catgatataa aaaaggaaa cgagaagaaa aggtgtttgt     1920
ccgaaaacaa atttaacgat tgaagaagtc aagagcgcac ctttcaattc atcctttgcg    1980
gtcatggtgt tctgtaagaa ggcaaaatca tcaagcctgc aaggatagta ggttcgggaa    2040
ttgactttgc caacgagatt ctaatattag atatgttggg agaactcccc attttgtgta    2100
ggctaagagt tcaatgtagg agtggacttt atactagtct aatttctttc tggtttcatg    2160
tgttattgtt gaagcattag ttaatttgga cttattcctc cattaac                  2207
```

<210> SEQ ID NO 18
<211> LENGTH: 1872
<212> TYPE: DNA
<213> ORGANISM: Gossypium hirsutum

<400> SEQUENCE: 18

```
gtcaagttct ggttccaaaa caagcgcacc caaatgaagg cccaacatga acgccatgaa      60
aatgctatac tgaaggctga gaatgaaaaa ctccgagctg agaataatag gtacaaggaa     120
gctctcagca atgctacatg ccccagctgt ggaggcccag ctgcccttgg agagatgtca     180
tttgatgagc aacatttgag aatagaaaat gctcggttaa gggaagagat tgataggata     240
tctggaatag ctgctaaata tgttggcaag cctttatctt cattgcctca cctttcatct     300
catttacatt cgcgctctgc tgatcttgga gctagcaatt cgggaatcga atcaggattt     360
gtaggggaaa tggatcgcag tggtgatctt ctgaggtctg tctctggacc tacagaagcg     420
gataagccca tgattgttga gcttgctgtt gctgcaatgg aggaactaat acgaatggcc    480
caatctgggg aacctttgtg ggttcctggg gacaattcta cagatgtgtt gaacgaagat    540
gaatacttaa gaactttccc taggggaatt ggaccaaagc ctttggggtt gaggtctgaa    600
gcttcaagag aatctgcagt tgtcatcatg aatcatgtca acttagttga gattctcatg    660
gatgtgaatc aatggtcaag tgtgttttgc ggtattgttt caaggctat gactttagaa     720 gtcctatcaa ctggagttgc aggaaactac aatggggcct tgcaagtgat gacggctgag    780
ttccaagtcc cttcaccact tgtaccaact cgggaaaatt atttcgcgag gtactgtaag    840
cagcatattg atggaacttg gcagtggtt gatgtttcct tggataattt acgccctaac    900
```

```
ccaatgtcaa gtgtagagag gccctcaggt tgcttgatcc agaattgcca aatggatacc      960
tctaaggtta tatgggtcga gcatgtagaa gtggatgata gagctgtcca caacatatac     1020
agaccagtag ttaattccgg tctagctttt ggagcaaaac gttgggtggc tacgttggat     1080
cgacagtgtg agcgtctagc aagttcaatg gccagtaaca ttccagcagg gggtctatgc     1140
gttataacaa gcccagaagg gaggaaaagt atgttgaagt tggcagagag gatggtgact     1200
agcttttgta caggtgttgg tgcttctacg gcccatgctt ggacaacttt atcggcaaca     1260
ggctccgatg atgtgcgggt tatgacccga aagagcatgg atgatccagg aaggcctcct     1320
ggtattgtac ttagtgctgc aacttccttc tggatccaag ttccaccaaa gagggtattt     1380
gatttcctaa gggatgagaa ctctagaagt gagtgggata tcctatcaaa tggtggccta     1440
gttcaagaaa tggctcacat agctaatggt cgtgatccag gcaattgtgt ctctttactc     1500
cgcgtaaata gtgcaaactc tagccaaagc aacatgttga tacttcaaga gagctgcact     1560
gatgctaaag gtcctacgt gatatatgcc ccggtcaata ttgttgcaat gaacatcgtc     1620
ttaagtggcg gggacccgga ttatgtcgca ctattgccat ccggtttcgc aattcttccc     1680
gatggtccag gagttaatgg aggagggatc ctcgaaatcg gctcgggtgg ctctctcctt     1740
accgttgctt ccagattttt ggttgattca gttcccacag caaagctttc tcttggatca     1800
gtggcgactg tcaacagtct aattaaatgc acggttgaaa ggatcaaggc tgccgtaaag     1860
tgcaataatg ct                                                        1872

<210> SEQ ID NO 19
<211> LENGTH: 1180
<212> TYPE: DNA
<213> ORGANISM: Gossypium hirsutum

<400> SEQUENCE: 19
tagaaattgt tatacagttc tagctaaggt tcatttgaaa gatacataca tacacacaca       60
tatatatatg gggagatcac catgttgtga aaaggtaggg ttgaagaaag gtccatggac      120
cccagaagaa gatcaaaagc tcttagctta cattgaacaa catggccatg aagctggcg      180 tgccttgcct tcaaaagctg gcttcaaag atgtggaaag agttgcagac tgagatggat      240
taactacttg agacctgata tcaaaagagg aaagttcagt ttacaagaag aacagaccat      300
tattcaactc catgcccttc ttggaaacag gtggtctgcc atagctactc atttgccgaa      360
aagaacagac aatgagatca agaactactg gaacacacat ctaatgaaaa ggctaaccaa      420
aatggggatc gatcctgtca cccacaagcc taaaaccgat gcactcggct ccaccactgg      480
taaccctaaa gatgctgcta accttagtca catggctcaa tgggagagtg ctcgtttaga      540
agctgaagct agactggttc gtgagtccaa gctagttcct tcaaaccctc tcaaagcaa      600 ccatttcact gccgttgcgc cttcgccgac tccggcaact agaccgcaat gcctcgacgt      660
actcaaagca tggcaaggtg tcgtctgcgg gttattcact ttcaacatgg acaataacaa      720
cttacagtcc cctacgtcaa cgttgaactt catggagaac accacaacat gcccatgtc      780 atcatcatcg tctgttaatg gaatgtttaa tgaaaacttt ggttggaact catcgattaa      840
tccatgtgaa gtgggggata atttgaaagt tgaatatggc agtgatcaaa ttccagagtt      900
aaaggaaaga ttggatcatc caatggaatt gcatgaaatg gactattctt cagagggtac      960
atggttccaa gagttgtttg gatttaatgg tttatgattc tgcagaagga ttcatcaaag     1020
gaaagaaagc tatctggttt catctttgaa gttcacttaa gtgtaggatt tttattcaca     1080
agtgccttca catattacca ttaactgtaa taataaaacct tcaaattaat aaattaaaaa     1140
```

```
actcacaagg ttttttggcc aaaaaaaaaa aaaaaaaaa                          1180
```

```
<210> SEQ ID NO 20
<211> LENGTH: 927
<212> TYPE: DNA
<213> ORGANISM: Gossypium hirsutum

<400> SEQUENCE: 20
atggggagat caccatgttg tgaaaaggta gggttgaaga aaggtccatg gaccccagaa      60
gaagatcaaa agctcttagc ttacattgaa caacatggcc atggaagctg gcgtgccttg     120
ccttcaaaag ctgggcttca agatgtggaa agagttgca gactgagatg gattaactac      180
ttgagacctg atatcaaaag aggaaagttc agtttacaag aagaacagac cattattcaa     240
ctccatgccc ttcttggaaa caggtggtct gccatagcta ctcatttgcc gaaaagaaca     300
gacaatgaga tcaagaacta ctggaacaca catctaatga aaaggctaac caaaatgggg     360
atcgatcctg tcacccacaa gcctaaaacc gatgcactcg gctccaccac tggtaaccct     420
aaagatgctg ctaaccttag tcacatggct caatgggaga gtgctcgttt agaagctgaa     480
gctagactgg ttcgtgagtc caagctagtt ccttcaaacc ctcctcaaag caaccatttc     540
actgccgttg cgccttcgcc gactccggca actagaccgc aatgcctcga cgtactcaaa     600
gcatggcaag gtgtcgtctg cgggttattc actttcaaca tggacaataa caacttacag     660
tccctacgt caacgttgaa cttcatggag aacaccacaa cattgcccat gtcatcatca      720
tcgtctgtta atggaatgtt taatgaaaac tttggttgga actcatcgat taatccatgt     780
gaaagtgggg ataatttgaa agttgaatat ggcagtgatc aaattccaga gttaaaggaa     840
agattggatc atccaatgga attgcatgaa atggactatt cttcagaggg tacatggttt     900
caagagttgt ttggatttaa tggttta                                         927
```

```
<210> SEQ ID NO 21
<211> LENGTH: 600
<212> TYPE: DNA
<213> ORGANISM: Gossypium hirsutum

<400> SEQUENCE: 21
agcgatgtga gcgtctcctc ctctgtgtaa tctctgatgc aagatccatc cattatcttc      60
cctctgtatt ggctactgca accatgatgc acgtcataga ccaagttgag cttttcaatc     120
ccattgacta ccaaaatcag ctgctgagtg ttcttaaaat tagcaaggaa aaagtaaacg     180
attgttacaa gctcatcctt gatgtatcaa caagacccca ggcccaaggc aatggtggtg     240
catgtaagag gaaggtggag gagagggttc ctagcagccc tagtggagtg attgatgctg     300
catttggcag tgatagctcg agcgattctt ggggcacggt gtccttatcg cctgagcagc     360
agccaccttt taagaagagc agagcccaag agcaagtaat gcgtttgcca tcactcaacc     420
gagtctttgt agacattgtt ggcagccctt cttaattata tctcccttct ctctctccct     480
cgctctctcc atctctttct ttgtcccaaa aagatctata tttattatgc ttatgttcac     540
ttttggttca aggaatcaaa tgttaagtta aaaaaatgaa aaaacaaag taaagctgc       600
```

```
<210> SEQ ID NO 22
<211> LENGTH: 452
<212> TYPE: DNA
<213> ORGANISM: Gossypium hirsutum

<400> SEQUENCE: 22
agcgatgtga gcgtctcctc ctctgtgtaa tctctgatgc aagatccatc cattatcttc      60
```

```
cctctgtatt ggctactgca accatgatgc acgtcataga ccaagttgag cttttcaatc      120
ccattgacta ccaaaatcag ctgctgagtg ttcttaaaat tagcaaggaa aaagtaaacg      180
attgttacaa gctcatcctt gatgtatcaa caagacccca ggcccaaggc aatggtggtg      240
catgtaagag gaaggtggag gagagggttc ctagcagccc tagtggagtg attgatgctg      300
catttggcag tgatagctcg agcgattctt ggggcacggt gtccttatcg cctgagcagc      360
agccaccttt taagaagagc agagcccaag agcaagtaat gcgtttgcca tcactcaacc      420
gagtctttgt agacattgtt ggcagcccct ct                                   452

<210> SEQ ID NO 23
<211> LENGTH: 704
<212> TYPE: DNA
<213> ORGANISM: Gossypium hirsutum

<400> SEQUENCE: 23
gctgaacacc ccaaagatgg ccaaccacac cgttaccttt ctccctaaac tatccattga       60
agctattcag acagtgactc cgatgaggat aactgaacca cgacagactc gacaagtatt      120
ggcaggggag cttgtaggac ccgggatttt ccaaaggtgt ttgaacgtgg tccagtacta      180
catgaaggag aaagaagaag actctggttg gttactggct gggtggatca aggaaacact      240
tgggagagct ttacatgagc aaccaatgat ttctggtcgt cttcggaaag gggaacgaaa      300
cgatggagaa ttggagattg tttccaatga ctgcggcatt agactcattg aggcaaggat      360
tcagatgaat ctgtcggatt tcttgattt gaaacaaagg gaagatgctg aagctcagct       420
tgttttctgg aaagatattg atgagcaaaa cccacagttc tccccactct tttatgttca      480
ggttactaat ttccagtgtg gtggatattc aattgggatt agctgcagta ttcttctggc      540
agatcttttg ttaatgaaag aattccttaa gacatgggca gatattccaa caaggttatt      600
atcaacaaaa acgatgaaca aaagcttcct ttattctacc ttcctggctg aaaaacacca      660
atggtgcctc cctacatcat cacatcaaat tcaagcaaaa ctca                      704

<210> SEQ ID NO 24
<211> LENGTH: 548
<212> TYPE: DNA
<213> ORGANISM: Gossypium hirsutum
<220> FEATURE:
<221> NAME/KEY: misc_feature
<222> LOCATION: (491)..(491)
<223> OTHER INFORMATION: n = unknown

<400> SEQUENCE: 24
ctgagttaag agtttcaatt cttctactta ttatagttaa atatcatata tggccaagta       60
cttgaatgtt gtgcttgttc ttgctctagt agtggttcaa gctactgcaa ggaatgtgcc      120
tagcgatgct gctggtctca atgaccaaaa gaacctcctc acatacggtg gcattggcgg      180
ctactctggc atgggttcaa atggcatgcc aatggggtgga gttgggagtg ttggtggtat      240 gactggccctt ggtggtacag gtgggatggg cgccatggta ggtgttgggt atggaggtgg      300
gcctggcgct ggtggtggaa atgaaggtgg tgttggcatt ggcaatgcgc ctggtgtcgt      360
ccactttcct tgaactttgc tggatggtta aaattttaaa gcaactagtt tcttgaactt      420
tgctggaggg gtttaaattt taagcaact agtctaactc acgttaaaga ataatattaa      480
tgttgctcta nagtgtgaaa tgttgtcctg tgtatgggtt atgtgataag tccatctttta     540 ttttttt                                                              548
```

-continued

```
<210> SEQ ID NO 25
<211> LENGTH: 321
<212> TYPE: DNA
<213> ORGANISM: Gossypium hirsutum

<400> SEQUENCE: 25
atggccaagt acttgaatgt tgtgcttgtt cttgctctag tagtggttca agctactgca      60
aggaatgtgc ctagcgatgc tgctggtctc aatgaccaaa agaacctcct cacatacggt     120
ggcattggcg gctactctgg catgggttca aatggcatgc caatgggtgg agttgggagt     180
gttggtggta tgactggcct tggtggtaca ggtgggatgg gcgccatggt aggtgttggg     240
tatggaggtg ggcctggcgc tggtggtgga aatgaaggtg gtgttggcat ggcaatgcg      300 cctggtgtcg tccactttcc t                                                321

<210> SEQ ID NO 26
<211> LENGTH: 727
<212> TYPE: DNA
<213> ORGANISM: Gossypium hirsutum
<220> FEATURE:
<221> NAME/KEY: misc_feature
<222> LOCATION: (26)..(26)
<223> OTHER INFORMATION: n = unknown

<400> SEQUENCE: 26
ccaaaatgta agtcttcaaa accaanagaa gaaactgtaa agcagtagta atgcaaatgc      60
ttagacactc aaatataagt agcaaactaa cctatgggtt atttggctga ttttgaaggg     120
ttcatggtgt attttggtgc gtgtctgtta agaatccgag ttgttgtccc gtggtattag     180
cttctctgtc ttgctggttg cgattgggca gttgtgacgt ctataatcaa gtgattcaag     240
gaaaccgtta gcttcatttt acttggagaa gacaaagaag ctattgttgt gctggacttg     300
ttcttgcttt ttctctttgt atggtgtggt ttatggtttg tattatgagt tttatatgaa     360
tagaactttg aatttggtga gaaaattaag aatgagcttg ggaggagcag aagtgttgat     420
ggcaatagca gggttgtggg cagtggtttt gaggccattg atgataaggt atgccgtaga     480
gatgagtcaa atgattggaa tttccgttag gagatttttc agtaatcctc tttcccttc      540 cgtatcgttt ttttattggt actgatatag aaattctatg aaatgagcac aatatgagac     600
accatttttt gctagccaag aagttagatg agtagtagac tttggtttaa gcttatcata     660
attgaaattg ttagactgta acccttttgt ctcctttctc taatttcaaa tccaaattcc     720
catcaat                                                                727

<210> SEQ ID NO 27
<211> LENGTH: 562
<212> TYPE: DNA
<213> ORGANISM: Gossypium hirsutum
<220> FEATURE:
<221> NAME/KEY: misc_feature
<222> LOCATION: (26)..(26)
<223> OTHER INFORMATION: n = unknown

<400> SEQUENCE: 27
ccaaaatgta agtcttcaaa accaanagaa gaaactgtaa agcagtagta atgcaaatgc      60
ttagacactc aaatataagt agcaaactaa cctatgggtt atttggctga ttttgaaggg     120
ttcatggtgt attttggtgc gtgtctgtta agaatccgag ttgttgtccc gtggtattag     180
cttctctgtc ttgctggttg cgattgggca gttgtgacgt ctataatcaa gtgattcaag     240
gaaaccgtta gcttcatttt acttggagaa gacaaagaag ctattgttgt gctggacttg     300
ttcttgcttt ttctctttgt atggtgtggt ttatggtttg tattatgagt tttatatgaa     360
```

```
tagaactttg aatttggtga gaaaattaag aatgagcttg ggaggagcag aagtgttgat      420
ggcaatagca gggttgtggg cagtggtttt gaggccattg atgataaggt atgccgtaga      480
gatgagtcaa atgattggaa tttccgttag gagattttt c agtaatcctc tttccccttc      540
cgtatcgttt ttttattggt ac                                               562
```

<210> SEQ ID NO 28
<211> LENGTH: 835
<212> TYPE: DNA
<213> ORGANISM: Gossypium hirsutum

<400> SEQUENCE: 28

```
tacggtggtg ctgatgctac cggcacaatg gggggagctt gtggttatgg aaacctgtac       60
agtcaaggga tggaacgag cacagcagct ttgagcactg cacttttcaa caatggcttg       120
agctgcggtg cctgctacga gctccggtgc aacaatgatc ctcaatggtg cattagtcga      180
accataaccg tgacagccac caacttttgt ccacctaact atgctttatc tagtgacaat      240
ggcgggtggt gcaatccccc acgagaacac tttgatttgg ccgaaccggc attcttgcgg      300
atagcagaat atcgagctgg aatcgtccct gttatgttca aagggtgtc atgtgtgaag       360 aaaggaggca tcaggtacac catgaatgga cattcgtact tcaacatggt gttgataacg      420
aacgtgggag gggcagggga tataacgtca gtgtccatca agggtccag aacaggatgg       480 ctacctatgt ccagaaattg gggccaaaac tggcagagca atgcttacct taacggacaa      540
agcctctctt ttaaagtgac tgccagcgat ggcaggacta tcacagccta caatgtagtg      600
cctgctggtt ggcaattcgg acaaactttt gaaggaggcc agttttaaga caatattata      660
gtgtctgtct aatataaaac tggaattgac atattactta taaggcac atgagcgttt       720 tatgccgagg tagcaaaatg gcgcccgctg gctttatgtg tgaaataggc gagcaagtgc      780
cattagccta taatctatac atttcttata gtgaaccaaa ctattaagtt tgaac           835
```

<210> SEQ ID NO 29
<211> LENGTH: 765
<212> TYPE: DNA
<213> ORGANISM: Gossypium hirsutum

<400> SEQUENCE: 29

```
tacggtggtg ctgatgctac cggcacaatg gggggagctt gtggttatgg aaacctgtac       60
agtcaagggt atggaacgag cacagcagct ttgagcactg cacttttcaa caatggcttg      120
agctgcggtg cctgctacga gctccggtgc aacaatgatc ctcaatggtg cattagtcga      180
accataaccg tgacagccac caacttttgt ccacctaact atgctttatc tagtgacaat      240
ggcgggtggt gcaatccccc acgagaacac tttgatttgg ccgaaccggc attcttgcgg      300
atagcagaat atcgagctgg aatcgtccct gttatgttca aagggtgtc atgtgtgaag       360 aaaggaggca tcaggtacac catgaatgga cattcgtact tcaacatggt gttgataacg      420
aacgtgggag gggcagggga tataacgtca gtgtccatca agggtccag aacaggatgg       480 ctacctatgt ccagaaattg gggccaaaac tggcagagca atgcttacct taacggacaa      540
agcctctctt ttaaagtgac tgccagcgat ggcaggacta tcacagccta caatgtagtg      600
cctgctggtt ggcaattcgg acaaactttt gaaggaggcc agttttaaga caatattata      660
gtgtctgtct aatataaaac tggaattgac atattactta taaggcac atgagcgttt       720 tatgccgagg tagcaaaatg gcgcccgctg gctttatgtg tgaaa                       765
```

<210> SEQ ID NO 30
<211> LENGTH: 985
<212> TYPE: DNA
<213> ORGANISM: Gossypium hirsutum

<400> SEQUENCE: 30

| | | | | | |
|---|---|---|---|---|---|
| tgtcccttc | tacagcagca | attacctatt | acatgagagc | tgcatgatga | tgatagcatc | 60 |
| actagttccc | aacttcatga | tgggagtcat | aattggagct | ggttatatag | gtttgctaat | 120 |
| gatgacagct | gggtatttca | gattgctgcc | agatctccct | aagatattct | ggcgttaccc | 180 |
| tgtttcatat | atcaactatg | gtgcatgggc | attgcaggga | gcatacaaga | atgatatggt | 240 |
| tgggcttgag | tttgatggct | tcatacctgg | tggtccaaaa | ctgaaaggtg | atgtcgtcct | 300 |
| cacatccatg | ctaggcatcc | atctggatca | ttcaaagtgg | tgggacttag | cagctgttat | 360 |
| aatgattttg | atagcttata | gattactttt | cttcatcatt | ctcaagttca | aggagagagt | 420 |
| gtcaccattg | tttcgaactc | tttatacatg | gcgaacattg | cagcacatga | aaaaacgacc | 480 |
| ttcttttagg | aaaacatcag | ccttcccatc | caagaggcac | caagttctac | attcactgtc | 540 |
| ttctcaagag | ggtctaaaact | ctccaattca | ctagaagcaa | caaatcatga | gtactatagt | 600 |
| aatgctctta | ctggaatttg | attacagaaa | caaagggaaa | gagattatag | tagaattaca | 660 |
| tatggaatta | cctgtatcag | ctttatttt | caagtgcttc | taatatctgc | ggactgttct | 720 |
| ggcattaatg | gcaagagagt | ttcccatcac | ccaagaatgg | tttgtttatg | gtcctcccta | 780 |
| gcaatggcga | tgaagagcag | aaacctgatt | tctgttgttg | caaccagtgc | tttgaagtaa | 840 |
| ccagatatga | taaacaggta | cagaaaatat | cccattgttc | ttcgtagata | atttcatctg | 900 |
| ccaaatgttt | gtagctgatg | cctcctacat | tatacaatgt | cataacatct | aatgatacca | 960 |
| ttatattgt | acgtaaaaaa | aaaaa | | | | 985 |

<210> SEQ ID NO 31
<211> LENGTH: 571
<212> TYPE: DNA
<213> ORGANISM: Gossypium hirsutum

<400> SEQUENCE: 31

| | | | | | |
|---|---|---|---|---|---|
| tgtcccttc | tacagcagca | attacctatt | acatgagagc | tgcatgatga | tgatagcatc | 60 |
| actagttccc | aacttcatga | tgggagtcat | aattggagct | ggttatatag | gtttgctaat | 120 |
| gatgacagct | gggtatttca | gattgctgcc | agatctccct | aagatattct | ggcgttaccc | 180 |
| tgtttcatat | atcaactatg | gtgcatgggc | attgcaggga | gcatacaaga | atgatatggt | 240 |
| tgggcttgag | tttgatggct | tcatacctgg | tggtccaaaa | ctgaaaggtg | atgtcgtcct | 300 |
| cacatccatg | ctaggcatcc | atctggatca | ttcaaagtgg | tgggacttag | cagctgttat | 360 |
| aatgattttg | atagcttata | gattactttt | cttcatcatt | ctcaagttca | aggagagagt | 420 |
| gtcaccattg | tttcgaactc | tttatacatg | gcgaacattg | cagcacatga | aaaaacgacc | 480 |
| ttcttttagg | aaaacatcag | ccttcccatc | caagaggcac | caagttctac | attcactgtc | 540 |
| ttctcaagag | ggtctaaaact | ctccaattca | c | | | 571 |

<210> SEQ ID NO 32
<211> LENGTH: 2611
<212> TYPE: DNA
<213> ORGANISM: Gossypium hirsutum

<400> SEQUENCE: 32

| | | | | | |
|---|---|---|---|---|---|
| caaagaaatg | gctaatcctg | tgatcactcg | cgtccacagt | ctccgtgagc | gtttagatga | 60 |
| gaccctttct | gcccacagga | acgagatttt | ggccttgctc | tcaaggatcg | agggcaaagg | 120 |

```
aaaaggaatt ctgcaacacc atcaaattat tctagagttt gaagctatcc ctgaagagaa      180
cagaaagaag ctcgctgatg gtgcattttt tgaagtattg aaggctagtc aggaagcgat      240
cgtgttgcct ccatgggttg cacttgctgt tcgtccaagg cctggtgttt gggagtacat      300
tagagtgaat gttcacgccc ttgttgttga ggaacttact gttgctgagt atctccactt      360
caaggaagag cttgttgatg gaagttcaaa tggaaacttt gttttggaat tggattttga      420
gcccttcaac tcatcattcc cccgcccaac tctttcaaaa tccgttggta atggtgtgga      480
gttcctaaat cgtcaccttt cggcaaaatt gttccatgac aaggagagca tgcacccttt      540
gctcgaattc ctcagagtcc attgccacaa gggcaagaac atgatgttga atgacagaat      600
tcagaacttg aatgctcttc aacatgtttt gaggaaagca gaggagtatc ttggtaccct      660
acctcctgag acaccatgtg ccggattcga acaccggttc caggaaatcg gtttggaaag      720
aggttggggt gacaccgcac aacgcgtgct cgagatgatc caactccttt tggatcttct      780
tgaggcacct gatccttgca cccttgagaa gttccttggg agaatcccca tggtgttcaa      840
tgttgtgatt ctcactcccc acggatactt cgctcaagac aatgttttgg ggtatcccga      900
caccggtggc caggttgttt acatcttgga tcaagtccga gctttggaga atgagatgct      960
cctccgtata aagcaacaag gactcaacat caccccctcga atcctcatta ttactagact     1020
tcttcctgat gctgtcggaa caacatgcgg tcaacgactt gagaaagtat acggaacaga     1080
gtactcggat attcttcgag tacccttcag aacagaaaag ggaattgttc gtaaatggat     1140
ctcaagattt gaagtctggc catacttgga aacctacaca gaggatgttg ctcatgaaat     1200
ctccaaagag ttgcaaggca agccagatct gatcatcgga aactacagtg atggcaatat     1260
cgtcgcctcc ttgctcgcac ataaattggg tgtcacacag tgcaccatcg cccatgcttt     1320
ggagaagaca aaatatcctg attcagatat ctactggaag aagcttgaag acaaatacca     1380
tttctcttgc caatttacag ctgatctttt tgcaatgaac catacagatt tcatcatcac     1440
cagtactttc caggaaattg caggaagcaa ggacactgtt ggtcaatacg agagccacac     1500
tgctttcact cttcctggtc tctaccgtgt tgtacatggt atcgatgtgt ttgatcccaa     1560
attcaacatt gtttcccctg gtgctgatat ggagatatac ttcccttaca ccgaagagaa     1620
gcggaggttg aagcatttcc atactgagat cgaagacctt ctttacagca agttgagaa     1680 tgaagaacac ttatgtgtgc tcaatgaccg caacaagcca attctgttca caatggcaag     1740
gcttgatcgt gtcaagaact taaccggact cgtcgagtgg tacggcaaga acgcaaagtt     1800
gcgtgagttg gctaaccctcg tagttgtagg tggtgatagg cgaaaggaat ctaaagattt     1860
ggaagagaag gccgaaatga agaaaatgtt tgagctgatc gagaagtaca acttgaacgg     1920
ccaattcaga tggatatcat ctcaaatgaa cagaatccga aatggtgaac tttaccgata     1980
catttgcgac acgaaaggtg cctttgtaca gcctgcattg tatgaagcct ttggattgac     2040
agttgtggag gcaatgactt gcggtttgcc aacattcgca acctgcaacg gtggaccagc     2100
cgagattatt gtccatggga aatctggttt caacattgat ccttaccatg gtgatcaagc     2160
tgctgacata ctggtcgatt tctttgaaaa gtgtaagaaa gatccatctc actgggataa     2220
gatctcccaa ggaggcttga acgtatcga ggagaagtat acatggaaga tttactcgga     2280
gagactattg accctgaccg gagtgtatgg attctggaag catgttttcca accttgaacg     2340 ccgtgagagt cgtcgttacc ttgagatgtt ttatgctctt aagtaccgca agctggctga     2400
atcagttcca ttgcagagg agtaaattta agctgttaaa taacattggg ccggttttc      2460 ttggagaata atattctgtt ttgtaatttc aattggagaa gctcttttgt atttcatctt     2520
```

```
gtcttttcct tttcctttt tcgccggcat tgtttgaaca tggggttgtg cgcccgtcaa    2580
ttccagttaa atatggtgac ttttgttttt c                                  2611

<210> SEQ ID NO 33
<211> LENGTH: 2415
<212> TYPE: DNA
<213> ORGANISM: Gossypium hirsutum

<400> SEQUENCE: 33
atggctaatc ctgtgatcac tcgcgtccac agtctccgtg agcgtttaga tgagaccctt      60
cttgcccaca ggaacgagat tttggccttg ctctcaagga tcgagggcaa aggaaaagga     120
attctgcaac accatcaaat tattctagag tttgaagcta tccctgaaga gaacagaaag     180
aagctcgctg atggtgcatt ttttgaagta ttgaaggcta gtcaggaagc gatcgtgttg     240
cctccatggg ttgcacttgc tgttcgtcca aggcctggtg tttgggagta cattagagtg     300
aatgttcacg cccttgttgt tgaggaactt actgttgctg agtatctcca cttcaaggaa     360
gagcttgttg atggaagttc aaatggaaac tttgttttgg aattggattt tgagcccttc     420
aactcatcat tccccgccc aactctttca aaatccgttg gtaatggtgt ggagttccta     480
aatcgtcacc tttcggcaaa attgttccat gacaaggaga gcatgcaccc tttgctcgaa     540
ttcctcagag tccattgcca caggggcaag aacatgatgt tgaatgacag aattcagaac     600
ttgaatgctc ttcaacatgt tttgaggaaa gcagaggagt atcttggtac cctacctcct     660
gagacaccat gtgccggatt cgaacaccgg ttccaggaaa tcggtttgga agaggttgg      720 ggtgacaccg cacaacgcgt gctcgagatg atccaactcc ttttggatct tcttgaggca     780
cctgatcctt gcacccttga gaagttcctt gggagaatcc ccatggtgtt caatgttgtg     840
attctcactc cccacggata cttcgctcaa gacaatgttt tggggtatcc cgacaccggt     900
ggccaggttg tttacatctt ggatcaagtc cgagctttgg agaatgagat gctcctccgt     960
ataaagcaac aaggactcaa catcacccct cgaatcctca ttattactag acttcttcct    1020
gatgctgtcg gaacaacatg cggtcaacga cttgagaaag tatacggaac agagtactcg    1080
gatattcttc gagtacccct cagaacagaa aagggaattg ttcgtaaatg gatctcaaga    1140
tttgaagtct ggccatactt ggaaacctac acagaggatg ttgctcatga aatctccaaa    1200
gagttgcaag gcaagccaga tctgatcatc ggaaactaca gtgatggcaa tatcgtcgcc    1260
tccttgctcg cacataaatt gggtgtcaca cagtgcacca tcgcccatgc tttggagaag    1320
acaaaatatc ctgattcaga tatctactgg aagaagcttg aagacaaata ccatttctct    1380 tgccaatttta cagctgatct ttttgcaatg aaccatacag atttcatcat caccagtact    1440
ttccaggaaa ttgcaggaag caaggacact gttggtcaat acgagagcca cactgctttc    1500
actcttcctg gtctctaccg tgttgtacat ggtatcgatg tgtttgatcc caaattcaac    1560
attgtttccc ctggtgctga tatggagata tacttcccct tacaccgaaga gaagcggagg    1620 ttgaagcatt tccatactga gatcgaagac cttctttaca gcaaagttga gaatgaagaa    1680
cacttatgtg tgctcaatga ccgcaacaag ccaattctgt tcacaatggc aaggcttgat    1740
cgtgtcaaga acttaaccgg actcgtcgag tggtacggca agaacgcaaa gttgcgtgag    1800
ttggctaacc tcgtagttgt aggtggtgat aggcgaaagg aatctaaaga tttgaagag     1860 aaggccgaaa tgaagaaaat gtttgagctg atcgagaagt acaacttgaa cggccaattc    1920
agatggatat catctcaaat gaacagaatc cgaaatggta acttttaccg atacatttgc    1980
gacacgaaag gtgccttttgt acagcctgca ttgtatgaag cctttggatt gacagttgtg    2040
```

```
gaggcaatga cttgcggttt gccaacattc gcaacctgca acggtggacc agccgagatt    2100
attgtccatg ggaaatctgg tttcaacatt gatccttacc atggtgatca agctgctgac    2160
atactggtcg atttctttga aaagtgtaag aaagatccat ctcactggga taagatctcc    2220
caaggaggct tgaaacgtat cgaggagaag tatacatgga agatttactc ggagagacta    2280
ttgaccctga ccggagtgta tggattctgg aagcatgttt ccaaccttga acgccgtgag    2340
agtcgtcgtt accttgagat gttttatgct cttaagtacc gcaagctggc tgaatcagtt    2400
ccattggcag aggag                                                    2415

<210> SEQ ID NO 34
<211> LENGTH: 732
<212> TYPE: DNA
<213> ORGANISM: Gossypium hirsutum

<400> SEQUENCE: 34
agaaagatga tggaaagggg ttttattgtt ttggccttga cggtggtttt cgccgcgacg     60
gtggttacgg cggctgacga gagtgggtta gcgaatgagt gcagcaaaga tttccagagc    120
gtgatgactt gcttaagctt tgctcaagga aaagcagcgt cgccgtcgaa ggagtgttgt    180
aattcagtgg cggggattaa agagaataaa cccaaatgtt tgtgttatat tttgcaacaa    240
acacaaactt ccgtgctcca aaatctcaaa agcttaggtg ttcaagaaga taagctgttt    300
cagttaccgt cggcttgtca attgaagaac gctagcgtca gtgattgccc aaagcttctt    360
gggttatctc cgagctcacc agacgccgcc atcttcacca actcctcctc taaagcaacg    420
acacccagta cttcaacaac caccgcaacg ccgtcttccg cggccgataa aaccgatagc    480
aaatccagtg gaatcaagct tggtccccac ttcgtcggtt ccacggcggc gctactggtt    540
gctacagcgg ccgtgttttt ccttgtattc ccagctggat ttgcttcaat agtttagggg    600
ttttgcatgg gatttcgaga tttggaggtt tatttattgt tgaagtccat tgttttttaa    660
acggtctcag aaaaaaaatg gactgagttg acaattatga tgattttcg tttattttc     720 ctttttctta tt                                                       732

<210> SEQ ID NO 35
<211> LENGTH: 585
<212> TYPE: DNA
<213> ORGANISM: Gossypium hirsutum

<400> SEQUENCE: 35
atggaaaggg gttttattgt tttggccttg acggtggttt tcgccgcgac ggtggttacg     60
gcggctgacg agagtgggtt agcgaatgag tgcagcaaag atttccagag cgtgatgact    120
tgcttaagct ttgctcaagg aaaagcagcg tcgccgtcga aggagtgttg taattcagtg    180
gcggggatta aagagaataa acccaaatgt ttgtgttata ttttgcaaca aacacaaact    240 tccgtgctc aaaatctcaa aagcttaggt gttcaagaag ataagctgtt tcagttaccg    300
tcggcttgtc aattgaagaa cgctagcgtc agtgattgcc caaagcttct tgggttatct    360
ccgagctcac cagacgccgc catcttcacc aactcctcct ctaaagcaac gacacccagt    420
acttcaacaa ccaccgcaac gccgtcttcc gcggccgata aaaccgatag caaatccagt    480
ggaatcaagc ttggtcccca cttcgtcggt tccacggcgg cgctactggt tgctacagcg    540
gccgtgtttt tccttgtatt cccagctgga tttgcttcaa tagtt                   585

<210> SEQ ID NO 36
<211> LENGTH: 610
```

<212> TYPE: DNA
<213> ORGANISM: Gossypium hirsutum

<400> SEQUENCE: 36

```
caaacactag tagaaggttt agttttacaa acatggctag ttccggtgtc cttaagttgg      60
tttccatgat tctcatggtg tgcatgacga tgatgagtgc acccaaggca gccaaagccg     120
ccatcacgtg cagcgacgtg gtgaaccact tgatcccgtg cttgtcctac gtacaaaacg     180
gcggtacacc cgctgctgca tgctgcagtg gggtaaaagc actctacggc gaggttcaga     240
cctccccgga ccgccaaaac gtgtgcaagt gcatcaaatc ggcggtgaac ggaattccgt     300
acaccagcaa taacctcaat ctcgcagccg gcctacctgc taaatgtggt ctccaactcc     360
cttacagcat cagcccctcc actgactgca acaaggtgca gtgaggttga tgatgatgat     420
atggaaggag tggaagaagg ttccagctca gctagataaa gtagctagct aaggttaaat     480
aagctgtgtt ggtgtgttgt tttttagaaa attccatata taatcgggga agaaaaaaa      540
aatagaaaat gtactttgta actgtatttc gtatgtgata tatataatgt atcgtaatct     600
ttaatttttt                                                            610
```

<210> SEQ ID NO 37
<211> LENGTH: 369
<212> TYPE: DNA
<213> ORGANISM: Gossypium hirsutum

<400> SEQUENCE: 37

```
atggctagtt ccggtgtcct taagttggtt ccatgattc tcatggtgtg catgacgatg       60
atgagtgcac ccaaggcagc caaagccgcc atcacgtgca gcgacgtggt gaaccacttg     120
atcccgtgct tgtcctacgt acaaaacggc ggtacacccg ctgctgcatg ctgcagtggg     180
gtaaaagcac tctacggcga ggttcagacc tccccggacc gccaaaacgt gtgcaagtgc     240
atcaaatcgg cggtgaacgg aattccgtac accagcaata acctcaatct cgcagccggc     300
ctacctgcta aatgtggtct ccaactccct tacagcatca gcccctccac tgactgcaac     360
aaggtgcag                                                             369
```

<210> SEQ ID NO 38
<211> LENGTH: 886
<212> TYPE: DNA
<213> ORGANISM: Gossypium hirsutum

<400> SEQUENCE: 38

```
ccacgcgtcc gcccacgcgt ccgggctcat ttgccaaaaa gaacagacaa tgagatcaag      60
aactactgga atacacagtt gaagaaaagg ttgacgacga tagggatcga ccctgcaact     120
cacaggccta aaaccgatac cctcggttct actcccaagg atgccgctaa ccttagccac     180
atggctcaat gggagagtgc tcggttagaa gctgaagcta gattggtgag agagtcgaaa     240
cgagtttcaa acccttcgca aaaccaattt aggttcacgt cttcatcggc tcctccactg     300
gtaagcaaaa ttgatgttgg tttggctcat gctactaaac cgcaatgcct cgatgtactc     360
aaagcttggc aacgtgtagt cactggattg ttcactttca acactgacaa cctccaatct     420
ccaacatcga cgtcgagctt cacggaaaac acgttaccaa tctcatctgt cgggttcatt     480
gacagctttg tggggaactc aaataacagc tgttgcggaa ataattggga atgtgtggag     540
aaatcgagcc aagttgctga attacaggaa agattggata actcaatggg gttgcatgac     600
atattggatc tctcctcaga agatgtatgg tttcaaggct catacagggc ggaaaatatg     660
atggaagggt attcggacac gttaatggtt tgtgattctg gggatcatcc gaagagtttg     720
```

| | |
|---|---|
| tcaatggagc ctagacaaaa ctttaatgtt ggaacaagta atgctagtag tttcgaagaa | 780 |
| aacaagaatt actggaacaa catccttaat tttgcgaatg cttccccttc tggttcttct | 840 |
| gtcttttgag attaattgtt aagatttgaa ataaataaaa atatat | 886 |

<210> SEQ ID NO 39
<211> LENGTH: 1353
<212> TYPE: DNA
<213> ORGANISM: Gossypium hirsutum

<400> SEQUENCE: 39

| | |
|---|---|
| attcccttc cattgtactg atctttcttt ctttagaatt agtcactcct gttctagatg | 60 |
| aaggttctct ccccaattct tgcttgccta gcgcttgctg tggtggcaag tcatgctgct | 120 |
| ctctcacccg agcaatattg gagctataag ctgccaaata ctccaatgcc aaaggctgtc | 180 |
| aaagaaattc tacatccaga actgatggag gagaaaagta cctctgtaaa tgtaggaggt | 240 |
| ggtggtgtaa acgtcaacac aggaaaaggg aagccagcgg gtggcactca tgtgaacgtt | 300 |
| gggcgcaaag gagttggagt gaacacggga agccagggg gtggcactca tgtgaatgtt | 360 |
| ggaggcaaag gagttggggt gaacactgga agccaggag gtggcaccca tgtgaacgtt | 420 |
| ggaggcaaag gtggaggagt atctgtacac accggacaca agggaaagcc agtaaatgtt | 480 |
| aatgtgagtc cgtttctta ccaatatgca gccagtgaaa ctcaaatcca tgacgatccg | 540 |
| aatgtggctc ttttctttct ggaaaaggat ttacaccccg gcaacaatg agcctgcatt | 600 |
| tcacttgaaa atacagagaa atcccttct taccttatca aactgccaaa aaaatccgtt | 660 |
| ttcatttacg aagttgccag aatttcaca gttttcagt gaacctggat cagtgaaggc | 720 |
| agagatgatg aagaacccat taaggagtgc gaacagccag cgattgaagg agaggaaaaa | 780 |
| tattgtgcac cctcactgga gtcaatgatt gactacagca tttccaaact agggaaagtt | 840 |
| gatcaggcag tctcaacaga agtggaaaaa caaaccccaa cgcacaagta tacaataaca | 900 |
| gctggagtgc agaagatgac aaatgacaaa gctgtagtgt gccacaagca gaattatgca | 960 |
| tatgctgtct ctattgcca taatgagaaa acaacaaggg cttacatggt tcctttagag | 1020 |
| ggtgctgacg gaacaaaagc caaagcagta gcagtctgtc acacagatac atcagcatgg | 1080 |
| aacccaaagc atttggcttt tcaagtccta aaagttgagc caggaaccat tcctgtctgc | 1140 |
| catttccttc ctcgggatca cattgtttgg gtccccaagt aaaagtcctg aagagtagac | 1200 |
| tcatacacta gtttcatc ataggtgca ttaaaacagc ttaaagcaat ctccagtttg | 1260 |
| ttctataata atataccac gagtttagtc atgtaaaatc tatccatgaa tcatgttctt | 1320 |
| agtaatggat aaaatgatag tactttctgt atc | 1353 |

<210> SEQ ID NO 40
<211> LENGTH: 1122
<212> TYPE: DNA
<213> ORGANISM: Gossypium hirsutum

<400> SEQUENCE: 40

| | |
|---|---|
| atgaaggttc tctccccaat tcttgcttgc ctagcgcttg ctgtggtggc aagtcatgct | 60 |
| gctctctcac ccgagcaata ttggagctat aagctgccaa atactccaat gccaaaggct | 120 |
| gtcaaagaaa ttctacatcc agaactgatg gaggagaaaa gtacctctgt aaatgtagga | 180 |
| ggtggtggtg taaacgtcaa cacaggaaaa gggaagccag cgggtggcac tcatgtgaac | 240 |
| gttgggcgca aaggagttgg agtgaacacg ggaaagccag gggtggcac tcatgtgaat | 300 |
| gttggaggca aaggagttgg ggtgaacact ggaaagccag gaggtggcac ccatgtgaac | 360 |

```
gttggaggca aaggtggagg agtatctgta cacaccggac acaagggaaa gccagtaaat      420
gttaatgtga gtccgtttct ttaccaatat gcagccagtg aaactcaaat ccatgacgat      480
ccgaatgtgg ctcttttctt tctggaaaag gatttacacc ccgggcaaca atgagcctgc      540
atttcacttg aaaatacaga gaaatccctt tcttacctta tcaaactgcc aaaaaaatcc      600
gttttcattt acgaagttgc cagaattttc acaagttttc agtgaacctg gatcagtgaa      660
ggcagagatg atgaagaacc cattaaggag tgcgaacagc cagcgattga aggagaggaa      720
aaatattgtg caccctcact ggagtcaatg attgactaca gcatttccaa actagggaaa      780
gttgatcagg cagtctcaac agaagtggaa aaacaaaccc caacgcacaa gtatacaata      840
acagctggag tgcagaagat gacaaatgac aaagctgtag tgtgccacaa gcagaattat      900
gcatatgctg tcttctattg ccataaatga gaaacaacaa gggcttacat ggttcccttta     960 gagggtgctg acggaacaaa agccaaagca gtagcagtct gtcacacaga tacatcagca    1020
tggaacccaa agcatttggc ttttcaagtc ctaaaagttg agccaggaac cattcctgtc    1080
tgccatttcc ttcctcggga tcacattgtt tgggtcccca ag                       1122
```

<210> SEQ ID NO 41
<211> LENGTH: 1373
<212> TYPE: DNA
<213> ORGANISM: Gossypium hirsutum
<220> FEATURE:
<221> NAME/KEY: misc_feature
<222> LOCATION: (895)..(895)
<223> OTHER INFORMATION: n = unknown
<220> FEATURE:
<221> NAME/KEY: misc_feature
<222> LOCATION: (911)..(911)
<223> OTHER INFORMATION: n = unknown
<220> FEATURE:
<221> NAME/KEY: misc_feature
<222> LOCATION: (1270)..(1270)
<223> OTHER INFORMATION: n = unknown
<220> FEATURE:
<221> NAME/KEY: misc_feature
<222> LOCATION: (1336)..(1336)
<223> OTHER INFORMATION: n = unknown

<400> SEQUENCE: 41

```
tgctctcaga atcaaaggaa atggtttttc aattcaattt tccagttctt ctattatgtc       60
ttatgttttt aatgtgtggc agaggcaatg cagtaaggga tttggaaggg aaacatgatt      120
ttgaaagcca tggcagagac gacgaagtgg agagtttaga tgacaagtac gttagcgctt      180
actttcatca aacttttgat tctgcaaatc actttgatgg aggtgatgaa gtgaagaatt      240
tagaagacaa atattcaacg gcttacttcc acaaatcgtt agattctgga accatggca       300 gagatgacaa agcaaagata ttggaagaca agtatgctac tgcgtacttc cacaagactt      360 ctgttttga aaaccatggt gaaggtgaca aattaaagag tttggaagat aaatattccg      420
cggcttactt tcacaacaca caatcttcca aaatgatgaa ggatcacaac atggaacatc      480
accaccatta ccataaccat gttgaaagtg cagagatagg cttgttcacc attgatgaac      540
tacataccct taacgtaggg aagaaattac ccatcttttt cccaataaaa aaccactctc      600
tttaccctcc tttattgcct aaacaaattg ctgacaccat ccctttttca tctttccaag      660
tttctaatat tctacgattc ttctcagttt ctccggactc ccccaaggc aaaagctgtt      720 caagataccct tcgcaaaatg cgaactcgga gcagcgcaag ggggagaccc aaaatctggg      780
ctacctcttt aaaatcttta catgggttc taagcatgca tttgggcccc atgttgattt      840
caagttcata agccaaggca tccccccata ccaacccac tctttcaaag ttacncagtt      900
```

```
ttagaatccc ntgaagagat tgaatctcca aagaaagtag catgtcatcc aatgccatat    960
ctttatgcag tttatttctg tcactttgat gccactgaga ttaaagcttt caaactccgt   1020
ttagttggtg atgttacggg agataaggtg gatgctgttg ttctttgcca tatggatact   1080
tcaggttgga gctctgatca tgtcgctttt cgcatgcttg gtattaagca aggaaacact   1140
gtttgccatg tattttctca aggtaatctt gtttggatta atcagccatc ggatatcgct   1200
gccggtgcca tataagtgtt gaactgttcg atgtagcact catttgccac tacgtatcga   1260
gaccttatcn caatataagt atttaagagc tagtcttatg ttcactaggt ttcatggtgt   1320
ttcgttaatg gtgtgncttt ctatctatat taagtatcaa gtaattaagc aat          1373
```

```
<210> SEQ ID NO 42
<211> LENGTH: 1212
<212> TYPE: DNA
<213> ORGANISM: Gossypium hirsutum
<220> FEATURE:
<221> NAME/KEY: misc_feature
<222> LOCATION: (895)..(895)
<223> OTHER INFORMATION: n = unknown
<220> FEATURE:
<221> NAME/KEY: misc_feature
<222> LOCATION: (911)..(911)
<223> OTHER INFORMATION: n = unknown

<400> SEQUENCE: 42
tgctctcaga atcaaaggaa atggttttc aattcaattt tccagttctt ctattatgtc     60
ttatgttttt aatgtgtggc agaggcaatg cagtaaggga tttggaaggg aaacatgatt   120
ttgaaagcca tggcagagac gacgaagtgg agagtttaga tgacaagtac gttagcgctt   180
actttcatca aacttttgat tctgcaaatc actttgatgg aggtgatgaa gtgaagaatt   240
tagaagacaa atattcaacg gcttacttcc acaaatcgtt agattctgga aaccatggca   300
gagatgacaa agcaaagata ttggaagaca agtatgctac tgcgtacttc cacaagactt   360 ctgttttga aaccatggt gaaggtgaca aattaaagag tttggaagat aaatattccg    420
cggcttactt tcacaacaca caatcttcca aaatgatgaa ggatcacaac atggaacatc   480
accaccatta ccataaccat gttgaaagtg cagagatagg cttgttcacc attgatgaac   540
tacataccct taacgtaggg aagaaattac ccatcttttt cccaataaaa accactctc   600 tttaccctcc tttattgcct aaacaaattg ctgacaccat ccctttttca tctttccaag   660
tttctaatat tctacgattc ttctcagttt ctccggactc ccccaaaggc aaaagctgtt   720
caagatacct tcgcaaaatg cgaactcgga gcagcgcaag ggggagaccc aaaatctggg   780
ctacctcttt aaaatcttta catgggtttc taagcatgca tttgggcccc atgttgattt   840
caagttcata agccaaggca tcccccccata ccaaccccac tctttcaaag ttacncagtt   900
ttagaatccc ntgaagagat tgaatctcca aagaaagtag catgtcatcc aatgccatat   960
ctttatgcag tttatttctg tcactttgat gccactgaga ttaaagcttt caaactccgt  1020
ttagttggtg atgttacggg agataaggtg gatgctgttg ttctttgcca tatggatact  1080
tcaggttgga gctctgatca tgtcgctttt cgcatgcttg gtattaagca aggaaacact  1140
gtttgccatg tattttctca aggtaatctt gtttggatta atcagccatc ggatatcgct  1200
gccggtgcca ta                                                      1212
```

```
<210> SEQ ID NO 43
<211> LENGTH: 1024
<212> TYPE: DNA
<213> ORGANISM: Gossypium hirsutum
```

<400> SEQUENCE: 43

```
gtataacaga ggcagaatcg accggcataa aaataaaaat gggaggctgg gcaatcgcag      60
tgcatggtgg tgctggtgtt cacccaaatc tccctagtga aaggcaagag gaagctgtgc     120
tactcctcaa tcgttgcctt gatattggaa tctgtgcttt tgttctaac ctttccggca     180
ttgactgaca tgaacttgta ttgagggaat ttgaacggat cctttgctta attccgggcg     240
tggatcggca cttacggata aagggacgga ggaaatggaa acttgcttta tggatggacc     300
gaacagacca tgcggtgctg tttcgggtaa acgacatgga agaatccgat atctcttgct     360
cgacttgaaa tggataaaac accacattca tctttgggtt ttgccggcgc cgattatttt     420
gcgaggaaac agggtgtgga gttggtggac aatgaatatt tcattacaga atacaatgtg     480
gggatgctta agttaacaaa agaagcacac tcaatcctgt actattaccg tatcctaacc     540
ctcaccacct gcggaggcag cgcagacatg gaaaatcgat tacgaatgaa ctggttacca     600
atctttctct acatcatata aacagtgggt cgagtcgcac catacaaaca atgtcattgc     660
tctgccgcta cttgcaccgg tggattaatg aacattatga ccggaaagat tggtgactcg     720
ccgctgattg gttcagagac ttatgcttgt gacttattgg ctgtttatgt accggtgaat     780
gtgaagccat tatgctaagc actttggcta cggaagtagc agcgtgatgg aatataaatg     840
gttgaatctt cctgaagctg tggatatgtg attaaactag actatgtgaa ggcaaagctg     900
gtctattgcc tgtcctatat gggaagtgct tggggctgaa tactactggt atgatatggt     960
tggctactga agatggatta tggaagttgt tgtctgcaaa ttgatgttag cttagatgct    1020
ggtc                                                                 1024
```

<210> SEQ ID NO 44
<211> LENGTH: 795
<212> TYPE: DNA
<213> ORGANISM: Gossypium hirsutum

<400> SEQUENCE: 44

```
gtataacaga ggcagaatcg accggcataa aaataaaaat gggaggctgg gcaatcgcag      60
tgcatggtgg tgctggtgtt cacccaaatc tccctagtga aaggcaagag gaagctgtgc     120
tactcctcaa tcgttgcctt gatattggaa tctgtgcttt tgttctaac ctttccggca     180
ttgactgaca tgaacttgta ttgagggaat ttgaacggat cctttgctta attccgggcg     240
tggatcggca cttacggata aagggacgga ggaaatggaa acttgcttta tggatggacc     300
gaacagacca tgcggtgctg tttcgggtaa acgacatgga agaatccgat atctcttgct     360
cgacttgaaa tggataaaac accacattca tctttgggtt ttgccggcgc cgattatttt     420
gcgaggaaac agggtgtgga gttggtggac aatgaatatt tcattacaga atacaatgtg     480
gggatgctta agttaacaaa agaagcacac tcaatcctgt actattaccg tatcctaacc     540
ctcaccacct gcggaggcag cgcagacatg gaaaatcgat tacgaatgaa ctggttacca     600
atctttctct acatcatata aacagtgggt cgagtcgcac catacaaaca atgtcattgc     660
tctgccgcta cttgcaccgg tggattaatg aacattatga ccggaaagat tggtgactcg     720
ccgctgattg gttcagagac ttatgcttgt gacttattgg ctgtttatgt accggtgaat     780
gtgaagccat tatgc                                                      795
```

<210> SEQ ID NO 45
<211> LENGTH: 989
<212> TYPE: DNA
<213> ORGANISM: Gossypium hirsutum

<400> SEQUENCE: 45

```
accatacact ccaagacccc aaccattaac cgcacaagaa gaatcggatc ttgaattggc    60
acaccaaaga ctgttaaaac tttgccaaaa tgcgcgcagt acaacgttcc tttaaccatt   120
gatgccgagg acacgtcgat tcaacccgcc atcgattact tcacgtactc tcggccatca   180
tgtatacaaa gatgataacc ccattgtcta cggcacgatg caagcttact tgaaagacgc   240
gagggagcgg ctgtttaaca cggcgaggac ggcggagaag ctggggattc atatgggggtt   300
taagctggtg agaggcgctt acatgtcgag cgaaaccaag ttggcttctt ccttagggtt   360
cgattcgccg gttcacaaca ccattcaaga cacccatgct tgtttcaatg attgtgcttc   420
gtttatgatt gagaagattg ctgatgggta tggcggactc gttctcgcaa ctcataatct   480
tgagtcaggg aaattggcag catcgaaagc acgaaattta ggaattgaga aggggaatca   540
aaagcttgaa tttgcacagt tatatggaat gtcggaagcg ctgtcgattg gattgagaaa   600
cgcagggttt caagttagca aatacttacc ctatggacca gttgatatgg taatgccata   660
ccttttaagg agagccgaag aaaatagagg actcttatca acttcaagcc ttgatagaac   720
tctcatgggg aaggagttga agagaagatt aaagagcctg caatttgcga agccagagat   780
ggcagcttca gcagcaggta gcatgaagat agaaatagga acgccataaa tgaggttttg   840
attcatagat ggtttgggat gggcaatttt tgccaacaat gtagaattat gaaaaaaaaa   900
taacaatcat tgtaacgttt gggcatttgt cccatgtcaa ttattatttg cattagaaat   960
tgaattttt tctttatttt tgaaaaaaa                                      989
```

<210> SEQ ID NO 46
<211> LENGTH: 410
<212> TYPE: DNA
<213> ORGANISM: Gossypium arboreum

<400> SEQUENCE: 46

```
atcaaggctg ccgtaatgtg caataatgct tgaccaaaga tgatataaaa aaagggaaaa    60
gagaagaaaa ggtgttcgtc cgaaaacaaa tttaacgatt aaagaagtca agagcgcacc   120
tttcaattca tcctttgcgg tcatggtgtt ttgtaagaag gcaaaatcac caagcctgca   180
aggatagtag gttcgggaat tgactttgcc aaagagattt taatattaga tatgttggga   240
gaactcccca ttttgtgtag gctaagagtt caatgtagga gtggactta tactagtcta   300
atttcttttc agtttcatgt gttattgttg aagcattagt tattttggac ttattcctcc   360
attaacaaac atttgttaat ttctgcttaa aaaaaaaaaa aaaaaaaaa                410
```

<210> SEQ ID NO 47
<211> LENGTH: 665
<212> TYPE: DNA
<213> ORGANISM: Gossypium arboreum
<220> FEATURE:
<221> NAME/KEY: misc_feature
<222> LOCATION: (19)..(19)
<223> OTHER INFORMATION: n = unknown
<220> FEATURE:
<221> NAME/KEY: misc_feature
<222> LOCATION: (112)..(112)
<223> OTHER INFORMATION: n = unknown

<400> SEQUENCE: 47

```
attacaccct tttcatttnt agatcacatc ataagaagac tggggttgaa aaaccccacc    60
tcccatggga gtttcttaag cgatgtgagc gtctcctcct ctgtgtaatc tntgattcaa   120
gatccatcca ttatcttccc tctgtattgg ctactgcaac catgatgcac gtcatagacc   180
```

```
aagttgagct tttcaatccc attgactacc aaaatcagct gctgagtgtt cttaaaatta      240
gcaaggaaaa agtaaacgat tgttacaagc tcatccttga tgtatcaaca agaccccagg      300
cccaaggcaa tggtggtgca tgtaagagga aggtggagga gagggttcct agcagcccta      360
gtggagtgat tgatgctgca tttggcagtg atagctcgaa cgattcgtgg ggcacggtgt      420
ccttatcgcc tgagcagcag ccacctttta agaagagcag agcccaagag caagtaatgc      480
gtttgccatc actcaaccga gtcttgtag acattgttgg cagcccttct taattatatc       540
tcccttctct ctctccctcg ctctctccat ctctttcttt gtcccaaaaa gatctatatt      600
tattatgctt atgttcactt ttggttcaag gaatcaaatg ttaagttaaa aaaaaaaaaa      660
aaaaa                                                                  665

<210> SEQ ID NO 48
<211> LENGTH: 626
<212> TYPE: DNA
<213> ORGANISM: Gossypium hirsutum
<220> FEATURE:
<221> NAME/KEY: misc_feature
<222> LOCATION: (581)..(581)
<223> OTHER INFORMATION: n = unknown

<400> SEQUENCE: 48
cttgtttcta tctgtatata accaagggaa ttagacaccc gttcagttga aagagttcag       60
ctgaacaccc caaagatggc caaccacacc gttacctttc tccctaaact atccattgaa      120
gctattcaga cagtgactcc gatgaggata actgaaccac gacagactcg acaagtattg      180 gcagggagc ttgtaggacc cgggatttc caaaggtgtt tgaacgtggt ccagtactac       240
atgaaggaga agaagaaga ctctggttgg ttactggctg ggtggatcaa ggaaacactt       300
gggagagctt tacatgagca accaatgatt tctggtcgtc ttcggaaagg ggaacgaaac      360
gatggagaat tggagattgt ttccaatgac tgcggcatta gactcattga ggcaaggatt      420
cagatgaatc tgtcggattt tcttgatttg aaacaaaggg aagatgctga agctcagctt      480
gttttctgga aagatattga tgagcaaaac ccacagttct ccccactctt ttatgttcag      540
gttactaatt tccagtgtgg tggatattca attgggatta nctgcagtat tcttctggca     600
gatcttttgt taatgaaaga attcct                                           626

<210> SEQ ID NO 49
<211> LENGTH: 644
<212> TYPE: DNA
<213> ORGANISM: Gossypium arboreum
<220> FEATURE:
<221> NAME/KEY: misc_feature
<222> LOCATION: (585)..(585)
<223> OTHER INFORMATION: n = unknown

<400> SEQUENCE: 49
actgagttaa gagtttcaat tcttctactt attatagtta aatatcatat atggccaagt       60
acttgaatgt tgtgcttgtt cttgctctag tagtggttca agctactgca aggaatgtgc      120
ctagcgatgc tgctggtctc aatgaccaaa agaacctcct cacatacggt ggcattggcg      180
gctactctgg catgggttca aatggcatgc caatgggtgg agttgggagt gttggtggta      240
tgactggcct tggtggtaca ggtgggatgg gcgccatggt aggtgttggg tatggaggtg      300
ggcctggcgc tggtggtgga aatgaaggtg gtgttggcat tggcaatgcg cctggtgtcg      360
tccactttcc ttgaactttg ctggatggtt aaaattttaa agcaactagt ttcttgaact      420
ttgctggagg ggtttaaatt ttaaagcaac tagtctaact tacgttaaag agtaaatatta     480
```

```
aagttgctct agagtgtgaa atgttttggg ttatgtgata ggtccatctt tatttttttt    540
atgtcgagtt ttcttttgtt ttgtaatcct tcattgtcgt ggttntgtag ccgacttaaa    600
gtaaataaat tgattttgac aagttaaaaa aaaaaaaaaa acaa                     644

<210> SEQ ID NO 50
<211> LENGTH: 677
<212> TYPE: DNA
<213> ORGANISM: Gossypium arboreum

<400> SEQUENCE: 50
gacactcaaa tataagtagc aaactaacct atgggttatt tggctgattt tgaagggttc     60
atggtgtatt ttggtgcgtg tctgttgaga atccgagttg ttgtcccgtg gtattagctt    120
ctctgtcttg ctggttgcga ttgggcagtt gtgaggtcta taatcaagtg attcaaggaa    180
accgttagct tcattttact tggagaagac aaagaagcta ttgttgtgct ggacttgttc    240 ttgcttttc tctttgtatg gtgtggttta tggtttgtat tatgagtttt atatgaatag     300
aactttgaat ttggtgagaa aattaagaat gagcttggga ggagcagaag tgttgatggc    360
aatagcaggg ttgtgggcag tggttttgag gccattgatg ataaggtatg ccgtagagat    420
gagtcaaatg attggaattt ccgttaggag agttttcagt aatcctcttt ccccttccgt    480
atcgtttttt tattggtact gatatagaaa ttctatgaaa tgagcacaat atgagacacc    540 atttttgct agccaagaag ttagatgagt ggtagacttt ggtttaagct tatcataatt      600
gaaattgtta gactgtaacc cttttgtctc ctttctctaa tttcaaatcc aaattcccat    660
caataaaaaa aaaaaaa                                                    677

<210> SEQ ID NO 51
<211> LENGTH: 692
<212> TYPE: DNA
<213> ORGANISM: Gossypium arboreum

<400> SEQUENCE: 51
ccctacattt ttacgctctg gcacagaaga agaaagccct acctatataa tattacatgc     60
aaatataatg gtatcattag acgttatgac atcgtataat gtaggaggca tctgctacta    120
acatttggca gatgaaatta tttacgaaga acaatgggat attttctgta tttgtttatc    180
atatctggtt acttcaaagc actggttgca acaacagaaa tcaggtttct gctcttcatt    240
gccattgcta gggaggacca taaacaaacc attcttggga gatgggaaac cctcttgcca    300
ttaatgccag aacagtttgc agatattaga agcacttgaa aaataaagct gatacagata    360
attccatatg taattctact ataatctctt tctctttgtt tctgtaatca aattccagta    420
agagcattac tatagtactc atgatttgtt gattcttcta gtgaattgga gagtttagac    480
cctcttgaga agacagtgaa tgtagaactt ggtgcctctt ggatgggaag gctgatgttt    540
tcctaaaaga aggtcgtttt ttcatgtgct gcaatgttcg ccatgtataa agagttcgaa    600
acaatggtga gactctctcc ttgaacttga gaatgatgaa gaaaagtaat ctgtaagcta    660
tcaaaatcat tataacagct gctaagtccc ac                                   692

<210> SEQ ID NO 52
<211> LENGTH: 788
<212> TYPE: DNA
<213> ORGANISM: Gossypium arboreum

<400> SEQUENCE: 52
aagatgatga aaaggggttt tattgttttg gccttgatgg tggttttcgc cgcgacggtg     60
```

```
gttacggggg ctgacgagag tgggttagcg aatgagtgca gcaaagattt ccagagcgtg      120
atgacttgct taagctttgc tcaaggaaaa gcagcgtcgc cgtcgaagga gtgttgtaat      180
tcagtggcgg ggattaaaga gaataaaccc aaatgtttgt gttatatttt gcaacaaaca      240
caaacttccg gtgctcaaaa tctcaaaagc ttaggtgttc aagaagataa gctgtttcag      300
ttaccgtcgg cttgtcaatt gaagaacgct agcgtcagtg attgcccaaa gcttcttggg      360
ttatctccga gctcaccaga cgccgccatc ttcaccaact cctcctctaa agcaacgaca      420
cccagtactt caacaaccac cgcaacgccg tcttccgcgg ccgataaaac cgatagcaaa      480
tccagtggaa tcaagcttgg tccccacttc gtcggttcca cggcggcgct actggttgct      540
acagcggccg tgttttcct tgtattccca gctggatttg cttcaatagt ttaggggttc      600
tgcatgggat ttcgagattt ggaggtttat ttattgttga agtccatttg tttttaaacg      660
gtctcagaaa aaaatggac tgagttgaca attatgatga ttttcgctt attcttgctt      720 tttcttattt gattaaacgt ccctttgaaa taaaacttag tttatttttcc cagcttttccc     780 cctgggaa                                                               788

<210> SEQ ID NO 53
<211> LENGTH: 634
<212> TYPE: DNA
<213> ORGANISM: Gossypium arboreum

<400> SEQUENCE: 53
caaacactag tagaaggttt agttttacaa acatggctag ttccggtgtc cttaagttgg       60
tttccatgat tctcatcgtg tgcatgacgg tgatgagtgc acccaaggca gccaaagccg      120
ccatcacgtg cagcgacgtg gtgaaccact tgatcccgtg cttgtcctac gtacaaaacg      180
gcggtacacc cgctgctgca tgctgcagtg gggtaaaagc actctacggc gaggctcaga      240
cctccccgga ccgccaaaac gtgtgcaagt gcatcaaatc ggcggtgaac ggaattccgt      300
acaccagcaa taacctcaat ctcgcagccg gcctacctgc taaatgtggt ctccaactcc      360
cttacagcat cagcccctcc actgactgca acaaggtgca gtgaggttga tgatgatgat      420
atggaagaag gagtggaaga aggttccagc tcagctagat aaagtagcta gctaaggtta      480
aataagctgt gttggtgtgt tgttttttag aaaattccat atataatcgg ggaaagaaaa      540
aaaaaataga aaatgtactt tgtaactgta tttcgtatgt gatatatata atgtatcgta      600
atctttaatt ttttaaaaaa aaaaaaaaaa aaaa                                  634

<210> SEQ ID NO 54
<211> LENGTH: 884
<212> TYPE: DNA
<213> ORGANISM: Gossypium arboreum

<400> SEQUENCE: 54
cagtgaaact caaatccatg aagacccgaa tgtggctctt ttctttctgg aaaaggatat       60 gcacccggg gcaacaatga gcctacattt cactgaaaat acagagaaat cagctttctt      120
accttatcaa actgcccaaa aaataccgtt ttcatctgac aagttgccag aaattttcaa      180
caagttttca gtgaaacctg atcactgaa ggcagagatg atgaagaaca caattaagga      240
gtgcgaacag ccagcgattg aaggagagga aaaatattgt gcaacctcac tggagtcaat      300
gattgactat agcatttcca aactaggaa agttgatcag gcagtctcaa cagaagtgga      360
aaacaaaacc ccaacgcagc agtatacaat aacagctgga gtgcagaaga tgacaaatgg      420
caaagctgta gtgtgccaca agcagaatta tgcatatgct gtcttctatt gtcataaatc      480
```

```
agaaacaaca agggcttaca tggttccttt agagggtgct gacggaacaa aagccaaagc    540
agtagcagtc tgccacacag atacatcagc atggaaccca aagcatttgg cttttcaagt    600
cctaaaagtt gagccaggaa ccattcctgt ctgccatttc cttcctcggg atcacattgt    660
ttgggtccct aagtaaaagt cctgaagagt agattcatac actatagttt cttcacagtg    720
tgcattaaaa cagcttaaag caatatccag tttgttctat aataatatac ccacaagttt    780
agtcatgtaa aatctatcca tgaatcatgt tcttagtaat ggataaaatg atattacttt    840
ctgtatcaca agggtttggt gataaatgta ttagtatttt aagt                     884
```

```
<210> SEQ ID NO 55
<211> LENGTH: 690
<212> TYPE: DNA
<213> ORGANISM: Gossypium arboreum

<400> SEQUENCE: 55
ggagtgctct cagaatcaaa ggaaatggtt tttcaattca attttccagt tcttctatta     60
tgtcttatgt ttttaatgtg tggcagaggc aatgcagtaa gggatttgga agggaaacat    120
gattttgaaa gccatggcag agacgacgaa gtggagagtt tagatgacaa gtacgttagc    180
gcttactttc atcaaacttt tgattctgca aatcactttg atggaggtga tgaagtgaag    240
aatttagaag acaaatattc aacggcttac ttccacaaat cgttagattc tggaaaccat    300
ggaagagatg acaaagcaaa gatattggaa gacaagtatg ctactgcgta cttccacaag    360
acttctgttt ttgaaaacca tggtgaaggt gacaaattaa agagtttgga agataaatat    420
tccgcggctt acttttcacaa cacacaatct tccaaaatga tgaaggatca caacatggaa    480
catcaccacc attaccataa cctgttgaa agtgcagaga taggcttgtt caccattgat    540
gaactacata cctttaacgt agggaagaaa ttacccatct ttttcccaat aaaaaaccac    600
tctctttacc ctccttatt gcctaaacaa attgctgaca ccatccctt ttcatcttcc      660 caagtttcta atattctacg attcttctca                                     690
```

```
<210> SEQ ID NO 56
<211> LENGTH: 653
<212> TYPE: DNA
<213> ORGANISM: Gossypium arboreum

<400> SEQUENCE: 56
ggcacgagca gaatgaccgg cagagaataa aatgggaggc tgggcaatcg cagtgcatgg     60
tggtgctggt gtagacccaa atctccctaa tgaaaggcaa gaggaagcta aaagactcct    120
cactcgttgc cttgatattg gaatctctgc tcttcgttct aacctctccg ccattgacgt    180
cgttgaactt gtcgtgaggg aattggaaac ggatccttg tttaattccg ggcgtggatc      240
agcacttacg gagaaaggga cggtggaaat ggaagctagt attatggatg gaccgaagag    300
acgatgcggt gctgtttcgg gtttaacgac ggtgaagaat ccgatatctc ttgctcgact    360
tgttatggat aaaacaccac attcgtattt gggttttgcc ggcgccgaag agtttgcgag    420
gaaacagggt gtggagttgg tggacaatga atatttcatt acagaagaca atgtggggat    480
gcttaagtta gcaaaagaag caaactcaat cctgttcgat taccgtatcc caaccctcac    540
cacctgcggt ggcggcgcag ccatggaaaa tcaattacaa atgaacggct taccaatcag    600
tctctacgcc ccagaaacag taggctgcgt tgtagttgac aaacaggtca ttg           653
```

```
<210> SEQ ID NO 57
<211> LENGTH: 612
```

-continued

```
<212> TYPE: DNA
<213> ORGANISM: Gossypium arboreum

<400> SEQUENCE: 57
tttttttttt tttttcataa ttctacattg ttggcaaaaa ttgcccatcc caaaccatct      60
atgaatcaaa acctcactta tggggtgcct atttctatct tcatgctacc tgctgctgta     120
gctgccatct ctggcttcgc aaattgcagg ctctttaatc ttctcttcaa ctccttcccc     180
atgagaggtc tatcaaggct tgaagttgat aagagtcctc tattttcttc ggctctcctt     240
aaaaggtatg gcattaccat atcaactggt ccatagggta agtatttgct aacttgaaac     300
cctgcgtttc tcaatccaaa cgacagcgct tccgacattc catataactg tgcaaattca     360
agcttttgat tccccttctc aattcctaaa tttcgtgctt tcgatgctgc caatttccct     420
gactcaagat tatgagttgc cagaatgagt ccgccatacc catcagcaat cttctcaatc     480
ataaacgaag cacaatcatt gaaacaagca tgggtgtctt gaatggtgtt gtgaaccggc     540
gaatcgaacc ctaaggaaga agccaacttg gtttcgctcg acatgtaagc gcctctcacc     600
agcttaaacg cc                                                        612

<210> SEQ ID NO 58
<211> LENGTH: 3
<212> TYPE: RNA
<213> ORGANISM: Artificial Sequence
<220> FEATURE:
<223> OTHER INFORMATION: Stem loop structure of dsRNA

<400> SEQUENCE: 58 ccc                                                                    3

<210> SEQ ID NO 59
<211> LENGTH: 4
<212> TYPE: RNA
<213> ORGANISM: Artificial Sequence
<220> FEATURE:
<223> OTHER INFORMATION: Stem loop structure of dsRNA

<400> SEQUENCE: 59 uucg                                                                   4

<210> SEQ ID NO 60
<211> LENGTH: 5
<212> TYPE: RNA
<213> ORGANISM: Artificial Sequence
<220> FEATURE:
<223> OTHER INFORMATION: Stem loop structure of dsRNA

<400> SEQUENCE: 60 ccacc                                                                  5

<210> SEQ ID NO 61
<211> LENGTH: 6
<212> TYPE: RNA
<213> ORGANISM: Artificial Sequence
<220> FEATURE:
<223> OTHER INFORMATION: Stem loop structure of dsRNA

<400> SEQUENCE: 61 cuggag                                                                 6

<210> SEQ ID NO 62
<211> LENGTH: 6
<212> TYPE: RNA
<213> ORGANISM: Artificial Sequence
```

```
<220> FEATURE:
<223> OTHER INFORMATION: Stem loop structure of dsRNA

<400> SEQUENCE: 62 aagcuu                                                                    6

<210> SEQ ID NO 63
<211> LENGTH: 7
<212> TYPE: RNA
<213> ORGANISM: Artificial Sequence
<220> FEATURE:
<223> OTHER INFORMATION: Stem loop structure of dsRNA

<400> SEQUENCE: 63 ccacacc                                                                   7

<210> SEQ ID NO 64
<211> LENGTH: 9
<212> TYPE: RNA
<213> ORGANISM: Artificial Sequence
<220> FEATURE:
<223> OTHER INFORMATION: Stem loop structure of dsRNA

<400> SEQUENCE: 64 uucaagaga                                                                 9

<210> SEQ ID NO 65
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 65
agaacatgat gtgtgctgc                                                     19

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 66
agctgtgaac tgctcactc                                                     19

<210> SEQ ID NO 67
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 67 tcaaccctc ctcaaagcaa cc                                                  22

<210> SEQ ID NO 68
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 68
attccattac cagacgatga tgac                                               24
```

```
<210> SEQ ID NO 69
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 69
gctttctctt ggatcag                                              17

<210> SEQ ID NO 70
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 70
caataacaca tgaaaccag                                            19

<210> SEQ ID NO 71
<211> LENGTH: 12
<212> TYPE: DNA
<213> ORGANISM: Artificial Sequence
<220> FEATURE:
<223> OTHER INFORMATION: Oligonucleotide primer

<400> SEQUENCE: 71
cccacgcgtc cg                                                   12

<210> SEQ ID NO 72
<211> LENGTH: 14
<212> TYPE: DNA
<213> ORGANISM: Artificial sequence
<220> FEATURE:
<223> OTHER INFORMATION: Oligonucleotide primer

<400> SEQUENCE: 72
aaaaaagggc ggcc                                                 14

<210> SEQ ID NO 73
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 73
caagacaagg aaggcatccc ac                                        22

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 74
tcggaactct ccacctccaa ag                                        22
```